US006419931B1

(12) United States Patent
Vitiello et al.

(10) Patent No.: US 6,419,931 B1
(45) Date of Patent: Jul. 16, 2002

(54) COMPOSITIONS AND METHODS FOR ELICITING CTL IMMUNITY

(75) Inventors: Maria A. Vitiello, La Jolla; Robert W. Chestnut, Cardiff by the Sea; Alessandro D. Sette, La Jolla; Esteban Celis, San Diego; Howard Grey, La Jolla, all of CA (US)

(73) Assignee: Epimmune Inc., San Diego, CA (US)

( * ) Notice: Subject to any disclaimer, the term of this patent is extended or adjusted under 35 U.S.C. 154(b) by 0 days.

(21) Appl. No.: 08/197,484

(22) Filed: Feb. 16, 1994

Related U.S. Application Data

(63) Continuation-in-part of application No. 07/935,811, filed on Aug. 26, 1992, now abandoned, which is a continuation-in-part of application No. 07/874,491, filed on Apr. 27, 1992, now abandoned, which is a continuation-in-part of application No. 07/827,682, filed on Jan. 29, 1992, now abandoned, which is a continuation-in-part of application No. 07/749,568, filed on Aug. 26, 1991, now abandoned.

(51) Int. Cl.⁷ ...................... A61K 39/295; A61K 39/12; A61K 39/29; A61K 39/21

(52) U.S. Cl. ................................ 424/201.1; 424/204.1; 424/208.1; 424/227.1; 424/228.1

(58) Field of Search .......................... 424/194.1, 189.1, 424/196.1, 227.1, 197, 265.1, 277.1, 228.1, 450, 208.1, 201.1, 204.1

(56) References Cited

U.S. PATENT DOCUMENTS

| 4,235,877 A | | 11/1980 | Fullerton ...................... 424/89 |
| 4,428,941 A | | 1/1984 | Galibert et al. ................ 424/88 |
| 4,487,715 A | | 12/1984 | Nitecki et al. .............. 525/54.1 |
| 4,599,230 A | * | 7/1986 | Milich et al. |
| 4,599,231 A | | 7/1986 | Milich et al. .................. 424/89 |
| 4,818,527 A | * | 4/1989 | Thornton et al. |
| 4,837,028 A | | 6/1989 | Allen .......................... 424/450 |
| 4,882,145 A | | 11/1989 | Thorton et al. ................ 424/88 |
| 4,900,547 A | * | 2/1990 | Levy et al. |
| 4,935,235 A | | 6/1990 | Rutter et al. ................... 424/88 |
| 5,013,548 A | | 5/1991 | Haynes et al. ................. 424/89 |
| 5,017,558 A | | 5/1991 | Vyas ............................ 514/14 |
| 5,019,386 A | | 5/1991 | Machida ...................... 424/89 |
| 5,030,449 A | * | 7/1991 | Berzofsky et al. .......... 530/326 |
| 5,039,522 A | | 8/1991 | Neurath ........................ 424/89 |
| 5,128,319 A | * | 7/1992 | Arlinghaus ................... 514/12 |
| 5,155,210 A | * | 10/1992 | Wrasidlo ..................... 530/317 |
| 5,662,907 A | * | 9/1997 | Kubo et al. ............... 424/185.1 |

FOREIGN PATENT DOCUMENTS

| EP | 105481 | 4/1984 |
| EP | 271302 | 6/1988 |
| EP | 429816 | 6/1991 |
| EP | 431327 | 6/1991 |
| EP | 433242 | 6/1991 |
| JP | 60-161999 | 8/1985 |
| WO | 93/03764 | 3/1993 |

OTHER PUBLICATIONS

Fayolle, C. et al. 1991 In vivo induction of CTL response by a free synthetic peptide requires $CD4^+$ T cell help. J. Immun. 147:4069–4073.*

Lasarte, J. et al. 1992. Induction of CTL in mice against the principal neutralizing domain of HIV–1 . . . Cellular Immunology 141: 211–218.*

Widmann et al. 1992. T helper epitopes enhance the Cyto. response of mice immunized w/MHC class–I rest. Malaria peptides J. Immun. Meth. 155:95–99.*

Widmann et al. 1991. Differential stability of Antigenic MHC class–I restr. synthetic peptides. J. of. Immunol. 147: 3745–3751.*

Martinon et al. 1992. Immunization of mice w/Lipopeptides by passes the prerequisite for adjuvent. J. of Immun. 149: 3416–3422.*

Romero et al. 1992. Immunization w/Synthetic peptides containing adrenal malaria epitope induces . . . J. Immunol. 148: 1871–1878.*

Carbone, F. et al. 1989. J. Exp Med. Induction of ovalbumin specific cytotoxic T cells by in vivo peptide immunization vol. 169 pp. 603–612.*

Staerz, U. et al. 1987. Nature. vol. 329 pp. 449–451 cytotoxic lymphocytes against a soluble protein.*

Zinkernagel et al., "The Lymphoreticular System in Triggering Virus Plus Self–Specific Cytotoxic T Cells: Evidence for T Help", *J. Exp. Med.*, 147:897–911 (1978).

von Boehmer et al., "Distinct Ir Genes for Helper and Killer Cells in the Cytotoxic Response to H–Y Antigen", *J. Exp. Med.*, 150:1134–1142 (Nov., 1979).

Melief et al., "Cooperation Between Subclasses of T Lymphocytes in the in vitro Generation of Cytotoxicity Against a Mutant H–2K Difference An Analysis with Anti–Lyt Antisera", *Eur. J. Immunol.* 9:7–12 (1979).

Widmer et al., "Antigen–Driven Helper Cell–independent Cloned Cytolytic T Lymphocytes", *Nature* 294:750–752 (1981).

Lerner et al., "Chemically Synthesized Peptides Predicted form the Nucleotide Sequence of the Hepatitis B Virus Genome Elicit Antibodies Reactive with the Native Envelope Protein of Dane Particles", *Proc. Natl. Acad. Sci. USA* 78:3403–3407 (Jun., 1981).

(List continued on next page.)

*Primary Examiner*—Donna C. Wortman
(74) *Attorney, Agent, or Firm*—Morrison & Foerster LLP

(57) ABSTRACT

Cytotoxic T lymphocyte responses are effectively induced to an antigen of interest, particularly viral, bacterial, parasitic and tumor antigens. Compositions, including pharmaceutical compositions, of CTL-inducing peptide and an adjuvant or a lipidated peptide which induces a helper T cell (HTL) response stimulate the antigen specific CTL response. Among the viral antigens to which the CTL responses are effectively induced in humans are those of hepatitis B. The CTL response may be optimized by a regimen of two or more booster administrations. Cocktails of two or more CTL inducing peptides are employed to optimize epitope and/or MHC class I restricted coverage.

27 Claims, 27 Drawing Sheets

OTHER PUBLICATIONS

Bhatnagar et al., "Immune Response to Synthetic Peptide Analogues of Hepatitis B Surface Antigen Specific for the Determinant", *Proc. Natl. Acad. Sci. USA* 79:4400–44–4 (Jul., 1982).

Mondelli et al., "Specificity of T Lymphocyte Cytotoxicity to Autologous Hepatocytes in Chronic Hepatitis B Virus Infection: Evidence that t Cells are Directed Against HBV Core Antigen Expressed on Hepatocytes", *J. Immunol.*, 129:2773–2778 (Dec., 1982).

von Boehmer et al., "Autonomously Proliferating K/D–restricted Cytolytic T Cell Clones", *Eur. J. Immunol.* 13:176–179 (1983).

Neurath et al., "Specificity of Antibodies Elicited by a Synthetic Peptide having a Sequence in Common with a Fragment of a Virus Protein—The Hepatitis B Surface Antigen", *Develop. Biol. Standard*, 54:103–112 (1983).

von Boehmer et al., "Lyt–2 T Cell–Independent Functions of Lyt–2⁺ Cells Stimulated with Antigen or Concanavalin A", *J. Immunol.*, 133:59–64 (Jul., 1984).

Milich et al., "Immunogenetics and Cellular Correlates of the Immune Response to Hepatitis B Surface Antigen Determinants", *Adv. Hepatitis Res.* Masson, NY, NY USA 91–109 (1984).

Munekata (ed.) "Peptide Chemistry 1983" published 1984 by Protein Research Foundation (OSAKA), pp. 215–220.

Sprent et al., "Properties of Purified T Cell Subsets", *J. Exp. Med.*, 162:2068–2088 (Dec., 1985).

Bessler et al., "The Synthetic Analog of Bacterial Lipoprotein are Potent Immunoadjuvants in Combination with or Covalently Linked to Antigen", *Prog. Leukoycte Biol.* 5:337–344 (1986).

Watari et al., "A Synthetic Peptide Induces Long–Term Protection from Lethal Infection with Herpes Simplex Virus 2", *J. Exp. Med.*, 165:459–470 (Feb., 1987).

Gotch et al., "Cytotoxic T Lymphocytes Recognize a Fragment of Influenza Virus Matrix Protein in Associate with HLA–A2", *Nature* 326:881–882 (Apr. 30, 1987).

Buller et al., "Induction of Cytotoxic T–Cell Responses in vivo in the Absence of CD4 Helper Cells", *Nature* 328:76–79 (Jul. 2, 1987).

Milich et al., "Immune Response to Hepatitis B Virus Core Antigen (HBcAg): Localization of T Cell Recognition Sites Within HBcAg/HBeAg", *J. Immunol.*, 139:1223–1231 (Aug. 15, 1987).

Milich et al., "Antibody Production to the Nucleocapsid and Envelope of the Hepatitis B Virus Primed by a Single Synthetic T Cell Site", *Nature* 329:547–549 (Oct. 8, 1987).

Mondelli et al., "Definition of Hepatitis B Virus (HBV)–specific Target Antigens Recognized by Cytotoxic T Cells in Acute HBV Infection", *Clin. Exp. Immunol.*, 63:242–250 (1987).

Milich et al., "Hepatitis B Synthetic Immunogen Comprised of Nucleocapsid T–cell Sites and an Envelope B–cell Epitope", *Proc. Natl. Acad. Sci. USA* 85:1610–1614 (Mar., 1988).

Celis et al., "Recognition of Hepatitis B Surface Antigen by Human T Lymphocytes" *J. Immunol.* 140:1808–1815 (Mar. 15, 1988).

Carbone et al., "Induction of Cytotoxic T Lymphocytes by Primary in vitro Stimulation with Peptides", *J. Exp. Med.*, 167:1767–1779 (Jun., 1988).

Moore et al., "Introduction of Soluble Protein into the Class I Pathway of Antigen Processing and Presentation", *Cell* 54:777–785 (Sep. 9, 1988).

Milich et al., "Comparative Immunogenicity of Hepatitis B Virus Core and E Antigens", *J. Immunol.* 141:3617–3624 (Nov. 15, 1988).

Gotch et al., "Recognition of Influenza A Matrix Protein by HLA–A2–Restricted Cytotoxic T Lymphocytes", *J. Exp. Med.* 163:2045–2057 (Dec., 1988).

Milich, "T– and B–cell Recognition of Hepatitis B Viral Antigens", *Immunol. Today* 9:380–386 (1988).

Hayashi et al., "Studies on Peptides CLXVI. Solid–Phase Synthesis and Immunological Properties of Fragment Peptides Related to Human Hepatitis B virus Surface Antigen (HBsAg) and Its Pre–S2 Gene" *Chem. Pharm. Bull.* 36(12):4993–4994 (1988).

Braciale et al., "Class I Major Histocompatibility Complex–restricted Cytolytic T Lymphocytes Recognize a Limited Number of sites on the Influenza Hemagglutinin", *Proc. Natl. Acad. Sci. USA* 86:277–281 (Jan., 1989).

Reitermann et al., "Lipopeptide Derivatives of Bacterial Lipoprotein Constitute Potent Immune Adjuvants Combined with or Covalently Coupled to Antigen or Hapten", *Biol. Chem.* 370:343–352 (Apr., 1989).

Ishioka et al., "Induction of Class I MHC–restricted, Peptide–specific Cytolytic T Lymphocytes by Peptide Priming in vivo", *J. Immunol.*, 143:1094–1100 (Aug. 15, 1989).

Klavinskis et al., "Molecularly Engineered Vaccine Which Expresses an Immunodominant T–cell Epitope Induces Cytotoxic T Lymphocytes that Confer Protection for Lethal Virus Infection," *J. Virol.*, 63:4311–4316 (Oct., 1989).

Bevan, "Stimulating Killer Cells", *Nature* 342:478–479 (Nov. 30, 1989).

Deres et al., "In vivo Priming of Virus–Specific Cytotoxic T Lymphocytes with Synthetic Lipopeptide Vaccine", *Nature* 342:561–564 (Nov. 30, 1989).

Tam et al., "Vaccine Engineering: Enhancement of Immunogenicity of Synthetic Peptide Vaccines Related to Hepatitis in Chemically Defined Models Consisting of T– and B–cell Epitopes", *Proc. Natl. Acad. Sci. USA* 86:9084–9088 (Dec., 1989).

Van Bleek et al., "Isolation of an Endogenously Processed Immunodominant Viral Peptide from the Class IH–2K$^b$ Molecule", *Nature* 348:213–216 (Nov. 15, 1990).

Rotzschke et al., "Isolation and Analysis of Naturally Processed Viral Peptides as Recognized by Cytotoxic T cells", *Nature* 348:252–254 (Nov. 15, 1990).

Moriyama et al., "Immunobiology and Pathogenesis of Hepatocellular Injury in Hepatitis B Virus Transgenic Mice", *Science* 248:361–364 (Apr. 20, 1990).

Aichele et al., "Antiviral Cytotoxic T Cell Response Induced by in vivo Priming with a Free Synthetic Peptide", *J. Exp. Med.*, 171:1815–1820 (May, 1990).

Aggarwal et al., "Oral Salmonella: Malaria Circumsporozoite Recombinants Induce Specific CD8⁺ Cytotoxic T Cells", *J. Exp. Med.*, 172:1083–1090 (Oct., 1990).

Golvano et al., "Polarity of Immunogens: Implications for Vaccine Design", *Eur. J. Immunol.* 20:2363–2366 (1990).

Ishioka et al., "Class I MHC–restricted, Peptide–specific Cytotoxic T Lymphocytes Generated by Peptide Priming in vivo", *Vaccines 90*, Cold Spring Harbor Press, pp. 7–11 (1990).

Kast et al., "Protection Against Lethal Sendai Virus Infection by in vivo Priming of Virus–specific Cytotoxic T Lymphocytes with a Free Synthetic Peptide", *Proc. Natl. Acad. Sci. USA* 88:2283–2287 (Mar., 1991).

Schumacher et al., "Peptide Selection by MHC Class I Molecules", *Nature* 350:703–706 (Apr. 25, 1991).

Falk et al., "Allele–specific Motifs Revealed by Sequencing of Self–peptides Eluted from MHC Molecules", *Nature* 351:290–296 (May 23, 1991).

Sarobe et al., "Induction of Antibodies Against a Peptide Hapten Does Not Require Covalent Linkage Between the Hapten and a Class II Presentable T Helper Peptide", *Eur. J. Immunol.* 21:1555–1558 (1991).

Wiesmuller, et al., "Lipopeptide–Helper T–Cell Epitope–CTL Epitope Conjugate Induces Antibodies Against the CTL Epitope", *Innovation Perspect. Solid–Phase Synth. Collect. Papers, Int. Symp. 2nd 1991*, pp. 499–502, (1991).

Cassell et al., "Linked Recognition of Helper and Cytotoxic Antigenic Determinants for the Generation of Cytotoxic T Lymphocytes", *Ann. N.Y. Acad. Sci.*, pp. 51–60 (1991).

Penna et al., "Cytotoxic T Lymphocytes Recognize an HLA–A2–Restricted Epitope within the Hepatitis B Virus Nucleocapsid Antigen", *J. Exp. Med.*, 174:1565–1570 (Dec., 1991).

Ferrari et al., "Identification of Immunodominant T Cell Epitopes of the Hepatitis B Virus Nucleocapsid Antigen", *J. Clin. Invest.*, 88:214–222 (Jul., 1991).

Hopp, "Immunogenicity of a synthetic HBsAg Peptide: Enhancement by Conjugate to a Fatty Acid Carrier", *Molecular Immunol.* 21:13–16 (1984).

\* cited by examiner

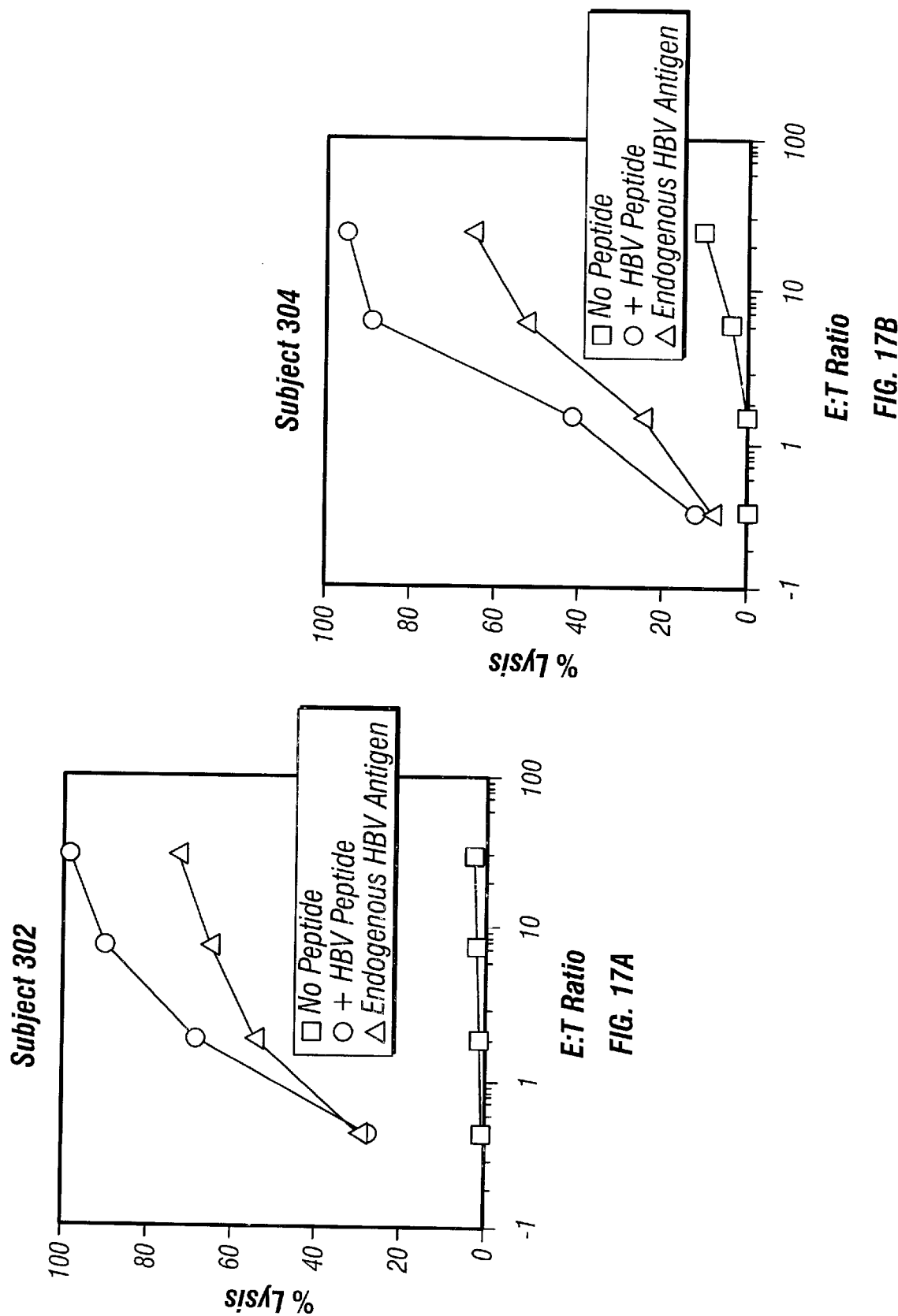

SEQUENCE LISTING (1) GENERAL INFORMATION:

(iii) NUMBER OF SEQUENCES: 153

(2) INFORMATION FOR SEQ ID NO:1:

(i) SEQUENCE CHARACTERISTICS:
      (A) LENGTH: 9 amino acids
      (B) TYPE: amino acid
      (C) STRANDEDNESS: unknown
      (D) TOPOLOGY: unknown (ii) MOLECULE TYPE: peptide (xi) SEQUENCE DESCRIPTION: SEQ ID NO:1:

Glu Ala Asp Pro Thr Gly His Ser Tyr
1                 5

(2) INFORMATION FOR SEQ ID NO:2:

(i) SEQUENCE CHARACTERISTICS:
      (A) LENGTH: 9 amino acids
      (B) TYPE: amino acid
      (C) STRANDEDNESS: unknown
      (D) TOPOLOGY: unknown (ii) MOLECULE TYPE: peptide (xi) SEQUENCE DESCRIPTION: SEQ ID NO:2:

Ala Val Asp Leu Ser His Phe Leu Lys
1                 5

(2) INFORMATION FOR SEQ ID NO:3:

(i) SEQUENCE CHARACTERISTICS:
        (A) LENGTH: 9 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:3:

```
Ile Val Thr Asp Phe Ser Val Ile Lys
1               5
```

(2) INFORMATION FOR SEQ ID NO:4:

(i) SEQUENCE CHARACTERISTICS:
        (A) LENGTH: 10 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:4:

```
Phe Leu Pro Ser Asp Phe Phe Pro Ser Val
1               5                   10
```

(2) INFORMATION FOR SEQ ID NO:5:

(i) SEQUENCE CHARACTERISTICS:
        (A) LENGTH: 9 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:5:

```
Ile Leu Lys Glu Pro Val His Gly Val
1               5
```

(2) INFORMATION FOR SEQ ID NO:6:

(i) SEQUENCE CHARACTERISTICS:
        (A) LENGTH: 8 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:6:

```
Leu Phe Gly Tyr Pro Val Tyr Val
1               5
```

(2) INFORMATION FOR SEQ ID NO:7:

(i) SEQUENCE CHARACTERISTICS:
        (A) LENGTH: 9 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:7:

```
Gly Ile Leu Gly Phe Val Phe Thr Leu
1               5
```

(2) INFORMATION FOR SEQ ID NO:8:

(i) SEQUENCE CHARACTERISTICS:
        (A) LENGTH: 10 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:8:

```
Ile Ala Gly Asn Ser Ala Tyr Glu Tyr Val
1               5                   10
```

(2) INFORMATION FOR SEQ ID NO:9:

(i) SEQUENCE CHARACTERISTICS:
        (A) LENGTH: 9 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:9:

```
Leu Leu Gly Arg Asn Ser Phe Glu Val
1               5
```

(2) INFORMATION FOR SEQ ID NO:10:

(i) SEQUENCE CHARACTERISTICS:
        (A) LENGTH: 9 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:10:

```
Trp Leu Ser Leu Leu Val Pro Phe Val
1               5
```

(2) INFORMATION FOR SEQ ID NO:11:

(i) SEQUENCE CHARACTERISTICS:
        (A) LENGTH: 17 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:11:

```
Arg Phe Arg Glu Leu Val Ser Glu Phe Ser Arg Met Ala Arg Asp Pro
1               5                   10                  15

Gln
```

(2) INFORMATION FOR SEQ ID NO:12:

(i) SEQUENCE CHARACTERISTICS:
        (A) LENGTH: 10 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:12:

```
Gln Val Pro Leu Arg Pro Met Thr Tyr Lys
1               5                   10
```

(2) INFORMATION FOR SEQ ID NO:13:

(i) SEQUENCE CHARACTERISTICS:
        (A) LENGTH: 11 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:13:

```
Arg Leu Arg Asp Leu Leu Leu Ile Val Thr Arg
1               5                   10
```

(2) INFORMATION FOR SEQ ID NO:14:

(i) SEQUENCE CHARACTERISTICS:
        (A) LENGTH: 11 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:14:

```
Ser Thr Leu Pro Glu Thr Thr Val Val Arg Arg
1               5                   10
```

(2) INFORMATION FOR SEQ ID NO:15:

(i) SEQUENCE CHARACTERISTICS:
        (A) LENGTH: 9 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:15:

```
Ser Arg Tyr Trp Ala Ile Arg Thr Arg
1               5
```

(2) INFORMATION FOR SEQ ID NO:16:

(i) SEQUENCE CHARACTERISTICS:
        (A) LENGTH: 10 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:16:

```
Lys Arg Trp Ile Ile Leu Gly Leu Asn Lys
1               5                   10
```

(2) INFORMATION FOR SEQ ID NO:17:

(i) SEQUENCE CHARACTERISTICS:
        (A) LENGTH: 8 amino acids
        (B) TYPE: amino acid
        (C) STRANDEDNESS: unknown
        (D) TOPOLOGY: unknown (ii) MOLECULE TYPE: peptide

```
        (xi) SEQUENCE DESCRIPTION: SEQ ID NO:17:

Lys Pro Lys Asp Glu Leu Asp Tyr
1               5

(2) INFORMATION FOR SEQ ID NO:18:

(i) SEQUENCE CHARACTERISTICS:
        (A) LENGTH: 8 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:18:

Lys Ser Lys Asp Leu Glu Asp Tyr
1               5

(2) INFORMATION FOR SEQ ID NO:19:

(i) SEQUENCE CHARACTERISTICS:
        (A) LENGTH: 8 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:19:

Lys Pro Asn Asp Lys Ser Leu Tyr
1               5

(2) INFORMATION FOR SEQ ID NO:20:

(i) SEQUENCE CHARACTERISTICS:
        (A) LENGTH: 9 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:20:

Thr Pro Tyr Asp Ile Asn Gln Met Leu
1               5

(2) INFORMATION FOR SEQ ID NO:21:

(i) SEQUENCE CHARACTERISTICS:
        (A) LENGTH: 9 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:21:

Lys Pro Ile Val Gln Tyr Asp Asn Phe
1               5

(2) INFORMATION FOR SEQ ID NO:22:

(i) SEQUENCE CHARACTERISTICS:
        (A) LENGTH: 9 amino acids
        (B) TYPE: amino acid
        (C) STRANDEDNESS: unknown
        (D) TOPOLOGY: unknown (ii) MOLECULE TYPE: peptide
```

(xi) SEQUENCE DESCRIPTION: SEQ ID NO:22:

Tyr Pro Ala Glu Ile Thr Leu Thr Trp
 1               5

(2) INFORMATION FOR SEQ ID NO:23:

(i) SEQUENCE CHARACTERISTICS:
        (A) LENGTH: 8 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:23:

Tyr Leu Lys Asp Gln Gln Leu Leu
1             5

(2) INFORMATION FOR SEQ ID NO:24:

(i) SEQUENCE CHARACTERISTICS:
        (A) LENGTH: 9 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:24:

Glu Leu Arg Ser Arg Tyr Trp Ala Ile
 1               5

(2) INFORMATION FOR SEQ ID NO:25:

(i) SEQUENCE CHARACTERISTICS:
        (A) LENGTH: 9 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:25:

Phe Leu Arg Gly Arg Ala Tyr Gly Ile
 1               5

(2) INFORMATION FOR SEQ ID NO:26:

(i) SEQUENCE CHARACTERISTICS:
        (A) LENGTH: 9 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:26:

Gly Glu Ile Tyr Lys Arg Trp Ile Ile
 1               5

(2) INFORMATION FOR SEQ ID NO:27:

(i) SEQUENCE CHARACTERISTICS:
        (A) LENGTH: 9 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:27:

Asp Cys Lys Thr Ile Leu Lys Ala Leu
1               5

(2) INFORMATION FOR SEQ ID NO:28:

(i) SEQUENCE CHARACTERISTICS:
            (A) LENGTH: 9 amino acids
            (B) TYPE: amino acid
            (C) STRANDEDNESS: unknown
            (D) TOPOLOGY: unknown (ii) MOLECULE TYPE: peptide (xi) SEQUENCE DESCRIPTION: SEQ ID NO:28:

Asp Pro Lys Val Lys Gln Trp Pro Leu
1               5

(2) INFORMATION FOR SEQ ID NO:29:

(i) SEQUENCE CHARACTERISTICS:
            (A) LENGTH: 9 amino acids
            (B) TYPE: amino acid
            (C) STRANDEDNESS: unknown
            (D) TOPOLOGY: unknown (ii) MOLECULE TYPE: peptide (xi) SEQUENCE DESCRIPTION: SEQ ID NO:29:

Tyr Leu Lys Asp Gln Gln Leu Tyr Leu
1               5

(2) INFORMATION FOR SEQ ID NO:30:

(i) SEQUENCE CHARACTERISTICS:
            (A) LENGTH: 9 amino acids
            (B) TYPE: amino acid
            (C) STRANDEDNESS: unknown
            (D) TOPOLOGY: unknown (ii) MOLECULE TYPE: peptide (xi) SEQUENCE DESCRIPTION: SEQ ID NO:30:

Gly Gly Lys Lys Lys Tyr Lys Leu Lys
1               5

(2) INFORMATION FOR SEQ ID NO:31:

(i) SEQUENCE CHARACTERISTICS:
            (A) LENGTH: 9 amino acids
            (B) TYPE: amino acid
            (C) STRANDEDNESS: unknown
            (D) TOPOLOGY: unknown (ii) MOLECULE TYPE: peptide (xi) SEQUENCE DESCRIPTION: SEQ ID NO:31:

Leu Leu Ala Gln Phe Thr Ser Ala Ile
1               5

(2) INFORMATION FOR SEQ ID NO:32:

(i) SEQUENCE CHARACTERISTICS:
            (A) LENGTH: 10 amino acids
            (B) TYPE: amino acid
            (C) STRANDEDNESS: unknown
            (D) TOPOLOGY: unknown (ii) MOLECULE TYPE: peptide (xi) SEQUENCE DESCRIPTION: SEQ ID NO:32:

Leu Leu Val Pro Phe Val Gln Trp Phe Val
1               5                   10

(2) INFORMATION FOR SEQ ID NO:33:

(i) SEQUENCE CHARACTERISTICS:
        (A) LENGTH: 9 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:33:

Trp Leu Ser Leu Leu Val Pro Phe Val
1               5

(2) INFORMATION FOR SEQ ID NO:34:

(i) SEQUENCE CHARACTERISTICS:
        (A) LENGTH: 9 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:34:

Phe Leu Leu Ala Gln Phe Thr Ser Ala
1               5

(2) INFORMATION FOR SEQ ID NO:35:

(i) SEQUENCE CHARACTERISTICS:
        (A) LENGTH: 9 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:35:

Phe Leu Leu Ser Leu Gly Ile His Leu
1               5

(2) INFORMATION FOR SEQ ID NO:36:

(i) SEQUENCE CHARACTERISTICS:
        (A) LENGTH: 9 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:36:

Ala Leu Met Pro Leu Tyr Ala Cys Ile
1               5

(2) INFORMATION FOR SEQ ID NO:37:

(i) SEQUENCE CHARACTERISTICS:
        (A) LENGTH: 10 amino acids
        (B) TYPE: amino acid
        (C) STRANDEDNESS: unknown (D) TOPOLOGY: unknown (ii) MOLECULE TYPE: peptide (xi) SEQUENCE DESCRIPTION: SEQ ID NO:37:

Ile Leu Leu Leu Cys Leu Ile Phe Leu Leu
1               5                   10

(2) INFORMATION FOR SEQ ID NO:38:

(i) SEQUENCE CHARACTERISTICS:
        (A) LENGTH: 9 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:38:

Lys Leu His Leu Tyr Ser His Pro Ile
1               5

(2) INFORMATION FOR SEQ ID NO:39:

(i) SEQUENCE CHARACTERISTICS:
        (A) LENGTH: 9 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:39:

Val Leu Leu Asp Tyr Gln Gly Met Leu
1               5

(2) INFORMATION FOR SEQ ID NO:40:

(i) SEQUENCE CHARACTERISTICS:
        (A) LENGTH: 10 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:40:

Leu Leu Pro Ile Phe Phe Cys Leu Trp Val
1               5                   10

(2) INFORMATION FOR SEQ ID NO:41:

(i) SEQUENCE CHARACTERISTICS:
        (A) LENGTH: 9 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:41:

Val Leu Gln Ala Gly Phe Phe Leu Leu
1               5

(2) INFORMATION FOR SEQ ID NO:42:

(i) SEQUENCE CHARACTERISTICS:
        (A) LENGTH: 10 amino acids
        (B) TYPE: amino acid (C) STRANDEDNESS: unknown
        (D) TOPOLOGY: unknown (ii) MOLECULE TYPE: peptide (xi) SEQUENCE DESCRIPTION: SEQ ID NO:42:

Tyr Leu His Thr Leu Trp Lys Ala Gly Ile
1               5                   10

(2) INFORMATION FOR SEQ ID NO:43:

(i) SEQUENCE CHARACTERISTICS:
        (A) LENGTH: 10 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:43:

Tyr Leu His Thr Leu Trp Lys Ala Gly Val
1               5                   10

(2) INFORMATION FOR SEQ ID NO:44:

(i) SEQUENCE CHARACTERISTICS:
        (A) LENGTH: 9 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:44:

Pro Leu Leu Pro Ile Phe Phe Cys Leu
1               5

(2) INFORMATION FOR SEQ ID NO:45:

(i) SEQUENCE CHARACTERISTICS:
        (A) LENGTH: 10 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:45:

Ile Leu Ser Thr Leu Pro Glu Thr Thr Val
1               5                   10

(2) INFORMATION FOR SEQ ID NO:46:

(i) SEQUENCE CHARACTERISTICS:
        (A) LENGTH: 10 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:46:

Leu Leu Phe Asn Ile Leu Gly Gly Trp Val
1               5                   10

(2) INFORMATION FOR SEQ ID NO:47:

(i) SEQUENCE CHARACTERISTICS:
        (A) LENGTH: 10 amino acids (B) TYPE: amino acid
            (C) STRANDEDNESS: unknown
            (D) TOPOLOGY: unknown (ii) MOLECULE TYPE: peptide (xi) SEQUENCE DESCRIPTION: SEQ ID NO:47:

Leu Leu Ala Leu Leu Ser Cys Leu Thr Val
1               5                  10

(2) INFORMATION FOR SEQ ID NO:48:

(i) SEQUENCE CHARACTERISTICS:
            (A) LENGTH: 9 amino acids
            (B) TYPE: amino acid
            (C) STRANDEDNESS: unknown
            (D) TOPOLOGY: unknown (ii) MOLECULE TYPE: peptide (xi) SEQUENCE DESCRIPTION: SEQ ID NO:48:

Tyr Leu Val Ala Tyr Gln Ala Thr Val
1               5

(2) INFORMATION FOR SEQ ID NO:49:

(i) SEQUENCE CHARACTERISTICS:
            (A) LENGTH: 9 amino acids
            (B) TYPE: amino acid
            (C) STRANDEDNESS: unknown
            (D) TOPOLOGY: unknown (ii) MOLECULE TYPE: peptide (xi) SEQUENCE DESCRIPTION: SEQ ID NO:49:

Phe Leu Leu Leu Ala Asp Ala Arg Val
1               5

(2) INFORMATION FOR SEQ ID NO:50:

(i) SEQUENCE CHARACTERISTICS:
            (A) LENGTH: 9 amino acids
            (B) TYPE: amino acid
            (C) STRANDEDNESS: unknown
            (D) TOPOLOGY: unknown (ii) MOLECULE TYPE: peptide (xi) SEQUENCE DESCRIPTION: SEQ ID NO:50:

Ile Leu Ala Gly Tyr Gly Ala Gly Val
1               5

(2) INFORMATION FOR SEQ ID NO:51:

(i) SEQUENCE CHARACTERISTICS:
            (A) LENGTH: 9 amino acids
            (B) TYPE: amino acid
            (C) STRANDEDNESS: unknown
            (D) TOPOLOGY: unknown (ii) MOLECULE TYPE: peptide (xi) SEQUENCE DESCRIPTION: SEQ ID NO:51:

Asp Leu Met Gly Tyr Ile Pro Leu Val
1               5

(2) INFORMATION FOR SEQ ID NO:52:

(i) SEQUENCE CHARACTERISTICS:

(A) LENGTH: 10 amino acids
         (B) TYPE: amino acid
         (C) STRANDEDNESS: unknown
         (D) TOPOLOGY: unknown (ii) MOLECULE TYPE: peptide (xi) SEQUENCE DESCRIPTION: SEQ ID NO:52:

Tyr Leu Leu Pro Arg Arg Gly Pro Arg Leu
1               5                   10

(2) INFORMATION FOR SEQ ID NO:53:

(i) SEQUENCE CHARACTERISTICS:
         (A) LENGTH: 9 amino acids
         (B) TYPE: amino acid
         (C) STRANDEDNESS: unknown
         (D) TOPOLOGY: unknown (ii) MOLECULE TYPE: peptide (xi) SEQUENCE DESCRIPTION: SEQ ID NO:53:

Ala Leu Ser Thr Gly Leu Ile His Leu
1               5

(2) INFORMATION FOR SEQ ID NO:54:

(i) SEQUENCE CHARACTERISTICS:
         (A) LENGTH: 10 amino acids
         (B) TYPE: amino acid
         (C) STRANDEDNESS: unknown
         (D) TOPOLOGY: unknown (ii) MOLECULE TYPE: peptide (xi) SEQUENCE DESCRIPTION: SEQ ID NO:54:

Leu Leu Ala Leu Leu Ser Cys Leu Thr Ile
1               5                   10

(2) INFORMATION FOR SEQ ID NO:55:

(i) SEQUENCE CHARACTERISTICS:
         (A) LENGTH: 10 amino acids
         (B) TYPE: amino acid
         (C) STRANDEDNESS: unknown
         (D) TOPOLOGY: unknown (ii) MOLECULE TYPE: peptide (xi) SEQUENCE DESCRIPTION: SEQ ID NO:55:

Arg Leu Ile Val Phe Pro Asp Leu Gly Val
1               5                   10

(2) INFORMATION FOR SEQ ID NO:56:

(i) SEQUENCE CHARACTERISTICS:
         (A) LENGTH: 10 amino acids
         (B) TYPE: amino acid
         (C) STRANDEDNESS: unknown
         (D) TOPOLOGY: unknown (ii) MOLECULE TYPE: peptide (xi) SEQUENCE DESCRIPTION: SEQ ID NO:56:

Arg Leu His Gly Leu Ser Ala Phe Ser Leu
1               5                   10

(2) INFORMATION FOR SEQ ID NO:57:

(i) SEQUENCE CHARACTERISTICS:
    (A) LENGTH: 10 amino acids
    (B) TYPE: amino acid
    (C) STRANDEDNESS: unknown
    (D) TOPOLOGY: unknown (ii) MOLECULE TYPE: peptide (xi) SEQUENCE DESCRIPTION: SEQ ID NO:57:

Ile Leu Gly Gly Trp Val Ala Ala Gln Leu
1               5                   10

(2) INFORMATION FOR SEQ ID NO:58:

(i) SEQUENCE CHARACTERISTICS:
        (A) LENGTH: 9 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:58:

Ser Met Val Gly Asn Trp Ala Lys Val
1               5

(2) INFORMATION FOR SEQ ID NO:59:

(i) SEQUENCE CHARACTERISTICS:
        (A) LENGTH: 9 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:59:

Tyr Leu Val Thr Arg His Ala Asp Val
1               5

(2) INFORMATION FOR SEQ ID NO:60:

(i) SEQUENCE CHARACTERISTICS:
        (A) LENGTH: 10 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:60:

Val Leu Ala Ala Leu Ala Ala Tyr Cys Leu
1               5                   10

(2) INFORMATION FOR SEQ ID NO:61:

(i) SEQUENCE CHARACTERISTICS:
        (A) LENGTH: 10 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:61:

Gly Val Ala Gly Ala Leu Val Ala Phe Lys
1               5                   10

(2) INFORMATION FOR SEQ ID NO:62:

(i) SEQUENCE CHARACTERISTICS:
            (A) LENGTH: 8 amino acids
            (B) TYPE: amino acid
            (C) STRANDEDNESS: unknown
            (D) TOPOLOGY: unknown (ii) MOLECULE TYPE: peptide (xi) SEQUENCE DESCRIPTION: SEQ ID NO:62:

Ser Thr Asn Pro Lys Pro Gln Lys
1               5

(2) INFORMATION FOR SEQ ID NO:63:

(i) SEQUENCE CHARACTERISTICS:
            (A) LENGTH: 9 amino acids
            (B) TYPE: amino acid
            (C) STRANDEDNESS: unknown
            (D) TOPOLOGY: unknown (ii) MOLECULE TYPE: peptide (xi) SEQUENCE DESCRIPTION: SEQ ID NO:63:

Gly Pro Arg Leu Gly Val Arg Ala Thr
1               5

(2) INFORMATION FOR SEQ ID NO:64:

(i) SEQUENCE CHARACTERISTICS:
            (A) LENGTH: 20 amino acids
            (B) TYPE: amino acid
            (C) STRANDEDNESS: unknown
            (D) TOPOLOGY: unknown (ii) MOLECULE TYPE: peptide (xi) SEQUENCE DESCRIPTION: SEQ ID NO:64:

Tyr Pro Trp Pro Leu Tyr Gly Asn Glu Gly Leu Gly Trp Ala Gly Trp
1               5                  10                  15

Leu Leu Ser Pro
            20

(2) INFORMATION FOR SEQ ID NO:65:

(i) SEQUENCE CHARACTERISTICS:
            (A) LENGTH: 9 amino acids
            (B) TYPE: amino acid
            (C) STRANDEDNESS: unknown
            (D) TOPOLOGY: unknown (ii) MOLECULE TYPE: peptide (xi) SEQUENCE DESCRIPTION: SEQ ID NO:65:

Leu Leu Met Gly Thr Leu Gly Ile Val
1               5

(2) INFORMATION FOR SEQ ID NO:66:

(i) SEQUENCE CHARACTERISTICS:
            (A) LENGTH: 9 amino acids
            (B) TYPE: amino acid
            (C) STRANDEDNESS: unknown
            (D) TOPOLOGY: unknown (ii) MOLECULE TYPE: peptide (xi) SEQUENCE DESCRIPTION: SEQ ID NO:66:

Tyr Met Leu Asp Leu Gln Pro Glu Thr

```
1               5
```

(2) INFORMATION FOR SEQ ID NO:67:

(i) SEQUENCE CHARACTERISTICS:
        (A) LENGTH: 9 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:67:

```
Phe Ala Phe Arg Asp Leu Cys Ile Val
1               5
```

(2) INFORMATION FOR SEQ ID NO:68:

(i) SEQUENCE CHARACTERISTICS:
        (A) LENGTH: 9 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:68:

```
Thr Leu Gly Ile Val Cys Pro Ile Cys
1               5
```

(2) INFORMATION FOR SEQ ID NO:69:

(i) SEQUENCE CHARACTERISTICS:
        (A) LENGTH: 9 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:69:

```
Thr Leu His Glu Tyr Met Leu Asp Leu
1               5
```

(2) INFORMATION FOR SEQ ID NO:70:

(i) SEQUENCE CHARACTERISTICS:
        (A) LENGTH: 9 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:70:

```
Gly Thr Leu Gly Ile Val Cys Pro Ile
1               5
```

(2) INFORMATION FOR SEQ ID NO:71:

(i) SEQUENCE CHARACTERISTICS:
        (A) LENGTH: 9 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:71:

```
Met Leu Asp Leu Gln Pro Glu Thr Thr
1               5
```

(2) INFORMATION FOR SEQ ID NO:72:

(i) SEQUENCE CHARACTERISTICS:
        (A) LENGTH: 10 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:72:

```
Thr Ile His Asp Ile Ile Leu Glu Cys Val
1               5                   10
```

(2) INFORMATION FOR SEQ ID NO:73:

(i) SEQUENCE CHARACTERISTICS:
        (A) LENGTH: 9 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:73:

```
Val Leu Ala Glu Ala Met Ser Gln Val
1               5
```

(2) INFORMATION FOR SEQ ID NO:74:

(i) SEQUENCE CHARACTERISTICS:
        (A) LENGTH: 10 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:74:

```
Leu Leu Trp Lys Gly Glu Gly Ala Val Val
1               5                   10
```

(2) INFORMATION FOR SEQ ID NO:75:

(i) SEQUENCE CHARACTERISTICS:
        (A) LENGTH: 9 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:75:

```
Leu Leu Trp Lys Gly Glu Gly Ala Val
1               5
```

(2) INFORMATION FOR SEQ ID NO:76:

(i) SEQUENCE CHARACTERISTICS:
        (A) LENGTH: 9 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:76:

Ile Leu Lys Glu Pro Val His Gly Val
1               5

(2) INFORMATION FOR SEQ ID NO:77:

(i) SEQUENCE CHARACTERISTICS:
        (A) LENGTH: 9 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:77:

Ile Val Gly Ala Glu Thr Phe Tyr Val
1               5

(2) INFORMATION FOR SEQ ID NO:78:

(i) SEQUENCE CHARACTERISTICS:
        (A) LENGTH: 9 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:78:

Ile Ile Gly Ala Glu Thr Phe Tyr Val
1               5

(2) INFORMATION FOR SEQ ID NO:79:

(i) SEQUENCE CHARACTERISTICS:
        (A) LENGTH: 9 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:79:

Leu Trp Val Thr Val Tyr Tyr Gly Val
1               5

(2) INFORMATION FOR SEQ ID NO:80:

(i) SEQUENCE CHARACTERISTICS:
        (A) LENGTH: 9 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:80:

Leu Met Val Thr Val Tyr Tyr Gly Val
1               5

(2) INFORMATION FOR SEQ ID NO:81:

(i) SEQUENCE CHARACTERISTICS:
        (A) LENGTH: 9 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:81:

Lys Met Val Glu Leu Val His Phe Leu
1               5

(2) INFORMATION FOR SEQ ID NO:82:

(i) SEQUENCE CHARACTERISTICS:
        (A) LENGTH: 10 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:82:

Lys Met Val Glu Leu Val His Phe Leu Leu
1               5                   10

(2) INFORMATION FOR SEQ ID NO:83:

(i) SEQUENCE CHARACTERISTICS:
        (A) LENGTH: 10 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:83:

Leu Val Phe Gly Ile Glu Leu Met Glu Val
1               5                   10

(2) INFORMATION FOR SEQ ID NO:84:

(i) SEQUENCE CHARACTERISTICS:
        (A) LENGTH: 9 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:84:

Lys Val Leu Glu Tyr Val Ile Lys Val
1               5

(2) INFORMATION FOR SEQ ID NO:85:

(i) SEQUENCE CHARACTERISTICS:
        (A) LENGTH: 10 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:85:

Lys Val Ala Asp Leu Val Gly Phe Leu Leu
1               5                   10

(2) INFORMATION FOR SEQ ID NO:86:

(i) SEQUENCE CHARACTERISTICS:
        (A) LENGTH: 9 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:86:

Lys Val Ala Glu Phe Val His Phe Leu
1               5

(2) INFORMATION FOR SEQ ID NO:87:

(i) SEQUENCE CHARACTERISTICS:
        (A) LENGTH: 9 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:87:

Cys Ile Leu Glu Ser Leu Phe Arg Ala
1               5

(2) INFORMATION FOR SEQ ID NO:88:

(i) SEQUENCE CHARACTERISTICS:
        (A) LENGTH: 9 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:88:

Phe Leu Trp Gly Pro Arg Ala Leu Ala
1               5

(2) INFORMATION FOR SEQ ID NO:89:

(i) SEQUENCE CHARACTERISTICS:
        (A) LENGTH: 10 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:89:

Val Met Ile Ala Met Glu Gly Gly His Ala
1               5                   10

(2) INFORMATION FOR SEQ ID NO:90:

(i) SEQUENCE CHARACTERISTICS:
        (A) LENGTH: 9 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:90:

Leu Val Leu Gly Thr Leu Glu Glu Val
1               5

(2) INFORMATION FOR SEQ ID NO:91:

(i) SEQUENCE CHARACTERISTICS:
        (A) LENGTH: 9 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:91:

Ala Leu Arg Glu Glu Glu Glu Gly Val
1               5

(2) INFORMATION FOR SEQ ID NO:92:

(i) SEQUENCE CHARACTERISTICS:
        (A) LENGTH: 10 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:92:

Ala Leu Ala Glu Thr Ser Tyr Val Lys Val
1               5                   10

(2) INFORMATION FOR SEQ ID NO:93:

(i) SEQUENCE CHARACTERISTICS:
        (A) LENGTH: 9 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:93:

Tyr Val Ile Lys Val Ser Ala Arg Val
1               5

(2) INFORMATION FOR SEQ ID NO:94:

(i) SEQUENCE CHARACTERISTICS:
        (A) LENGTH: 9 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:94:

Arg Ala Leu Ala Glu Thr Ser Tyr Val
1               5

(2) INFORMATION FOR SEQ ID NO:95:

(i) SEQUENCE CHARACTERISTICS:
        (A) LENGTH: 14 amino acids
        (B) TYPE: amino acid
        (C) STRANDEDNESS: unknown
        (D) TOPOLOGY: unknown (ii) MOLECULE TYPE: peptide (ix) FEATURE:
        (A) NAME/KEY: Peptide
        (B) LOCATION: 1..14
        (D) OTHER INFORMATION: /note= "Tetanus toxoid 830-843"

(xi) SEQUENCE DESCRIPTION: SEQ ID NO:95:

Gln Tyr Ile Lys Ala Asn Ser Lys Phe Ile Gly Ile Thr Glu
1               5                   10

(2) INFORMATION FOR SEQ ID NO:96:

(i) SEQUENCE CHARACTERISTICS:
    (A) LENGTH: 17 amino acids
    (B) TYPE: amino acid
    (C) STRANDEDNESS: unknown
    (D) TOPOLOGY: unknown (ii) MOLECULE TYPE: peptide (ix) FEATURE:
    (A) NAME/KEY: Peptide
    (B) LOCATION: 1..17
    (D) OTHER INFORMATION: /note= "Malaria circumsporozoite 382-398"

(xi) SEQUENCE DESCRIPTION: SEQ ID NO:96:

Lys Ile Ala Lys Met Glu Lys Ala Ser Ser Val Phe Asn Val Val Asn
1               5                   10                  15

Ser (2) INFORMATION FOR SEQ ID NO:97:

(i) SEQUENCE CHARACTERISTICS:
    (A) LENGTH: 21 amino acids
    (B) TYPE: amino acid
    (C) STRANDEDNESS: unknown
    (D) TOPOLOGY: unknown (ii) MOLECULE TYPE: peptide (ix) FEATURE:
    (A) NAME/KEY: Peptide
    (B) LOCATION: 1..21
    (D) OTHER INFORMATION: /note= "Malaria circumsporozoite 378-398"

(xi) SEQUENCE DESCRIPTION: SEQ ID NO:97:

Asp Ile Glu Lys Lys Ile Ala Lys Met Glu Lys Ala Ser Ser Val Phe
1               5                   10                  15

Asn Val Val Asn Ser
            20

(2) INFORMATION FOR SEQ ID NO:98:

(i) SEQUENCE CHARACTERISTICS:
    (A) LENGTH: 14 amino acids
    (B) TYPE: amino acid
    (C) STRANDEDNESS: unknown
    (D) TOPOLOGY: unknown (ii) MOLECULE TYPE: peptide (ix) FEATURE:
    (A) NAME/KEY: Peptide
    (B) LOCATION: 1..14
    (D) OTHER INFORMATION: /note= "Ovalbumin 323-336"

(xi) SEQUENCE DESCRIPTION: SEQ ID NO:98:

Ile Ser Gln Ala Val His Ala Ala His Ala Glu Ile Asn Glu
1               5                   10

(2) INFORMATION FOR SEQ ID NO:99:

(i) SEQUENCE CHARACTERISTICS:
    (A) LENGTH: 13 amino acids
    (B) TYPE: amino acid
    (C) STRANDEDNESS: unknown
    (D) TOPOLOGY: unknown (ii) MOLECULE TYPE: peptide (ix) FEATURE:

(A) NAME/KEY: Peptide
            (B) LOCATION: 1..13
            (D) OTHER INFORMATION: /note= "Influenza epitope 307-319"

(xi) SEQUENCE DESCRIPTION: SEQ ID NO:99:

Pro Lys Tyr Val Lys Gln Asn Thr Leu Lys Leu Ala Thr
1               5                   10

(2) INFORMATION FOR SEQ ID NO:100:

(i) SEQUENCE CHARACTERISTICS:
            (A) LENGTH: 20 amino acids
            (B) TYPE: amino acid
            (C) STRANDEDNESS: unknown
            (D) TOPOLOGY: unknown (ii) MOLECULE TYPE: peptide (ix) FEATURE:
            (A) NAME/KEY: Peptide
            (B) LOCATION: 1..20
            (D) OTHER INFORMATION: /note= "HBc 1-20, an HTL-inducing
                peptide specific for HBV"

(xi) SEQUENCE DESCRIPTION: SEQ ID NO:100:

Met Asp Ile Asp Pro Tyr Lys Glu Phe Gly Ala Thr Val Glu Leu Leu
1               5                   10                  15

Ser Phe Leu Pro
            20

(2) INFORMATION FOR SEQ ID NO:101:

(i) SEQUENCE CHARACTERISTICS:
            (A) LENGTH: 20 amino acids
            (B) TYPE: amino acid
            (C) STRANDEDNESS: unknown
            (D) TOPOLOGY: unknown (ii) MOLECULE TYPE: peptide (ix) FEATURE:
            (A) NAME/KEY: Peptide
            (B) LOCATION: 1..20
            (D) OTHER INFORMATION: /note= "HTL-inducing peptide
                specific for HBV; HBc50-69"

(xi) SEQUENCE DESCRIPTION: SEQ ID NO:101:

Pro His His Tyr Ala Leu Arg Gln Ala Ile Leu Cys Trp Gly Glu Leu
1               5                   10                  15

Met Tyr Leu Ala
            20

(2) INFORMATION FOR SEQ ID NO:102:

(i) SEQUENCE CHARACTERISTICS:
            (A) LENGTH: 20 amino acids
            (B) TYPE: amino acid
            (C) STRANDEDNESS: unknown
            (D) TOPOLOGY: unknown (ii) MOLECULE TYPE: peptide (ix) FEATURE:
            (A) NAME/KEY: Peptide
            (B) LOCATION: 1..20
            (D) OTHER INFORMATION: /note= "HTL-inducing peptide
                specific for HBV; HBc100-119"

(xi) SEQUENCE DESCRIPTION: SEQ ID NO:102:

Leu Leu Trp Phe His Ile Ser Cys Leu Thr Phe Gly Arg Glu Thr Val

```
                 1               5              10              15

Ile Glu Tyr Leu
             20

(2) INFORMATION FOR SEQ ID NO:103:

(i) SEQUENCE CHARACTERISTICS:
        (A) LENGTH: 15 amino acids
        (B) TYPE: amino acid
        (C) STRANDEDNESS: unknown
        (D) TOPOLOGY: unknown (ii) MOLECULE TYPE: peptide (ix) FEATURE:
        (A) NAME/KEY: Peptide
        (B) LOCATION: 1..15
        (D) OTHER INFORMATION: /note= "HTL-inducing peptide
            specific for HBV; HBc117-131"

(xi) SEQUENCE DESCRIPTION: SEQ ID NO:103:

Glu Tyr Leu Val Ser Phe Gly Val Trp Ile Arg Thr Pro Pro Ala
1               5                  10                  15

(2) INFORMATION FOR SEQ ID NO:104:

(i) SEQUENCE CHARACTERISTICS:
        (A) LENGTH: 20 amino acids
        (B) TYPE: amino acid
        (C) STRANDEDNESS: unknown
        (D) TOPOLOGY: unknown (ii) MOLECULE TYPE: peptide (ix) FEATURE:
        (A) NAME/KEY: Peptide
        (B) LOCATION: 1..20
        (D) OTHER INFORMATION: /note= "HTL-inducing peptide
            specific for HBV; HBc120-139"

(xi) SEQUENCE DESCRIPTION: SEQ ID NO:104:

Val Ser Phe Gly Val Trp Ile Arg Thr Pro Pro Ala Tyr Arg Pro Pro
1               5                  10                  15

Asn Ala Pro Ile
             20

(2) INFORMATION FOR SEQ ID NO:105:

(i) SEQUENCE CHARACTERISTICS:
        (A) LENGTH: 29 amino acids
        (B) TYPE: amino acid
        (C) STRANDEDNESS: unknown
        (D) TOPOLOGY: unknown (ii) MOLECULE TYPE: peptide (ix) FEATURE:
        (A) NAME/KEY: Modified-site
        (B) LOCATION: 1
        (D) OTHER INFORMATION: /note= "Lysine residue linked, via
            the alpha and epsilon amino groups, to palmitic
            acid; (PAM)2Lys "

(xi) SEQUENCE DESCRIPTION: SEQ ID NO:105:

Lys Ser Ser Ile Ser Gln Ala Val His Ala Ala His Ala Glu Ile Asn
1               5                  10                  15

Glu Ala Ala Ala Thr Tyr Gln Arg Thr Arg Ala Leu Val
             20                  25
```

(2) INFORMATION FOR SEQ ID NO:106:

(i) SEQUENCE CHARACTERISTICS:
        (A) LENGTH: 9 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:106:

Gly Leu Tyr Ser Ser Thr Val Pro Val
1               5

(2) INFORMATION FOR SEQ ID NO:107:

(i) SEQUENCE CHARACTERISTICS:
        (A) LENGTH: 9 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:107:

Asn Leu Ser Trp Leu Ser Leu Asp Val
1               5

(2) INFORMATION FOR SEQ ID NO:108:

(i) SEQUENCE CHARACTERISTICS:
        (A) LENGTH: 9 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:108:

His Leu Tyr Ser His Pro Ile Ile Leu
1               5

(2) INFORMATION FOR SEQ ID NO:109:

(i) SEQUENCE CHARACTERISTICS:
        (A) LENGTH: 13 amino acids
        (B) TYPE: amino acid
        (C) STRANDEDNESS: unknown
        (D) TOPOLOGY: unknown (ii) MOLECULE TYPE: peptide (ix) FEATURE:
        (A) NAME/KEY: Modified-site
        (B) LOCATION: 1
        (D) OTHER INFORMATION: /note= "Lysine residue linked, via
            the alpha and epsilon amino groups, to palmitic
            acid; (PAM)2Lys "

(xi) SEQUENCE DESCRIPTION: SEQ ID NO:109:

Lys Ser Ser Phe Leu Pro Ser Asp Phe Phe Pro Ser Val
1               5                   10

(2) INFORMATION FOR SEQ ID NO:110:

(i) SEQUENCE CHARACTERISTICS:
        (A) LENGTH: 24 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:110:

Gln Tyr Ile Lys Ala Asn Ser Lys Phe Ile Gly Ile Thr Glu Phe Leu
1               5                   10                  15

Pro Ser Asp Phe Phe Pro Ser Val
            20

(2) INFORMATION FOR SEQ ID NO:111:

(i) SEQUENCE CHARACTERISTICS:
           (A) LENGTH: 27 amino acids
           (B) TYPE: amino acid
           (C) STRANDEDNESS: unknown
           (D) TOPOLOGY: unknown (ii) MOLECULE TYPE: peptide (xi) SEQUENCE DESCRIPTION: SEQ ID NO:111:

Gln Tyr Ile Lys Ala Asn Ser Lys Phe Ile Gly Ile Thr Glu Ala Ala
1               5                   10                  15

Ala Phe Leu Pro Ser Asp Phe Phe Pro Ser Val
            20                  25

(2) INFORMATION FOR SEQ ID NO:112:

(i) SEQUENCE CHARACTERISTICS:
           (A) LENGTH: 27 amino acids
           (B) TYPE: amino acid
           (C) STRANDEDNESS: unknown
           (D) TOPOLOGY: unknown (ii) MOLECULE TYPE: peptide (ix) FEATURE:
           (A) NAME/KEY: Modified-site
           (B) LOCATION: 1
           (D) OTHER INFORMATION: /note= "acetylated glutamine"

(xi) SEQUENCE DESCRIPTION: SEQ ID NO:112:

Gln Tyr Ile Lys Ala Asn Ser Lys Phe Ile Gly Ile Thr Glu Ala Ala
1               5                   10                  15

Ala Phe Leu Pro Ser Asp Phe Phe Pro Ser Val
            20                  25

(2) INFORMATION FOR SEQ ID NO:113:

(i) SEQUENCE CHARACTERISTICS:
           (A) LENGTH: 13 amino acids
           (B) TYPE: amino acid
           (C) STRANDEDNESS: unknown
           (D) TOPOLOGY: unknown (ii) MOLECULE TYPE: peptide (xi) SEQUENCE DESCRIPTION: SEQ ID NO:113:

Thr Pro Pro Ala Tyr Arg Pro Pro Asn Ala Pro Ile Leu
1               5                   10

(2) INFORMATION FOR SEQ ID NO:114:

(i) SEQUENCE CHARACTERISTICS:
           (A) LENGTH: 23 amino acids
           (B) TYPE: amino acid
           (C) STRANDEDNESS: unknown
           (D) TOPOLOGY: unknown (ii) MOLECULE TYPE: peptide

```
    (ix) FEATURE:
         (A) NAME/KEY: Modified-site
         (B) LOCATION: 23
         (D) OTHER INFORMATION: /note= "Valinamide"

(xi) SEQUENCE DESCRIPTION: SEQ ID NO:114:

Thr Pro Pro Ala Tyr Arg Pro Pro Asn Ala Pro Ile Leu Phe Leu Pro
1               5                   10                  15

Ser Asp Phe Phe Pro Ser Val
            20

(2) INFORMATION FOR SEQ ID NO:115:

(i) SEQUENCE CHARACTERISTICS:
         (A) LENGTH: 26 amino acids
         (B) TYPE: amino acid
         (C) STRANDEDNESS: unknown
         (D) TOPOLOGY: unknown (ii) MOLECULE TYPE: peptide (ix) FEATURE:
         (A) NAME/KEY: Modified-site
         (B) LOCATION: 26
         (D) OTHER INFORMATION: /note= "Valinamide"

(xi) SEQUENCE DESCRIPTION: SEQ ID NO:115:

Thr Pro Pro Ala Tyr Arg Pro Pro Asn Ala Pro Ile Leu Ala Ala Ala
1               5                   10                  15

Phe Leu Pro Ser Asp Phe Phe Pro Ser Val
            20                  25

(2) INFORMATION FOR SEQ ID NO:116:

(i) SEQUENCE CHARACTERISTICS:
         (A) LENGTH: 9 amino acids
         (B) TYPE: amino acid
         (C) STRANDEDNESS: unknown
         (D) TOPOLOGY: unknown (ii) MOLECULE TYPE: peptide (xi) SEQUENCE DESCRIPTION: SEQ ID NO:116:

Thr Tyr Gln Arg Thr Arg Ala Leu Val
1               5

(2) INFORMATION FOR SEQ ID NO:117:

(i) SEQUENCE CHARACTERISTICS:
         (A) LENGTH: 12 amino acids
         (B) TYPE: amino acid
         (C) STRANDEDNESS: unknown
         (D) TOPOLOGY: unknown (ii) MOLECULE TYPE: peptide (ix) FEATURE:
         (A) NAME/KEY: Modified-site
         (B) LOCATION: 1
         (D) OTHER INFORMATION: /note= "Lysine residue linked, via
             the alpha and epsilon amino groups, to palmitic
             acid; (PAM)2Lys "

(xi) SEQUENCE DESCRIPTION: SEQ ID NO:117:

Lys Ser Ser Thr Tyr Gln Arg Thr Arg Ala Leu Val
1               5                   10

(2) INFORMATION FOR SEQ ID NO:118:
```

```
    (i) SEQUENCE CHARACTERISTICS:
        (A) LENGTH: 23 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:118:

Thr Tyr Gln Arg Thr Arg Ala Leu Val Ile Ser Gln Ala Val His Ala
1               5                   10                  15

Ala His Ala Glu Ile Asn Glu
            20

(2) INFORMATION FOR SEQ ID NO:119:

(i) SEQUENCE CHARACTERISTICS:
        (A) LENGTH: 26 amino acids
        (B) TYPE: amino acid
        (C) STRANDEDNESS: unknown
        (D) TOPOLOGY: unknown (ii) MOLECULE TYPE: peptide (ix) FEATURE:
        (A) NAME/KEY: Modified-site
        (B) LOCATION: 1
        (D) OTHER INFORMATION: /note= "Lysine residue linked, via
            the alpha and epsilon amino groups, to palmitic
            acid; (PAM)2Lys "

(xi) SEQUENCE DESCRIPTION: SEQ ID NO:119:

Lys Ser Ser Thr Tyr Gln Arg Thr Arg Ala Leu Val Ile Ser Gln Ala
1               5                   10                  15

Val His Ala Ala His Ala Glu Ile Asn Glu
            20                  25

(2) INFORMATION FOR SEQ ID NO:120:

(i) SEQUENCE CHARACTERISTICS:
        (A) LENGTH: 23 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:120:

Ile Ser Gln Ala Val His Ala Ala His Ala Glu Ile Asn Glu Thr Tyr
1               5                   10                  15

Gln Arg Thr Arg Ala Leu Val
            20

(2) INFORMATION FOR SEQ ID NO:121:

(i) SEQUENCE CHARACTERISTICS:
        (A) LENGTH: 26 amino acids
        (B) TYPE: amino acid
        (C) STRANDEDNESS: unknown
        (D) TOPOLOGY: unknown (ii) MOLECULE TYPE: peptide (ix) FEATURE:
        (A) NAME/KEY: Modified-site
        (B) LOCATION: 1
        (D) OTHER INFORMATION: /note= "Lysine residue linked, via
            the alpha and epsilon amino groups, to palmitic
            acid; (PAM)2Lys "
```

(xi) SEQUENCE DESCRIPTION: SEQ ID NO:121:

Lys Ser Ser Ile Ser Gln Ala Val His Ala Ala His Ala Glu Ile Asn
1               5                   10                  15

Glu Thr Tyr Gln Arg Thr Arg Ala Leu Val
                20                  25

(2) INFORMATION FOR SEQ ID NO:122:

(i) SEQUENCE CHARACTERISTICS:
        (A) LENGTH: 26 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:122:

Ile Ser Gln Ala Val His Ala Ala His Ala Glu Ile Asn Glu Ala Ala
1               5                   10                  15

Ala Thr Tyr Gln Arg Thr Arg Ala Leu Val
                20                  25

(2) INFORMATION FOR SEQ ID NO:123:

(i) SEQUENCE CHARACTERISTICS:
        (A) LENGTH: 17 amino acids
        (B) TYPE: amino acid
        (C) STRANDEDNESS: unknown
        (D) TOPOLOGY: unknown (ii) MOLECULE TYPE: peptide (ix) FEATURE:
        (A) NAME/KEY: Modified-site
        (B) LOCATION: 1
        (D) OTHER INFORMATION: /note= "Lysine residue linked, via
            the alpha and epsilon amino groups, to palmitic
            acid; (PAM)2Lys "

(xi) SEQUENCE DESCRIPTION: SEQ ID NO:123:

Lys Ser Ser Ile Ser Gln Ala Val His Ala Ala His Ala Glu Ile Asn
1               5                   10                  15

Glu (2) INFORMATION FOR SEQ ID NO:124:

(i) SEQUENCE CHARACTERISTICS:
        (A) LENGTH: 26 amino acids
        (B) TYPE: amino acid
        (C) STRANDEDNESS: unknown
        (D) TOPOLOGY: unknown (ii) MOLECULE TYPE: peptide (ix) FEATURE:
        (A) NAME/KEY: Modified-site
        (B) LOCATION: 1
        (D) OTHER INFORMATION: /note= "Lysine residue linked, via
            the alpha and epsilon amino groups, to palmitic
            acid; (PAM)2Lys "

(xi) SEQUENCE DESCRIPTION: SEQ ID NO:124:

Lys Ser Ser Ile Ser Gln Ala Val His Ala Ala His Ala Glu Ile Asn
1               5                   10                  15

Glu Thr Tyr Gln Arg Thr Arg Ala Leu Val
                20                  25

(2) INFORMATION FOR SEQ ID NO:125:

(i) SEQUENCE CHARACTERISTICS:
        (A) LENGTH: 10 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:125:

Leu Leu Phe Asn Ile Leu Gly Gly Trp Val
1               5                   10

(2) INFORMATION FOR SEQ ID NO:126:

(i) SEQUENCE CHARACTERISTICS:
        (A) LENGTH: 10 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:126:

Leu Leu Ala Leu Leu Ser Cys Leu Thr Val
1               5                   10

(2) INFORMATION FOR SEQ ID NO:127:

(i) SEQUENCE CHARACTERISTICS:
        (A) LENGTH: 9 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:127:

Tyr Leu Val Ala Tyr Gln Ala Thr Val
1               5

(2) INFORMATION FOR SEQ ID NO:128:

(i) SEQUENCE CHARACTERISTICS:
        (A) LENGTH: 9 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:128:

Phe Leu Leu Leu Ala Asp Ala Arg Val
1               5

(2) INFORMATION FOR SEQ ID NO:129:

(i) SEQUENCE CHARACTERISTICS:
        (A) LENGTH: 9 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:129:

Ile Leu Ala Gly Tyr Gly Ala Gly Val
1               5

(2) INFORMATION FOR SEQ ID NO:130:

(i) SEQUENCE CHARACTERISTICS:
        (A) LENGTH: 9 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:130:

Asp Leu Met Gly Tyr Ile Pro Leu Val
1               5

(2) INFORMATION FOR SEQ ID NO:131:

(i) SEQUENCE CHARACTERISTICS:
        (A) LENGTH: 10 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:131:

Tyr Leu Leu Pro Arg Arg Gly Pro Arg Leu
1               5                   10

(2) INFORMATION FOR SEQ ID NO:132:

(i) SEQUENCE CHARACTERISTICS:
        (A) LENGTH: 9 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:132:

Ala Leu Ser Thr Gly Leu Ile His Leu
1               5

(2) INFORMATION FOR SEQ ID NO:133:

(i) SEQUENCE CHARACTERISTICS:
        (A) LENGTH: 10 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:133:

Leu Leu Ala Leu Leu Ser Cys Leu Thr Ile
1               5                   10

(2) INFORMATION FOR SEQ ID NO:134:

(i) SEQUENCE CHARACTERISTICS:
        (A) LENGTH: 10 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:134:

Arg Leu Ile Val Phe Pro Asp Leu Gly Val

```
1               5                   10
```

(2) INFORMATION FOR SEQ ID NO:135:

(i) SEQUENCE CHARACTERISTICS:
        (A) LENGTH: 10 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:135:

```
Arg Leu His Gly Leu Ser Ala Phe Ser Leu
1               5                   10
```

(2) INFORMATION FOR SEQ ID NO:136:

(i) SEQUENCE CHARACTERISTICS:
        (A) LENGTH: 10 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:136:

```
Ile Leu Gly Gly Trp Val Ala Ala Gln Leu
1               5                   10
```

(2) INFORMATION FOR SEQ ID NO:137:

(i) SEQUENCE CHARACTERISTICS:
        (A) LENGTH: 9 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:137:

```
Ser Met Val Gly Asn Trp Ala Lys Val
1               5
```

(2) INFORMATION FOR SEQ ID NO:138:

(i) SEQUENCE CHARACTERISTICS:
        (A) LENGTH: 9 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:138:

```
Tyr Leu Val Thr Arg His Ala Asp Val
1               5
```

(2) INFORMATION FOR SEQ ID NO:139:

(i) SEQUENCE CHARACTERISTICS:
        (A) LENGTH: 10 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:139:

```
Val Leu Ala Ala Leu Ala Ala Tyr Cys Leu
1               5                   10
```

(2) INFORMATION FOR SEQ ID NO:140:

(i) SEQUENCE CHARACTERISTICS:
        (A) LENGTH: 9 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:140:

```
Lys Met Val Glu Leu Val His Phe Leu
1               5
```

(2) INFORMATION FOR SEQ ID NO:141:

(i) SEQUENCE CHARACTERISTICS:
        (A) LENGTH: 10 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:141:

```
Lys Met Val Glu Leu Val His Phe Leu Leu
1               5                   10
```

(2) INFORMATION FOR SEQ ID NO:142:

(i) SEQUENCE CHARACTERISTICS:
        (A) LENGTH: 10 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:142:

```
Leu Val Phe Gly Ile Glu Leu Met Glu Val
1               5                   10
```

(2) INFORMATION FOR SEQ ID NO:143:

(i) SEQUENCE CHARACTERISTICS:
        (A) LENGTH: 9 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:143:

```
Lys Val Leu Glu Tyr Val Ile Lys Val
1               5
```

(2) INFORMATION FOR SEQ ID NO:144:

(i) SEQUENCE CHARACTERISTICS:
        (A) LENGTH: 10 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:144:

```
Lys Val Ala Asp Leu Val Gly Phe Leu Leu
1               5                   10
```

(2) INFORMATION FOR SEQ ID NO:145:

(i) SEQUENCE CHARACTERISTICS:
        (A) LENGTH: 9 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:145:

```
Lys Val Ala Glu Phe Val His Phe Leu
1               5
```

(2) INFORMATION FOR SEQ ID NO:146:

(i) SEQUENCE CHARACTERISTICS:
        (A) LENGTH: 9 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:146:

```
Cys Ile Leu Glu Ser Leu Phe Arg Ala
1               5
```

(2) INFORMATION FOR SEQ ID NO:147:

(i) SEQUENCE CHARACTERISTICS:
        (A) LENGTH: 9 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:147:

```
Phe Leu Trp Gly Pro Arg Ala Leu Ala
1               5
```

(2) INFORMATION FOR SEQ ID NO:148:

(i) SEQUENCE CHARACTERISTICS:
        (A) LENGTH: 10 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:148:

```
Val Met Ile Ala Met Glu Gly Gly His Ala
1               5                   10
```

(2) INFORMATION FOR SEQ ID NO:149:

(i) SEQUENCE CHARACTERISTICS:
        (A) LENGTH: 9 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:149:

Leu Val Leu Gly Thr Leu Glu Glu Val
1               5

(2) INFORMATION FOR SEQ ID NO:150:

(i) SEQUENCE CHARACTERISTICS:
        (A) LENGTH: 9 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:150:

Ala Leu Arg Glu Glu Glu Glu Gly Val
1               5

(2) INFORMATION FOR SEQ ID NO:151:

(i) SEQUENCE CHARACTERISTICS:
        (A) LENGTH: 10 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:151:

Ala Leu Ala Glu Thr Ser Tyr Val Lys Val
1               5                   10

(2) INFORMATION FOR SEQ ID NO:152:

(i) SEQUENCE CHARACTERISTICS:
        (A) LENGTH: 9 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:152:

Tyr Val Ile Lys Val Ser Ala Arg Val
1               5

(2) INFORMATION FOR SEQ ID NO:153:

(i) SEQUENCE CHARACTERISTICS:
        (A) LENGTH: 9 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:153:

Arg Ala Leu Ala Glu Thr Ser Tyr Val
1               5

US 6,419,931 B1

COMPOSITIONS AND METHODS FOR ELICITING CTL IMMUNITY

RELATED APPLICATIONS

The present application is a continuation-in-part of U.S. Ser. No. 07/935,811, filed Aug. 26, 1992, abandoned, which is a continuation-in-part of U.S. Ser. No. 07/874,491, filed Apr. 27, 1992 and now abandoned, which is a continuation-in-part of U.S. Ser. No. 07/827,682, filed Jan. 29, 1992 and now abandoned, which is a continuation-in-part of U.S. Ser. No. 07/749,568, filed Aug. 26, 1991 and now abandoned, each of which is incorporated herein by reference.

The invention may have been made with government support under a contract with the National Institutes of Health and/or the National Institute of Allergy and Infectious Disease. Therefore, the government may have certain rights in the invention.

BACKGROUND OF THE INVENTION

Cytotoxic T lymphocytes ("CTL") represent an important component of an animal's immune response against a variety of pathogens and cancers. CTL which have been specifically activated against a particular antigen are capable of killing the cell that contains or expresses the antigen. CTL are particularly important in providing an effective immune response against intracellular pathogens, such as a wide variety of viruses, and some bacteria and parasites. CTL responses are also believed to be capable of contributing to anti-tumor responses in afflicted or susceptible individuals.

The receptors on the surface of the CTL cannot recognize a foreign antigen directly, however. The CTL express an α-β heterodimeric T cell receptor which is capable of recognizing foreign antigen fragments bound to major histocompatibility complex (MHC) class I molecules on the surface of the effected (e.g., infected) cells. CTL also express the non-polymorphic CD8 antigen. This cell surface protein interacts with the third domain of the class I molecule on the antigen presenting cells and plays a role in both stabilizing the interaction between the CTL and the antigen presenting cell and in CTL activation (Salter et al., Nature 345:41–46 (1990)).

There are a number of mechanisms by which CTL are thought to disrupt the infectious or tumorigenic process. Among these, one involves the production of lymphokines such as gamma interferon (IFNγ) and tumor necrosis factor alpha (TNFa), which are known to act directly on infected cells to inhibit viral replication (Gilles et al., J. Virol. 66:3955–3960 (1992)). In addition, IFNγ causes increased expression of MHC class I molecules on the surface of virus infected cells and enhances their ability to be recognized by CTL and trigger immune intervention (Hayata et al., Hepatology 13:1022–1028 (1991)).

A second mechanism by which CTL combat infections or tumors is through direct killing of the afflicted cell, e.g., those which are infected by the targeted virus (Cohen et al., Ann. Rev. Immunol. 10:267–293 (1992) and Henkart et al., Ann. Rev. Immunol. 3:31–58 (1985)). For example, since viruses must replicate within the host cell the lysis of infected cells destroys virus production prior to the liberation of infectious particles. The exact mechanism(s) by which CTL kill infected target cells remains unclear. Once CTL recognized an antigen presenting cell, close contact between the cells is established over a large surface area. A "direct hit" is then delivered by translocating enzymes present in cytoplasmic vacuoles of CTL to the antigen presenting cell, which enzymes kill the cell or perhaps induce programmed cell death, "apoptosis". Once CTL have delivered their "lethal hit" to the antigen presenting cells, they can detach and go on to kill other antigen presenting cells through repetition of the antigen-specific recognition, lymphokine release and target cell killing mechanisms.

The means by which CTL distinguish infected from non-infected cells is through the T cell receptor and its ability to specifically recognize a peptide fragment of viral protein that is bound to the peptide-binding cleft of the MHC class I molecule (Monaco et al., Immunol. Today 13:173–179 (1992) and Townsend et al., Ann. Rev. Immunol. 7:601–624 (1989)). Several viral fragments that can serve an antigenic peptides have been identified.

The biochemical events that take place in the cytoplasm of infected cells leading to CTL recognition are termed antigen processing and presentation. While not completely defined, it seems clear that during the synthesis and assembly of the infecting viral or bacterial proteins, some proteolysis takes place in the cytoplasm (Monaco et al., Immunol. Today 13:173–179 (1992)). Structures called proteosomes cleave the foreign proteins into peptide fragments. These fragments are then transported into the endoplasmic reticulum (ER) by means of specific transporter proteins where newly synthesized MHC class I molecules are present. Those peptides that are capable of specifically binding to a given MHC class I molecule do so in the ER. The non-polymorphic class I β chain, $β_2$ microglobulin binds to the antigenic peptide-class I complex, thus forming a stable trimolecular complex that is transported to the cell surface and displayed as an integral membrane component.

The selection of which peptides bind to a particular MHC class I molecule is based on the ability of the peptide to bind within the binding pocket or cleft which resides at the outermost apex of the extra-cellular portion of the MHC molecule. For several MHC molecules, this peptide binding pocket has been precisely defined by X-ray crystallographic procedures allowing a visualization of the types and location of the chemical bonds that form to stabilize the interaction (Saper et al., J. Mol. Biol. 219:277–319 (1991)).

Because of the differences in the structure of the peptide binding pocket between the diverse set of histocompatibility alleles, e.g., the human HLA alleles, a distinct population of antigenic peptides is bound by each allele, although in some cases the population of antigenic peptides may overlap for closely related alleles. Thus, the specificity of the CTL for a foreign antigen resides at the level of the ability of MHC class I molecules to bind to a specific peptide as well as for the T cell receptor on the CTL to recognize the foreign protein fragment bound to that specific MHC class I allele.

In animals, CT8+, MHC class I-restricted cytotoxic T cells play an important role in the immune mediated clearance of viral infections (e.g., Oldstone et al., Nature 321:239–243 (1986); Mackenzie et al., Immunol. 67:375 (1989); and Robertson et al., J. Virol. 66:3271–3277 (1992)). While similar studies have not been possible in humans, and thus direct proof is still lacking, all of the evidence points to a similar role for CTL.

The importance of CTL in viral clearance in animals is evidenced by lymphocytic choriomeningitis virus (LCMV) infection in mice (Oldstone et al., Nature 321:239–243 (1986); Mackenzie et al., Immunol. 67:375 (1989); Robertson et al., J. Virol. 66:3271–3277 (1992); and Ahmed et al., J. Virol. 61:3920–3929 (1987)). When LCMV infects newborns or immune-suppressed adult animals, they become chronically infected and virus is expressed in nearly all tissues of the body. In contrast, adult mice infected with LCMV mount a vigorous cellular and humoral response against the virus and clear the infection within one to two weeks. When chronic carriers of LCMV are adoptively treated by transfer of CD8+LCMV-specific, MHC class I-restricted CTL, the viral infection is cleared and the mice become resistant to subsequent LCMV challenge. Additional studies have shown that CTL are necessary and sufficient for LCMV clearance and that other aspects of the immune system need not be functioning (Oldstone et al., Nature 321:239–243 (1986) and Schulz et al. Proc. Natl. Acad. Sci. USA 88:991–993 (1991)).

In addition to mediating the clearance of virus from chronically infected animals, studies have demonstrated that CTL generated in vivo against a synthetic peptide which presents an antigenic epitope of LCMV are able to protect mice against acute infection (Schulz et al., Proc. Natl. Acad. Sci. USA 88:991–993 (1991)). Mice injected with 100 µg of a synthetic 15 amino acid peptide in complete Freund's adjuvant were fully protected from a lethal LCMV challenge.

With regard to the role of CTL in other viral infections, studies with influenza virus and respiratory syncytial virus in mice have similarly demonstrated the importance of CTL activation in the rapid and effective recovery from these infections.

Strong evidence from animal studies indicates that an acute infection can become chronic when there is an inadequate immune response to clear the infection (Ahmed, Concepts in Viral Pathogenesis III, Notkins and Oldstone eds., Springer-Verlag, New York, 304–310 (1989)). Once the chronic infection has been established, it appears to be more or less "tolerated" by the host's immune system. Tolerance appears to be organism-specific rather than a result of general immunosuppression (Fields et al., Fields Virology, Raven Press, New York, N.Y. 2:2137–2236 (1990)). Studies examining which cells in the immune system are anergic or tolerant to the infecting organism suggest that the CD4+, class II-restricted T "helper" cells are dysfunctional (Schwartz, Cell 57:1073–1081 (1989)). Since class II-restricted T helper cells play a critical role in the initial priming of class I-restricted CTL (Cassell et al., Ann. NY Acad. Sci. 532:51–60 (1988) and Fayolle et al., J. Immunol. 174:4069 (1991)), diminished CD4 cell function may impair the capacity of the immune system to respond adequately, and may thus clear the way for chronic infection.

Decreased T helper cell activity has been shown in the case of chronic hepatitis B infection in humans, although the fact that some CD4+ T helper function is seen suggests that these cells are not completely dysfunctional (see, e.g., Ahmed et al., J. Virol. 61:3920–3929 (1987); Alberti et al., Lancet 1:1421–1424 (1988); Neurath et al., Nature 315:154–156 (1985); Celis et al., J. Immunol. 132:1511–1516 (1984); and Ferrari et al., J. Immunol. 139:2050–2055 (1987)). Class I-restricted CTL can be detected in patients with chronic HBV infection (Barnaba et al., J. Immunol. 143:2650–2654 (1989)).

The requirement for lymphokines such as IL-2 in the generation of CD8+ CTL is well established, although the need for activation of CD4+ T helper cells to provide these lymphokines remains somewhat controversial. While the concept of linked T helper-B cell recognition for antibody production has been firmly defined, there is no compelling evidence for linked T helper-CTL recognition for the in vivo induction of CD8+ CTL. See, e.g., Buller et al., Nature 328:77–79 (1987); Sarobe et al., Eur. J. Immunol. 21:1555–1558 (1991); and Cassell and Forman, Annals N.Y. Acad. Sci. 51–60 (1991).

Thus, the data available suggest that CD8+ class I-restricted cytotoxic T cells specific for foreign antigens such as viral proteins play a critical part in prevention of disease and clearance of an established disease process. Therefore, the challenge is to induce a sufficiently potent, antigen-specific, cell-mediated immune response in humans and other mammals which, by itself or in conjunction with chemotherapeutic agents or the like, will either prevent a disease process such as an infection or tumor from becoming established, or will eliminate or at least ameliorate an infection or tumor which has already become established in the host. Quite surprisingly, the present invention fulfills these and other related needs.

SUMMARY OF THE INVENTION

The present invention provides compositions for inducing a cytotoxic T lymphocyte response to an antigen of interest in a mammal. The compositions comprise a peptide that induces a CTL response to the antigen and a peptide that induces a HTL response, wherein the HTL-inducing peptide is lipidated. The HTL-inducing peptide is optionally linked to the CTL-inducing peptide or not linked. When linked, the HTL-inducing peptide may be separated from the CTL peptide by a spacer, such as Ala-Ala-Ala. The HTL-inducing peptide will usually be linked at its C-terminal end to the CTL-inducing peptide. Typically, the lipid is linked to the N-terminus of the HTL-inducing peptide, where the linkage can optionally include a spacer, such as Lys-Ser-Ser or the like.

The antigen to which the cytotoxic T lymphocyte response is induced is selected from a viral, bacterial, parasitic or tumor antigen. Among the viral antigens to which the CTL responses are effectively induced are antigens of hepatitis B (such as envelope, core or polymerase antigens), hepatitis C or human papilloma virus. A particularly effective hepatitis B antigen is HBc18–27. Typically the CTL inducing peptide will be from seven to fifteen residues, and more usually from nine to eleven residues. The immunogenic composition can further comprise a carrier, such as physiologic saline, and an adjuvant, such as incomplete freunds adjuvant, alum or montanide. When the peptide is lipidated, it may be modified or unmodified. The lipid is preferably a linear alkyl chain of 6–22 carbons, and preferably is a linear alkyl chain of 16 carbons. In some embodiments of the present invention the lipid is comprised of palmitic acid attached to epsilon and alpha amino groups of a Lys residue, wherein the Lys is linked to the amino terminus of the HTL-inducing peptide by means of a linker.

In other embodiments the present invention comprises methods for inducing a cytotoxic T lymphocyte response in a mammal against an antigen such as a viral, bacterial, parasitic, or tumor antigen. The method comprises administering to the mammal a peptide that induces a CTL response to the antigen, and administering, either separately or together, a lipidated peptide that induces a HTL response. The HTL-inducing peptide is optionally linked to the CTL-inducing peptide or unlinked. When unlinked, the HTL-inducing peptide can be admixed with the CTL-inducing peptide. The HTL-inducing peptide and the CTL-inducing peptide are typically administered to the mammal in a regimen of two or more administrations. These boosters are spaced a sufficient interval apart to optimize development of a CTL response to the antigen of interest, e.g., a second administration may be approximately four weeks after the initial administration. In representative embodiments described herein the antigen is hepatitis B antigen, such as HBc18–27 and the mammal is a human, of the HLA-A2.1 histocompatibility type for the HBc18–27 CTL inducing peptide.

In yet other embodiments the invention provides methods for treating or preventing a disease that is susceptible to treatment by a CTL response by administering a CTL-inducing peptide to an antigen associated with said disease, and a HTL-inducing peptide conjugated to a lipid. The induction of a CTL response can be used in the treatment or prevention of viral infection (e.g., hepatitis B, hepatitis C or human papilloma virus), bacterial or parasitic infection or tumors. When the disease is hepatitis B infection, for example, the methods can be used to treat or prevent chronic or acute infection.

In yet other embodiments the invention provides methods for inducing a cytotoxic T lymphocyte response in a human against an antigen of interest. The methods comprise administering a composition which comprises a peptide that induces a CTL response to said antigen in a human and an adjuvant. The method may further comprise administering a peptide that induces a HTL response, and in some embodiments the HTL inducing peptide is linked to the CTL inducing peptide.

In other aspects the invention provides methods for inducing a CTL response in a human against an antigen of interest by administering a peptide that induces a CTL response to the antigen and a peptide that induces a HTL response, where the CTL inducing and/or the HTL inducing peptide is lipidated. The CTL and HTL inducing peptides may be linked or unlinked. The HTL inducing peptide is preferably lipidated. The lipidated HTL inducing peptide can be combined with a cocktail of at least two CTL inducing peptides to optimize coverage of individuals of different HLA types or, in some instances, different antigen strains.

In a further aspect of the invention methods are described for inducing an effective CTL response in a human against an antigen of interest. According to these methods one or more peptides that induce a CTL response to the antigen, such as a viral, bacterial, parasitic or tumor antigen, is administered to a human together or separately with a peptide that induces a HTL response, where at least the CTL inducing and/or the HTL inducing peptide is lipidated. In representative embodiments of such a method described herein the CTL response is induced to a viral antigen, such as hepatitis B antigen.

Pharmaceutical composition for the treatment of hepatitis B infection are also provided. These compositions comprise a peptide that induces a CTL response to hepatitis B and a peptide that induces a HTL response, where the HTL-inducing peptide is conjugated to a lipid, together with a pharmaceutically acceptable carrier. The carrier can be a liposome, for example, and the pharmaceutical composition may further comprises an adjuvant, such as incomplete Freund's adjuvant, alum or MONTANIDE® (Seppic, Paris, France; oil-based adjuvant with mannide oleate).

BRIEF DESCRIPTION OF THE DRAWINGS

FIG. 1A–1D: Splenocytes from HBV-primed transgenic mice were restimulated in vitro with four mixtures of syngeneic LPS blasts each coated with one of 13 different peptides. After 9 days effector cells were assayed for lytic activity against $^{51}$Cr labelled Jurkat A2.1/$K^b$ target cells in the presence or absence of the four different peptide mixtures used for induction. FIG. 1E–1H: Effector cells raised against the four different peptide mixtures were restimulated in vitro against the same peptide mixtures and assayed for lytic activity against $^{51}$Cr labelled Jurkat A2.1/$K^b$ target cells in the presence or absence of the individual peptides.

FIGS. 4A–4L collectively show the results obtained when the effector CTL of FIG. 3 were restimulated with peptide coated LPS blasts followed at a one week interval by restimulation with peptide coated Jurkat A2.1/$K^b$ cells. Six days after the last restimulation, effector cells were assayed for cytolytic activity against $^{51}$Cr labelled Jurkat A2.1/$K^b$ target cells in the absence or presence of the peptide used for the restimulation, plus related peptides. Each panel represents the CTL activity induced by the peptide indicated in the corresponding panel of FIG. 3. The target peptides are indicated in each panel.

FIG. 13B=799.09 overlapping 9 mers and 10 mers).

FIGS. 17A–17B show HBc18–27 specific CTL from subjects injected with CY-1899 recognize endogenous processed antigen. Effector CTL obtained from subjects 302 and 304 after 14 days of culture were restimulated as described in FIG. 2 CTL activity was assayed 7 days later as shown in FIG. 1 using as targets 0.221 A$_2$ cells in the absence (- -) or presence (-··-) of HBc18–27 peptide and 0.221 A$_2$ cells transfected with the HBV core protein (-Δ-).

DESCRIPTION OF THE SPECIFIC EMBODIMENTS

Figure 1A:
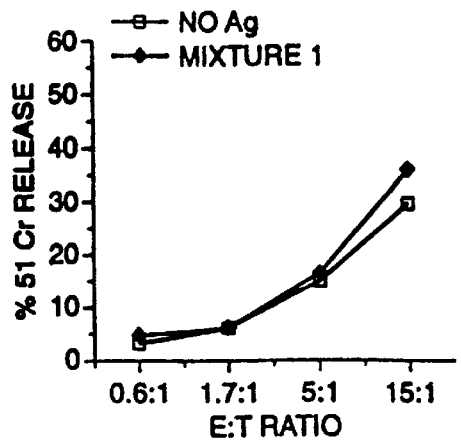
FIGS. 1A–1H depict the results of induction of HBV peptide-specific A2.1-restricted CTL by priming A2.1/$K^b$ transgenic mice with syngeneic spleen cells "loaded" with HBV.
Figure 1B:
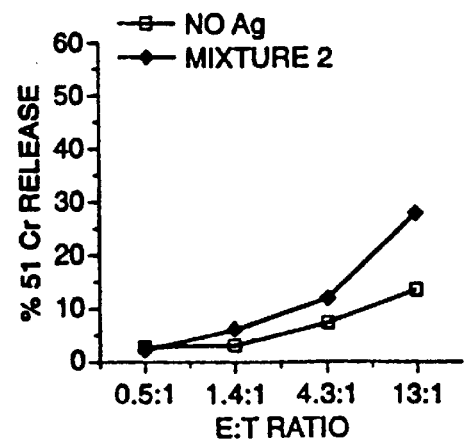
Figure 1C:
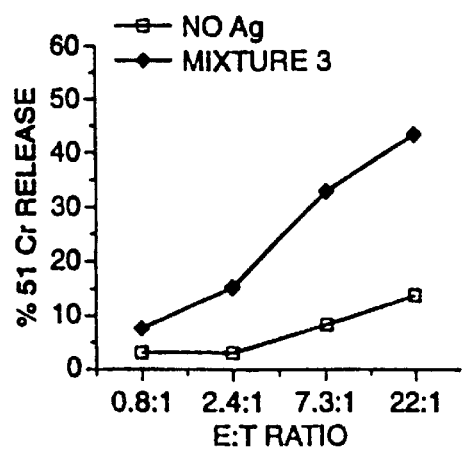
Figure 1D:
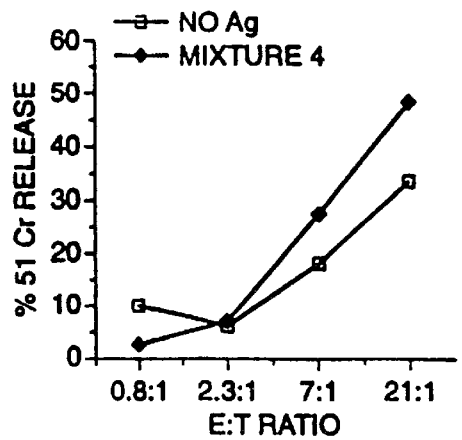
Figure 1E:
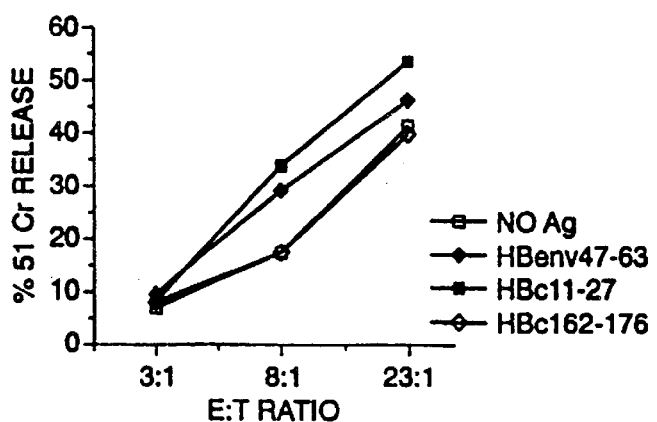
Figure 1F:
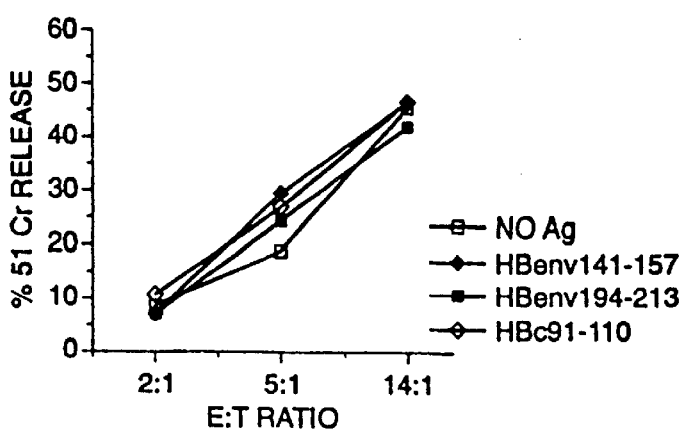
Figure 1G:
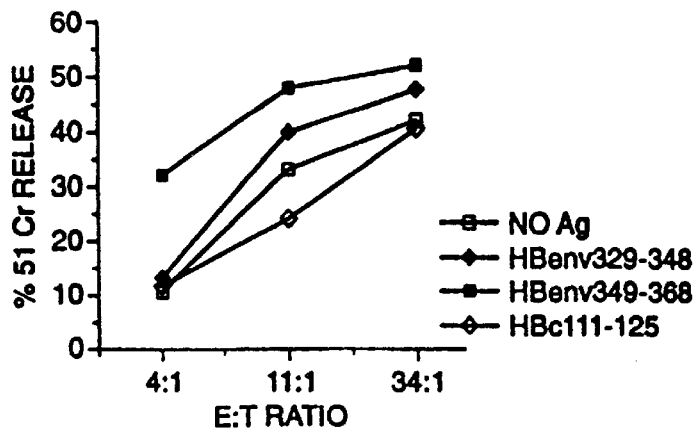
Figure 1H:
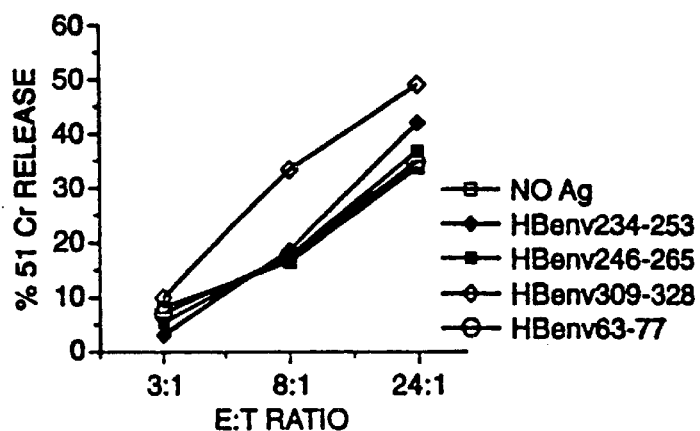
Figure 2I:
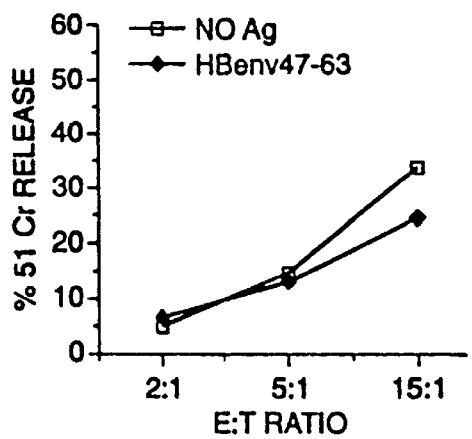
FIGS. 2I–2P collectively illustrate the HBV peptide specificity of A2.1 transgenic CTL. Transgenic CTL raised from HBV-primed transgenic mice and restimulated in vitro twice with one of the four different peptide mixtures were restimulated with individual HBV peptides and assayed for lytic activity on $^{51}$CR labelled Jurkat target cells in the presence or absence of the HBV peptides used for the restimulation.
Figure 2J:
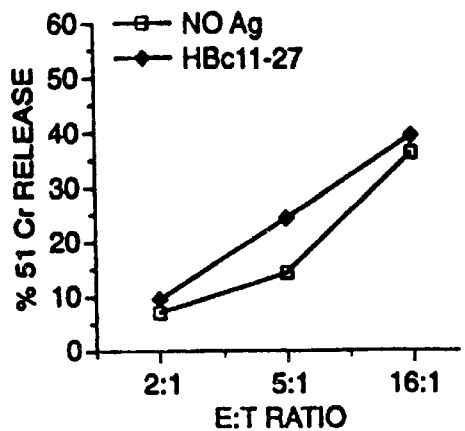
Figure 2K:
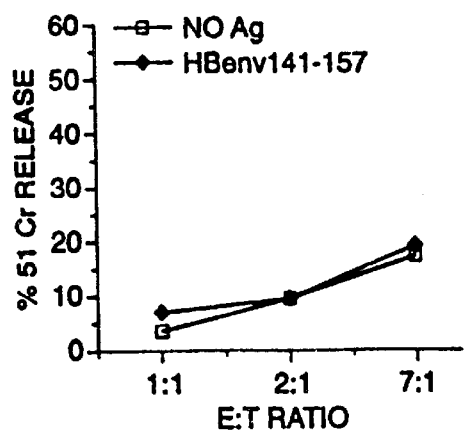
Figure 2L:
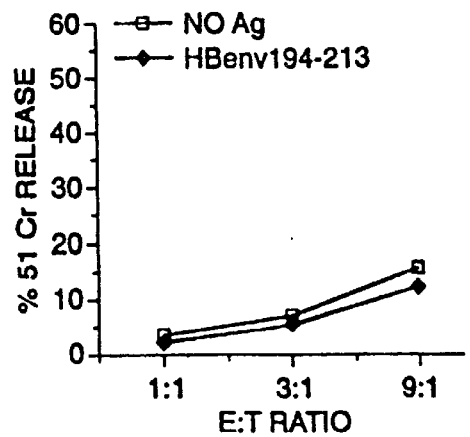
Figure 2M:
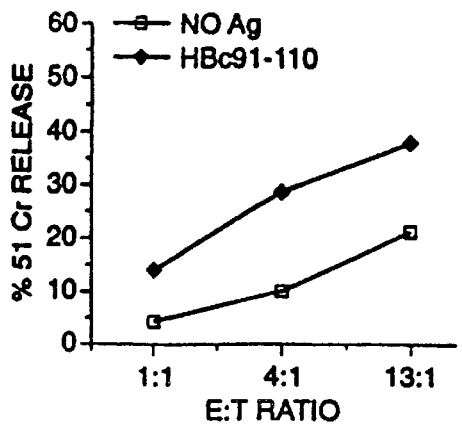
Figure 2N:
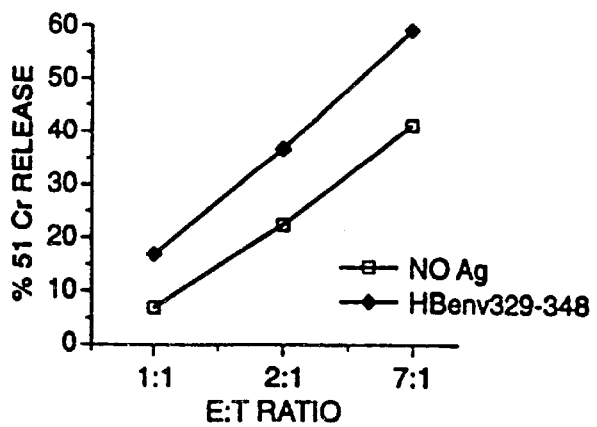
Figure 2O:
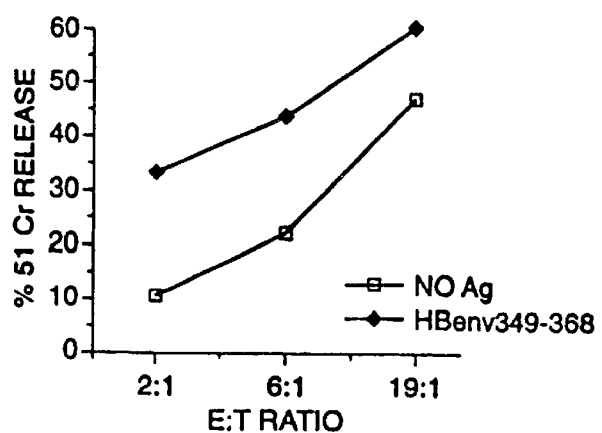
Figure 2P:
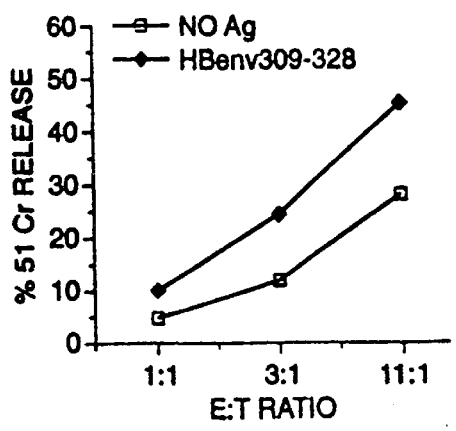
Figure 3A:
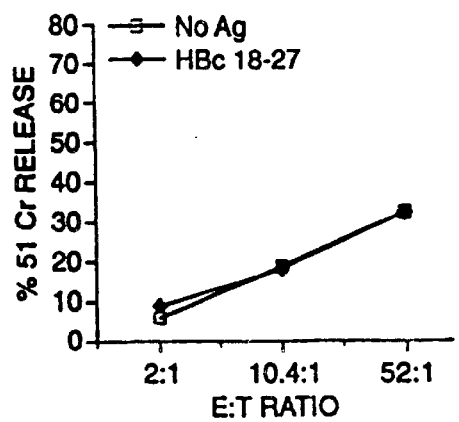
FIGS. 3A–3L collectively illustrate the results of induction of HBV peptide-specific A2.1-restricted CTL by priming A2.1/$K^b$ transgenic mice with HBV in IFA. A. Splenocytes from HBV-primed transgenic mice were restimulated in vitro with syngeneic LPS blasts coated with HBV peptides. After six days, effector cells were assayed for lytic activity against $^{51}$Cr labelled Jurkat A2.1/$K^b$ target cells in the presence or absence of the appropriate HBV peptide. Each panel represents the CTL activity induced by the indicated target peptide.
Figure 3B:
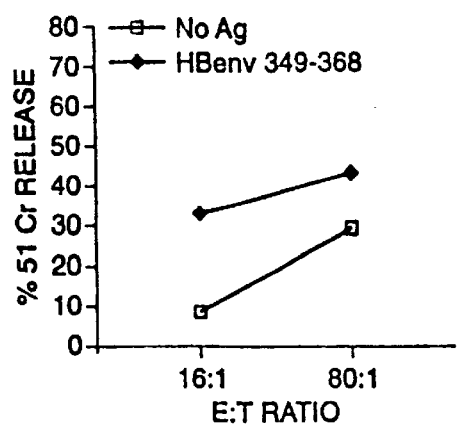
Figure 3C:
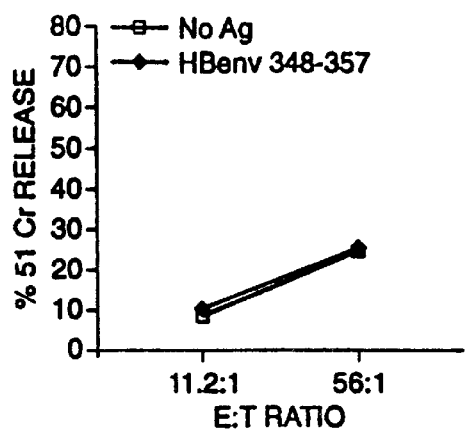
Figure 3D:
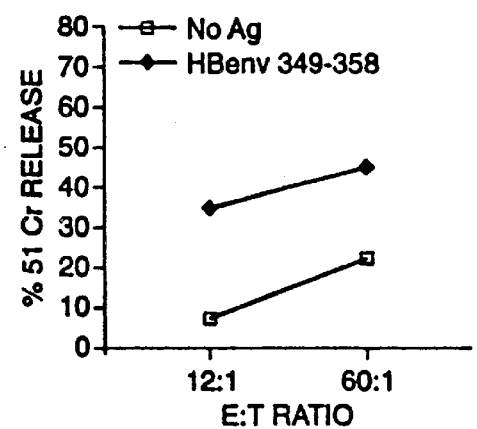
Figure 3E:
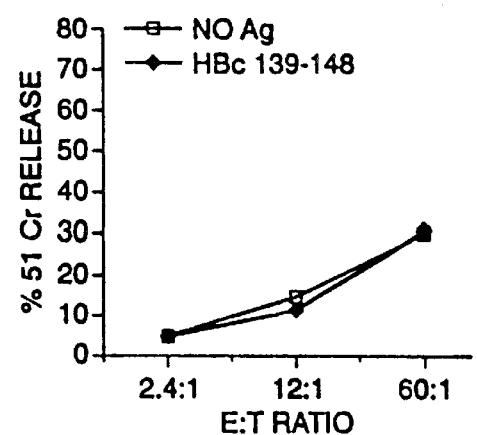
Figure 3F:
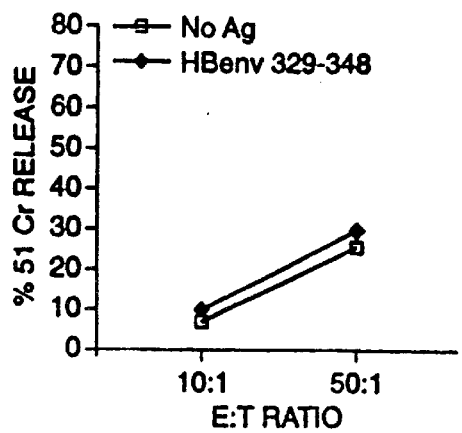
Figure 3G:
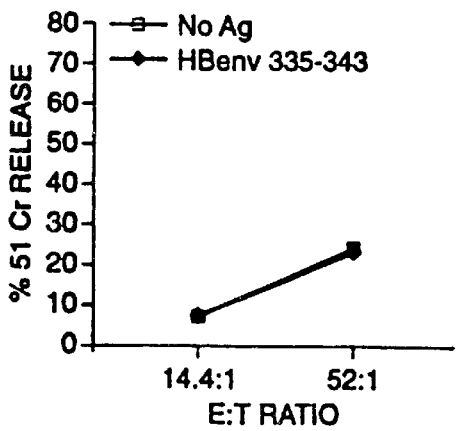
Figure 3H:
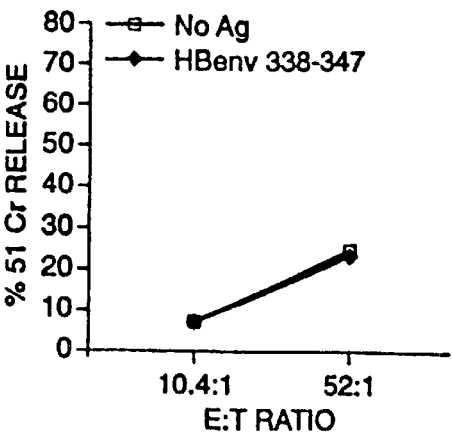
Figure 3I:
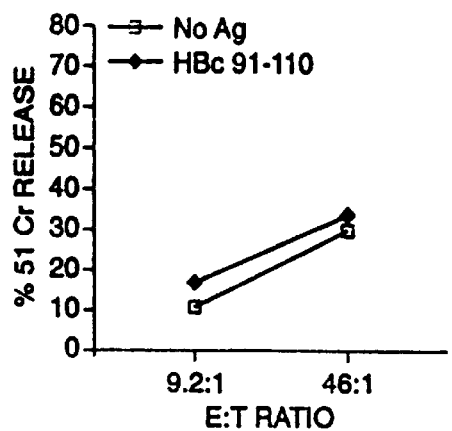
Figure 3J:
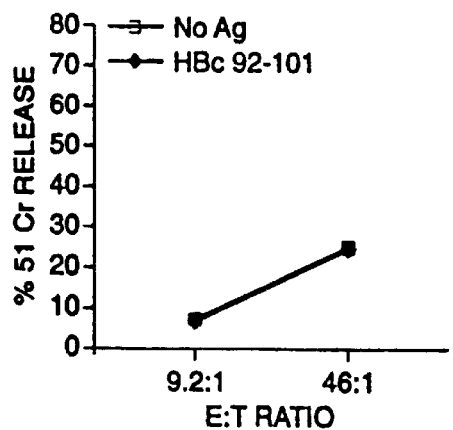
Figure 3K:
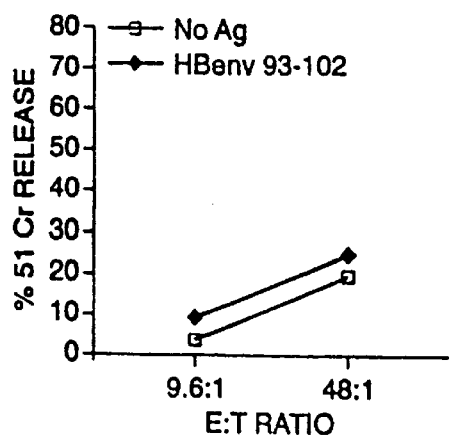
Figure 3L:
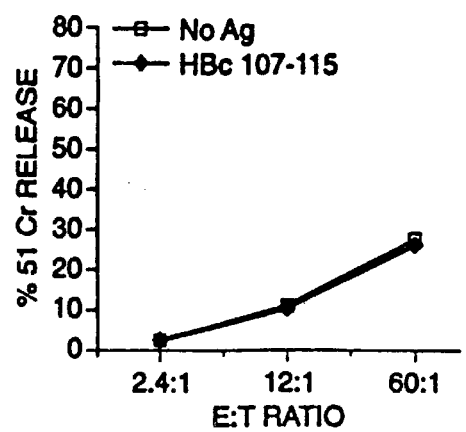
Figure 4A:
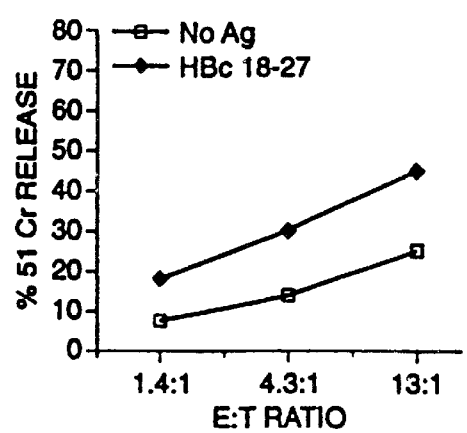
Figure 4B:
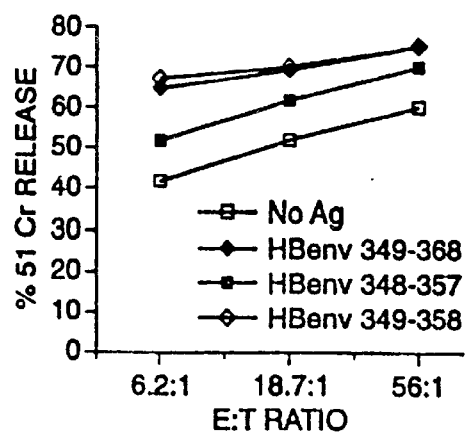
Figure 4C:
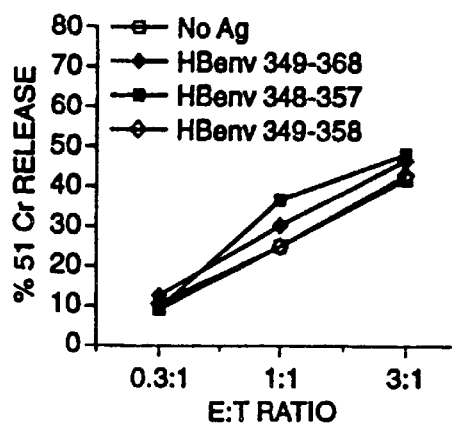
Figure 4D:
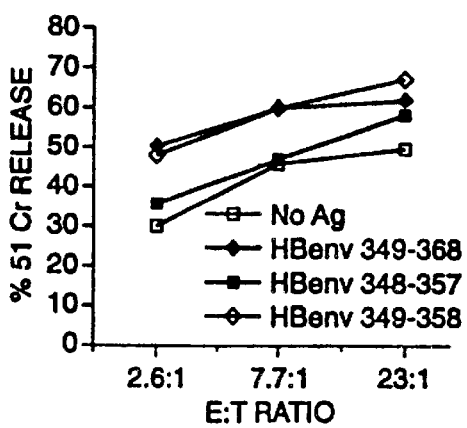
Figure 4E:
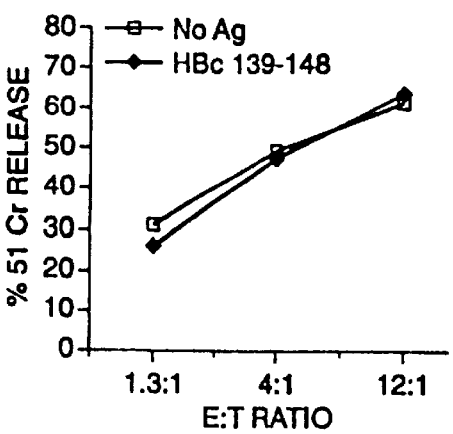
Figure 4F:
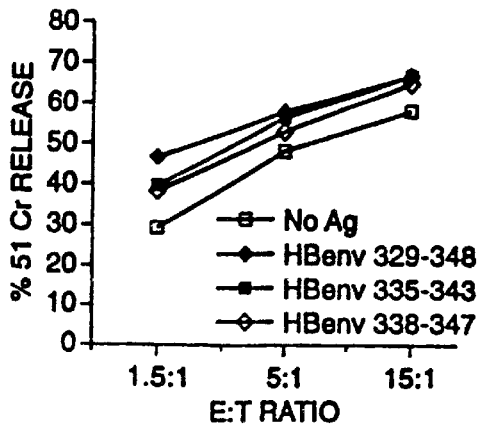
Figure 4G:
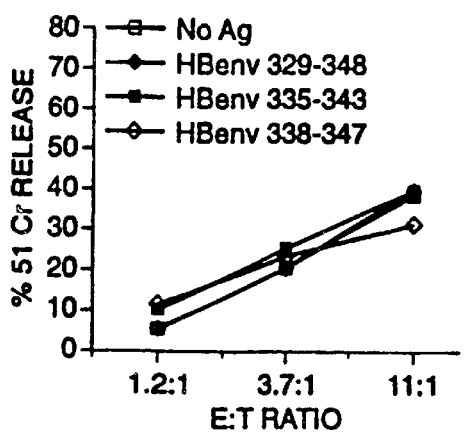
Figure 4H:
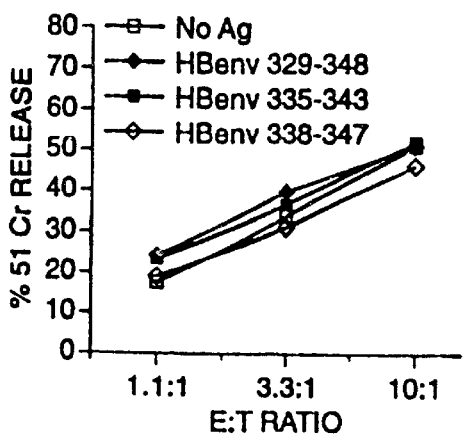
Figure 4I:
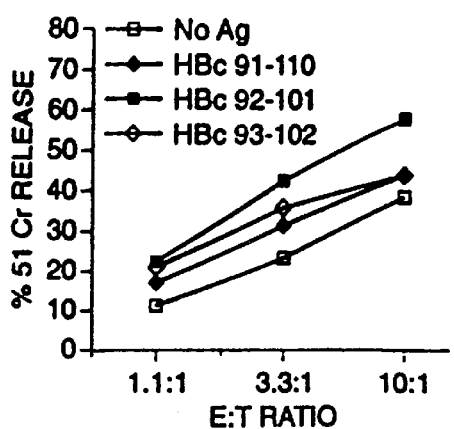
Figure 4J:
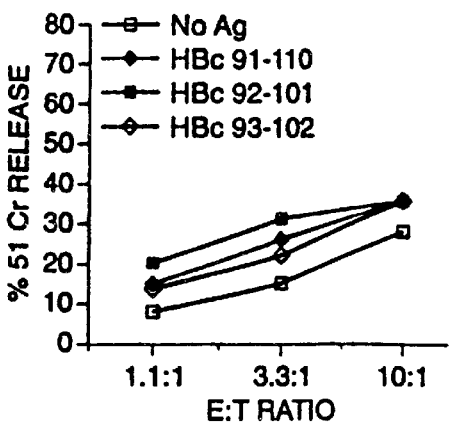
Figure 4K:
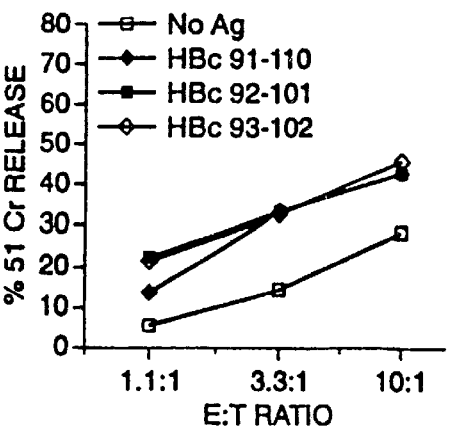
Figure 4I:
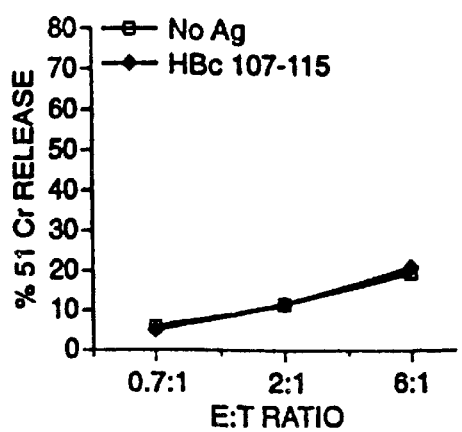

The present invention provides compositions and methods for inducing an effective CTL-mediated response to an antigen of interest in humans and other mammals. The composition is comprised of peptides that are capable of inducing MHC class I-restricted CTL responses to the antigen of interest ("CTL peptide") and an adjuvant. Another embodiment to the present invention is directed to a composition comprised of said CTL peptide and a peptide capable of eliciting a helper T lymphocyte (HTL) response. Another embodiment of the invention is directed to either or both the CTL and HTL peptide by lipidated, linked or unlinked and administered with or without an adjuvant preparation. In particularly preferred embodiments either the CTL peptide or the HTL peptide is lipidated, linked or unlinked and administered without an adjuvant. In a preferred embodiment the HTL epitope is lipidated and linked to the CTL epitope and administered without an adjuvant. In another preferred embodiment the lipidated HTL peptide is admixed with, but not linked to, at least one CTL peptide.

By administering the compositions of the present invention an effective CTL response is stimulated in the recipient mammal to the antigen of interest. The cells which are targeted by the CTL response can be involved in a wide variety of disease or potential disease states, e.g., cells which are infected by viruses, bacteria or parasites, cells which express certain tumor antigens, and cells which express autoimmune antigens or other antigens that are capable of being recognized as self by the mammal's CTL. The specifically stimulated CTL attack the target cells by secreting lymphokines (e.g., gamma interferon) and liberating products (e.g., proteolytic enzymes such as serine esterases) that inhibit replication of the infecting organism in the cells and/or kill the cells which express the antigen of interest, and thus are able to interrupt or substantially prevent the disease of interest, e.g., a viral infection, parasite or bacterial infection, a tumor or an autoimmune disease process.

The CTL inducing peptides which are useful in the compositions and methods of the present invention can be selected from a variety of sources, depending of course on the targeted antigen of interest. The CTL inducing peptides are typically small peptides that are derived from selected epitopic regions of target antigens associated with an effective CTL response to the disease of interest. Thus, by "CTL inducing peptide" or "CTL peptide" of the present invention is meant a chain of at least four amino acid residues, preferably at least six, more preferably eight to ten, sometimes eleven to fourteen residues, and usually fewer than about thirty residues, more usually fewer than about twenty-five, and preferably fewer than fifteen, e.g., eight to fourteen amino acid residues derived from selected epitopic regions of the target antigen(s).

Peptides that induce CTL responses are used in the methods and compositions of the present invention irrespective of the method or methods used to identify the epitope recognized by CTL. The CTL epitope(s) contained in the CTL peptides can be identified in one of several ways. In those cases where antigen-specific CTL lines or clones are available, for example tumor-infiltrating lymphocytes (TIL) or virus-specific CTL, these cells can be used to screen for the presence of the relevant epitopes using target cells prepared with specific antigens. Such targets can be prepared using random, or selected synthetic peptide libraries, which would be utilized to sensitize the target cells for lysis by the CTL. Another approach to identify the relevant CTL epitope when CTL are available is to use recombinant DNA methodologies. Gene, or preferably cDNA, libraries from CTL-susceptible targets are first prepared and transfected into non-susceptible target cells. This allows the identification and cloning of the gene coding the protein precursor to the peptide containing the CTL epitope. The second step in this process is to prepare truncated genes from the relevant cloned gene, in order to narrow down the region that encodes for the CTL epitope. This step is optional if the gene is not too large. The third step is to prepare synthetic peptides of approximately 10–20 amino acids of length, overlapping by 5 residues, which are used to sensitize targets for the CTL. When a peptide, or peptides, are shown to contain the relevant CTL epitope, smaller peptides can be prepared to establish the peptide of minimal size that contains the CTL epitope. These epitopes are usually contained within 9–10 residues. Examples of peptides containing known CTL epitopes identified in this way are listed below.

| ANTIGEN SOURCE | SEQUENCE | SEQ. ID NO. | HLA-RESTRICTION |
|---|---|---|---|
| MAGE-1 | EADPTGHSY | 1 | A1 |
| HIV nef84–94 | AVDLSHFLK | 2 | A11 |
| EBNA4 416–424 | IVTDFSVIK | 3 | A11 |
| HBc18–27 | FLPSDFFPSV | 4 | A2.1 |
| HIV RT | ILKEPVHGV | 5 | A2.1 |
| HTLV-1, Tox 12–19 | LFGYPVYV | 6 | A2.1 |
| Influenza A, M1 58–66 | GILGFVFTL | 7 | A2.1 |
| HCMV, gB 619–628 | IAGNSAYEYV | 8 | A2.1 |
| p53 264–272 A8 | LLGRNSFEV | 9 | A2.1 |
| HBVadr-ENV (S Ag335–343) | WLSLLVPFV | 10 | A2.1 |
| c-ErbB2 (HER-2/neu) | RFRELVSEFSRMARDPQ | 11 | A2.1 |
| HIV nef73–82 | QVPLRPMTYK | 12 | A3, A11 |
| HIV-1 NL43 env gp41768–778 | RLRDLLLIVTR | 13 | A3.1 |
| HCV 141–151 | STLPETTTVRR | 14 | A31 Aw68 |
| NP 383–391 | SRYWAIRTR | 15 | B27 |
| HIV gag p24 265–274 | KRWIILGLNK | 16 | B27 |
| P. falciparum circumsp.368-375 | KPKDELDY | 17 | B35 |
| P. falciparum circumsp.368-375 | KSKDLEDY | 18 | B35 |
| P. falciparum liverAg1850–1857 | KPNDKSLY | 19 | B35 |
| HIV-2 | TPYDINQML | 20 | B53 |
| P. falciparum liverAg1786–1794 | KPIVQYDNF | 21 | B53 |
| B53 self peptide | YPAEITLTW | 22 | B53 |
| HIV gp41 586–593 | YLKDQQLL | 23 | B8 |
| NP 380–388 | ELRSRYWAI | 24 | B8 |
| EBV EBNA-3 | FLRGRAYGI | 25 | B8 |
| HIV gag261–269 | GEIYKRWII | 26 | B8 |
| HIV gag331–339 | DCKTILKAL | 27 | B8 |
| HIV pol185–193 | DPKVKQWPL | 28 | B8 |
| HIV gp41 586–593 | YLKDQQLYL | 29 | B8 |
| HIV gap p17.3 | GGKKKYKLK | 30 | B8 |

Another way of identifying a peptide containing a CTL epitope, when CTLs are present, is to elute the peptide with an acid or base. The peptides associated with MHC molecules are present on the cells that are lysed by the CTL. The eluted peptides are separated using a purification method such as HPLC, and individual fractions are tested for their capacity to sensitize targets for CTL lysis. When a fraction has been identified as containing the CTL peptide, it is further purified and submitted to sequence analysis. The peptide sequence can also be determined using tandem mass spectrometry. A synthetic peptide is then prepared and tested with the CTL to corroborate that the correct sequence and peptide have been identified.

In some circumstances, where CTL are not available there are other means to identify potential CTL epitopes. These methods rely in the identification of MHC-binding peptides from known protein sequences. These methods have been described in detail in pending patent applications (U.S. patent applications Ser. Nos. 08/159,339, 08/073,205 and EPO Patent Application No. 92201252.1, which are herein incorporated by reference). Briefly, the protein sequences for example from viral or tumor cell components are examined for the presence of MHC-binding motifs. These binding motifs which exist for each MHC allele, are conserved amino acid residues, usually at positions 2 (or 3) and 9 (or 10) in peptides of 9–10 residues long. Synthetic peptides are then prepared of those sequences bearing the MHC binding motifs, and subsequently are tested for their ability to bind to MHC molecules. The MHC binding assay can be done either using cells which express high number of empty MHC molecules (cellular binding assay), or using purified MHC molecules. Lastly, the MHC binding peptides are then tested for their capacity to induce a CTL response in naive individuals, either in vitro using human lymphocytes, or in vivo using HLA-transgenic animals. These CTL are tested using peptide-sensitized target cells, and targets that naturally process the antigen, such as viral infected cells or tumor cells. For example, a HLA-A1-restricted CTL epitope for the tumor-associated antigen MAGE-3 has been identified using this approach and is the subject of a pending patent application (U.S. patent application Ser. No. 08/186,266, which is herein incorporated by reference.

Desirably, the CTL peptide will be as small as possible while still maintaining substantially all of the biological activity of a larger peptide. When possible, it may be desirable to optimize peptides of the invention to a length of eight to twelve amino acid residues, more usually nine or ten amino acid residues, commensurate in size with endogenously processed antigen peptide that is bound to MHC class I molecules on the cell surface. See generally, Schumacher et al., *Nature* 350:703–706 (1991); Van Bleek et al., *Nature* 348:213–216 (1990); Rotzschke et al., *Nature* 348:252–254 (1990); and Falk et al., *Nature* 351:290–296 (1991), which are incorporated herein by reference. By biological activity of a CTL inducing peptide is meant the ability to bind an appropriate MHC molecule and, in the case of peptides useful for stimulating CTL responses, induce a CTL response against the selected antigen or antigen mimetic. By a CTL response is meant a $CD8^+$ T lymphocyte response specific for an antigen of interest, wherein $CD8^+$, MHC class I-restricted T lymphocytes are activated. As noted above, the activated cytotoxic T lymphocytes will secrete a variety of products which inhibit and may or may not kill the targeted cell.

The compositions and methods of the present invention are particularly preferred for targeting host cells infected by viruses. CTL responses are an important component of the immune responses of most mammals to a wide variety of viruses, and the present invention provides a means to effectively stimulate a CTL response to virus-infected cells and treat or prevent such an infection in a host mammal. Thus the compositions and methods of the present invention are applicable to any virus presenting protein and/or peptide antigens. Such viruses include but are not limited to the following, pathogenic viruses such as influenza A and B viruses (FLU-A, FLU-B), human immunodeficiency type I and II viruses (HIV-I, HIV-II), Epstein-Barr virus (EBV), human T lymphotropic (or T-cell leukemia) virus type I and type II (HTLV-I, HTLV-II), human papillomaviruses types 1 to 18 (HPV-1 to HPV-18), rubella (RV), varicella-zoster (VZV), hepatitis B (HBV), hepatitis C (HCV), adenoviruses (AV), and herpes simplex viruses(HV). In addition, cytomegalovirus (CMV), poliovirus, respiratory syncytial (RSV), rhinovirus, rabies, mumps, rotavirus and measles viruses.

In a like manner, the compositions and methods of the present invention are applicable to tumor-associated proteins, which could be sources for CTL epitopes. Such tumor proteins and/or peptides, include, but are not limited to, products of the MAGE-1, -2 and -3 genes, products of the c-ErbB2 (HER-2/neu) proto-oncogene, tumor suppressor and regulatory genes which could be either mutated or overexpressed such as p53, ras, myc, and RB1. Tissue specific proteins to target CTL responses to tumors such as prostatic specific antigen (PSA) and prostatic acid phosphatase (PAP) for prostate cancer, and tyrosinase for melanoma. In addition viral related proteins associated with cell transformation into tumor cells such as EBNA-1, HPV E6 and E7 are likewise applicable. A large number of peptides from some of the above proteins have been identified for the presence of MHC-binding motifs and for their ability to bind with high efficiency to purified MHC molecules and are the subject of pending patent applications (U.S. patent application Ser. Nos. 08/159,339 and 08/073,205, previously incorporated herein by reference).

The peptides can be prepared "synthetically," as described hereinbelow, or by recombinant DNA technology. Although the peptide will preferably be substantially free of other naturally occurring viral, bacterial, parasitic, tumor or self proteins and fragments thereof, in some embodiments the peptides can be synthetically conjugated to native fragments or particles. The term peptide is used interchangeably with polypeptide in the present specification to designate a series of amino acids connected one to the other by peptide bonds between the alpha-amino and alpha-carboxy groups of adjacent amino acids. The polypeptides or peptides can be a variety of lengths, either in their neutral (uncharged) forms or in forms which are salts, and either free of modifications such as glycosylation, side chain oxidation, or phosphorylation or containing these modifications, subject to the condition that the modification not destroy the biological activity of the polypeptides as herein described.

The terms "homologous", "substantially homologous", and "substantial homology" as used herein denote a sequence of amino acids having at least 50% identity wherein one sequence is compared to a reference sequence of amino acids. The percentage of sequence identity or homology is calculated by comparing one to another when aligned to corresponding portions of the reference sequence.

The peptides useful in the present invention can be optionally flanked and/or modified at one or both of the N- and C-termini, as desired, by amino acids from the naturally occurring (e.g., HBV) sequences, amino acids added to facilitate linking to another peptide or to a lipid, other N- and C-terminal modifications, linked to carriers, etc., as further described herein. Additional amino acids can be added to the termini of a peptide to provide for modifying the physical or chemical properties of the peptide or the like. Amino acids such as tyrosine, cysteine, lysine, glutamic or aspartic acid, or the like, can be introduced at the C- or N-terminus of the peptide or oligopeptide. In addition, the peptide sequences can differ from the natural sequence by being modified by terminal-$NH_2$ acylation, e.g., by alkanoyl ($C_1$–$C_{20}$) or thioglycolyl acetylation, terminal-carboxy amidation, e.g., ammonia, methylamine, etc. In some instances these modifications may provide sites for linking to a support or other molecule.

It will be understood that the peptides of the present invention or analogs thereof which have CTL stimulating activity may be modified to provide other desired attributes, e.g., improved pharmacological characteristics, while increasing or at least retaining substantially all of the biological activity of the unmodified peptide. For instance, the peptides can be modified by extending, decreasing or substituting in the peptides amino acid sequences by, e.g., the addition or deletion of amino acids on either the amino terminal or carboxy terminal end, or both, of peptides derived from the sequences disclosed herein.

With respect to treatment or prevention of hepatitis B infection in humans, selection of a CTL inducing peptide(s) useful in the present invention can be as set forth in more detail in copending applications U.S. Ser. Nos. 07/935,811, 07/935,898 and 08/024,120 which are incorporated herein by reference. These applications provide the ability to select one or more peptides that induce CTL response to a hepatitis B antigen, which response is capable of killing (or inhibiting) cells which are infected by or otherwise express (in the case of transfected cells) the native HBV antigens. The HBV CTL inducing peptide will usually have at least four, sometimes six, often seven or more residues, or a majority of amino acids of that peptide, that are identical or homologous when compared to the corresponding portion of the naturally occurring HBV sequence. For example, those peptides which are preferred for stimulating HBV CTL responses include

| SOURCE | POSITION | SEQUENCE | SIZE | SEQ. ID NO. | BINDING A2 |
|---|---|---|---|---|---|
| HBV POL | 1117 | LLAQFTSAI | 9 | 31 | 9.6000 |
| HBV ENV | 338 | LLVPFVQWFV | 10 | 32 | 1.6000 |
| HBV ENV | 335 | WLSLLVPFV | 9 | 33 | 0.9600 |
| HBV ENV | 1116 | FLLAQFTSA | 9 | 34 | 0.6600 |
| HBV POL | 1147 | FLLSLGIHL | 9 | 35 | 0.5200 |
| HBV POL | 1245 | ALMPLYACI | 9 | 36 | 0.5000 |
| HBV ENV | 249 | ILLLCLIFLL | 10 | 37 | 0.3000 |
| HBV POL | 1092 | KLHLYSHPI | 9 | 38 | 0.2900 |
| HBV ENV | 259 | VLLDYQGML | 9 | 39 | 0.1100 |
| HBV ENV | 378 | LLPIFFCLWV | 10 | 40 | 0.1000 |
| HBV ENV | 177 | VLQAGFFLL | 9 | 41 | 0.0660 |
| HBV POL | 721 | YLHTLWKAGI | 10 | 42 | 0.0560 |
| HBV POL | 721 | YLHTLWKAGV | 10 | 43 | 0.1300 |
| HBV ENV | 377 | PLLPIFFCL | 9 | 44 | 0.0310 |
| HBV NUC (CORE) | 529 | ILSTLPETTV | 10 | 45 | 0.0220 |

Other HBV CTL stimulating peptides include HBenv$_{309-328}$ (peptide 799.08), HBenv$_{329-349}$ (peptide 799.09) or HBenv$_{349-368}$ (peptide 799.10), and the HBc region HBc$_{91-110}$ (peptide 802.03).

For example, a CTL inducing HBc peptide comprises from six to thirty amino acids and is derived from the region HBc18–27, contains at least one CTL epitopic site, and has at least seven amino acids wherein a majority of amino acids of the peptide will be identical or substantially homologous, when compared to the amino acids comprising the corresponding portion of the naturally occurring HBc18–27 sequence. A representative peptide of this region is peptide HBc18–27, which has the following sequence (for HBV subtype ayw):

HBc18–27—[Seq. ID No. 4]
FLPSDFFPSV

With respect to treatment or prevention of hepatitis C infection in mammals, one or more peptides that induce a CTL response to a hepatitis C antigen may be selected. The HCV CTL-inducing peptide will usually have at least four, sometimes six, often seven or more residues, or a majority of amino acids of that peptide that are identical or homologous when compared to the corresponding portion of the naturally occurring HCV sequence. For example, those peptides which are preferred for stimulating HCV CTL responses include sequences contained within copending U.S. patent applications (Ser. Nos. 08/159,339 and 08/073, 205, previously incorporated herein by reference), in particular peptides 1073.05 (LLFNILGGWV) [Seq ID No. 46], 1090.18 (FLLLADARV) [Seq ID No. 49], 939.20 (LLALLSCLTV) [Seq ID No. 47], 1073.07 (YLLPRRGPRL) [Seq. ID No. 52], 1013.10 (DLMGYIPLV) [Seq ID No. 51], 1073.10 (GVAGALVAFK) [Seq ID No. 61]. Also suitable are other peptides identified by other methods, such as STNPKPQK [Seq ID No. 62] and GPRLGVRAT [Seq ID No. 63] (Koziel et al., *J. Virol.* 67:7522–7535, 1993), and YPW-PLYGNEGLGWAGWLLSP [Seq ID No. 64] (Kita et al., Abstract #631, 1993 Am. Assoc. For Study of Liver Diseases Meeting). Other HCV derived peptides for stimulating HCV CTL responses include the following:

| SOURCE | POSITION | SEQUENCE | SIZE | SEQ. ID NO. | BINDING A2 |
|---|---|---|---|---|---|
| HCV NS4 | 1807 | LLFNILGGWV | 10 | 46 | 3.5000 |
| HCV CORE | 178 | LLALLSCLTV | 10 | 47 | 0.6050 |
| HCV NS4 | 1585 | YLVAYQATV | 9 | 48 | 0.2450 |
| HCV NS1/ENV | 725 | FLLLADARV | 9 | 49 | 0.2250 |
| HCV NS4 | 1851 | ILAGYGAGV | 9 | 50 | 0.2150 |
| HCV CORE | 132 | DLMGYIPLV | 9 | 51 | 0.0835 |
| HCV CORE | 35 | YLLPRRGPRL | 10 | 52 | 0.0725 |
| NS1/ENV2 | 686 | ALSTGLIHL | 9 | 53 | 0.0415 |
| HCV CORE | 178 | LLALLSCLTI | 10 | 54 | 0.0340 |
| HCV NS5 | 2578 | RLIVFPDLGV | 10 | 55 | 0.0320 |
| HCV NS5 | 2885 | RLHGLSAFSL | 10 | 56 | 0.0200 |
| HCV NS4 | 1811 | ILGGWVAAQL | 10 | 57 | 0.0180 |
| HCV ENV1 | 364 | SMVGNWAKV | 9 | 58 | 0.0155 |
| HCV NS3 | 1131 | YLVTRHADV | 9 | 59 | 0.0109 |
| HCV NS4 | 1666 | VLAALAAYCL | 10 | 60 | 0.0106 |

With respect to treatment or prevention of HPV infections in mammals, one or more peptides that induce a CTL response to a HPV may be selected. The HPV CTL-inducing peptide will usually have at least four, sometimes six, often seven or more residues, or a majority of amino acids of that peptide that are identical or homologous when compared to the corresponding portion of the naturally occurring HCV sequence. For example, those peptides which are preferred for stimulating HPV CTL responses include sequences contained within copending U.S. patent applications (Ser. Nos. 08/159,339, 08/073,205 and EPO Patent Application 92201252.1, previously incorporated by reference), in particular the following peptides:

| SOURCE | POSITION | SEQUENCE | SIZE | SEQ. ID NO. | BINDING A2 |
|---|---|---|---|---|---|
| HPV16 E7 | 82 | LLMGTLGIV | 9 | 65 | 0.0240 |
| HPV16 E7 | 11 | YMLDLQPET | 9 | 66 | 0.1400 |
| HPV16 E6 | 52 | FAFRDLCIV | 9 | 67 | 0.0570 |
| HPV16 E7 | 86 | TLGIVCPIC | 9 | 68 | 0.0750 |
| HPV16 E7 | 7 | TLHEYMLDL | 9 | 69 | 0.0070 |
| HPV16 E7 | 85 | GTLGIVCPI | 9 | 70 | 0.0820 |
| HPV16 E7 | 12 | MLDLQPETT | 9 | 71 | 0.0028 |
| HPV16 E6 | 29 | TIHDIILECV | 10 | 72 | 0.0210 |

With respect to treatment or prevention of human immunodeficiency virus 1 and 2 in humans, one or more peptides that induce a CTL response to a HIV 1 or 2 antigen may be selected. The HIV CTL-inducing peptide will usually have at least four, sometimes six, often seven or more residues, or a majority of amino acids of that peptide that are identical or homologous when compared to the corresponding portion of the naturally occurring HIV sequence. For example, those peptides which are preferred for stimulating HIV CTL responses include the following peptides:

| SOURCE | POSITION | SEQUENCE | SIZE | SEQ. ID NO. | BINDING A2 |
|---|---|---|---|---|---|
| HIV | 367 | VLAEAMSQV | 9 | 73 | 0.1100 |
| HIV | 1496 | LLWKGEGAVV | 10 | 74 | 0.0360 |
| HIV | 1496 | LLWKGEGAV | 9 | 75 | 0.0230 |

-continued

| SOURCE | POSI-TION | SEQUENCE | SIZE | SEQ. ID NO. | BINDING A2 |
|---|---|---|---|---|---|
| HIV | 1004 | ILKEPVHGV | 9 | 76 | 0.0190 |
| HIV | 1129 | IVGAETFYV | 9 | 77 | 0.0099 |
| HIV | 1129 | IIGAETFYV | 9 | 78 | 0.0260 |
| HIV | 2182 | LWVTVYYGV | 9 | 79 | 0.0014 |
| HIV | 2182 | LMVTVYYGV | 9 | 80 | 0.4400 |

Several tumor associated antigens have also been correlated with CTL responses, including, but not limited to, renal cell carcinoma antigens, breast cancer antigens, carcinoembryonic antigen (CEA), melanoma (MAGE-1 and MAGE-3) antigens, prostate cancer specific antigen and others. For example, a HLA-A1-restricted CTL epitope for the tumor-associated antigen MAGE-3 has been identified using this approach and is the subject of a pending patent application (U.S. patent application Ser. No. 08/186,266, previously incorporated herein by reference.

Peptides which stimulate CTL responses to tumor antigens and which can be used in the methods and compositions of the present invention can be selected as described in, for example, U.S. patent applications Serial Nos. 08/159,339 and 08/073,205, previously incorporated by reference. For example, representative peptide which are preferred for inducing MAGE-3 and -1 CTL responses include the following:

| SOURCE | POSI-TION | SEQUENCE | SIZE | SEQ. ID NO. | BINDING A2 |
|---|---|---|---|---|---|
| MAGE2 | 105 | KMVELVHFL | 9 | 81 | 0.5100 |
| MAGE2 | 105 | KMVELVHFLL | 10 | 82 | 0.2200 |
| MAGE3 | 153 | LVFGIELMEV | 10 | 83 | 0.1100 |
| MAGE1 | 278 | KVLEYVIKV | 9 | 84 | 0.0900 |
| MAGE1 | 105 | KVADLVGFLL | 10 | 85 | 0.0560 |
| MAGE3 | 105 | KVAEFVHFL | 9 | 86 | 0.0550 |
| MAGE1 | 92 | CILESLFRA | 9 | 87 | 0.0460 |
| MAGE1 | 264 | FLWGPRALA | 9 | 88 | 0.0420 |
| MAGE1 | 200 | VMIAMEGGHA | 10 | 89 | 0.0360 |
| MAGE1 | 38 | LVLGTLEEV | 9 | 90 | 0.0320 |
| MAGE1 | 301 | ALREEEEGV | 9 | 91 | 0.0210 |
| MAGE1 | 270 | ALAETSYVKV | 10 | 92 | 0.0150 |
| MAGE1 | 282 | YVIKVSARV | 9 | 93 | 0.0140 |
| MAGE1 | 269 | RALAETSYV | 9 | 94 | 0.0100 |

The present invention enhances the effectiveness of a CTL-inducing peptide by co-delivery with a sequence which contains at least one epitope that is capable of inducing a HTL response. By a HTL response is meant a CD4$^+$ T lymphocyte response wherein CD4$^+$ T lymphocytes are activated. The HTLs stimulated by the HTL-inducing peptide can be the T-helper 1 and/or T-helper 2 phenotype, for example. The activated T helper lymphocytes will secrete a variety of products, including, for example, interleukin-2, which may facilitate expression of the T cell receptor and promote recognition by activated CTLs.

HTL-inducing epitopes can be provided by peptides which correspond substantially to the antigen targeted by the CTL-inducing peptide, or more preferably is a peptide to a more widely recognized antigen, and preferably is not specific for a particular histocompatibility antigen restriction. Peptides which are recognized by most individuals regardless of their MHC class II phenotype ("promiscuous") may be particularly advantageous. The HTL peptide will typically comprise from six to thirty amino acids and contain a HTL-inducing epitope. For example, illustrative peptides useful in the present invention are those which contain HTL inducing epitopes within a HTL peptide from tetanus toxoid 830–843 having the sequence Gln-Tyr-Ile-Lys-Ala-Asn-Ser-Lys-Phe-Ile-Gly-Ile-Thr-Glu (QYIKANSKFIGITE) [Seq. ID No. 95], malaria circumsporozoite 382–398 Lys-Ile-Ala-Lys-Met-Lys-Ala-Ser-Ser-Val-Phe-Asn-Val-Val-Asn-Ser (KIAKMEKASSVFNVVNS) [Seq. ID No. 96]; malaria circumsporozoite $_{378-398}$ Asp-Ile-Glu-Lys-Lys-Ile-Ala-Lys-Met-Lys-Ala-Ser-Ser-Val-Phe-Asn-Val-Val-Asn-Ser (DIEKKIAKMEKASSVFNVVNS) [Seq. ID No. 97], and ovalbumin 323–336 Ile-Ser-Gln-Ala-Val-His-Ala-Ala-His-Ala-Glu-Ile-Asn-Glu [Seq. ID No. 98] and the influenza epitope $_{307-319}$ Pro-Lys-Tyr-Val-Lys-Gln-Asn-Thr-Leu-Lys-Leu-Ala-Thr [Seq. ID No. 99]. In addition suitable T helper peptides have been identified as described in pending U.S. Patent Application Ser. No. 08/121,101, incorporated herein by reference.

Other examples of HTL-inducing peptides are those which are specific for the antigen (virus or other organism, tumor, etc.) being targeted by the CTL. For example, several HTL-inducing peptides specific for HBV have been described, such as HBc$_{1-20}$, having the sequence: Met-Asp-Ile-Asp-Pro-Tyr-Lys-Glu-Phe-Gly-Ala-Thr-Val-Glu-Leu-Leu-Ser-Phe-Leu-Pro [Seq. ID No. 100]; peptides from the region HBc$_{50-69}$, which has the sequence Pro-His-His-Tyr-Ala-Leu-Arg-Gln-Ala-Ile-Leu-Cys-Trp-Gly-Glu-Leu-Met-Tyr-Leu-Ala [Seq. ID No. 101], and from the region of HBc$_{100-139}$, including HBc$_{100-119}$ having the sequence Leu-Leu-Trp-Phe-His-Ile-Ser-Cys-Leu-Thr-Phe-Gly-Arg-Glu-Thr-Val-Ile-Glu-Tyr-Leu [Seq. ID No. 102] (where Ile$_{116}$ is Leu in the HBV adw subtype), HBc$_{117-131}$ having the sequence Glu-Tyr-Leu-Val-Ser-Phe-Gly-Val-Trp-Ile-Arg-Thr-Pro-Pro-Ala [Seq. ID No. 103], and peptide HBc$_{120-139}$ having the sequence Val-Ser-Phe-Gly-Val-Trp-Ile-Arg-Thr-Pro-Pro-Ala-Tyr-Arg-Pro-Pro-Asn-Ala-Pro-Ile [Seq. ID No. 104]. See, Ferrari et al., *J. Clin. Invest.* 88:214–222 (1991), and U.S. Pat. No. 4,882,145, and U.S. Pat. No. 5,143,726, each of which is incorporated herein by reference.

The CTL or HTL inducing peptides employed in the compositions and methods of the present invention need not be identical to specific peptides disclosed in aforementioned disclosures, and can be selected by a variety of techniques, for example, according to certain motifs as described above. Therefore, the peptides may be subject to various changes, such as insertions, deletions, and substitutions, either conservative or non-conservative, where such changes might provide for certain advantages in their use. By conservative substitutions is meant replacing an amino acid residue with another which is biologically and/or chemically similar, e.g., one hydrophobic residue for another, or one polar residue for another. The substitutions include combinations such as Gly, Ala; Val, Ile, Leu; Asp, Glu; Asn, Gln; Ser, Thr; Lys, Arg; and Phe, Tyr. Usually, the portion of the sequence which is intended to substantially mimic a CTL or HTL stimulating epitope will not differ by more than about 20% from the corresponding sequence of a native antigen, when known, except where additional amino acids may be added at either terminus for the purpose of modifying the physical or chemical properties of the peptide for, e.g., ease of linking or coupling, and the like. In those situations where regions of the peptide sequences are found to be polymorphic among antigen subtypes, it may be desirable to vary one or more particular amino acids to more effectively mimic differing CTL or HTL epitopes of different antigen strains.

In some instances it may be desirable to combine two or more peptides which contribute to stimulating specific CTL responses in one or more patients or histocompatibility types. The peptides in the composition can be identical or different, and together they should provide equivalent or greater biological activity than the parent peptide(s). For example, using the methods described herein, two or more peptides may define different or overlapping CTL epitopes from a particular region, e.g., the peptide region 799.08 (HBenv$_{309-328}$), peptide region, 799.09 (HBenv$_{329-349}$), 799.10 (HBenv$_{349-368}$), or peptide region 802.03 (HBc$_{91-110}$), which peptides can be combined in a "cocktail" to provide enhanced immunogenicity of CTL responses, and peptides can be combined with peptides having different MHC restriction elements. This composition can be used to effectively broaden the immunological coverage provided by therapeutic, vaccine or diagnostic methods and compositions of the invention among a diverse population.

In some embodiments the CTL inducing peptides of the invention are linked to the HTL inducing peptides. CTL inducing peptides/T helper conjugates can be linked by a spacer molecule, or the CTL peptide may be linked to the HTL peptide without a spacer. When present, the spacer is typically comprised of relatively small, neutral molecules, such as amino acids or amino acid mimetics, which are substantially uncharged under physiological conditions and may have linear or branched side chains. The spacers are typically selected from, e.g., Ala, Gly, or other neutral spacers of nonpolar amino acids or neutral polar amino acids. In certain preferred embodiments herein the neutral spacer is Ala. It will be understood that the optionally present spacer need not be comprised of the same residues and thus may be a hetero- or homo-oligomer. Preferred exemplary spacers are homo-oligomers of Ala. When present, the spacer will usually be at least one or two residues, more usually three to six residues. When the HTL-inducing peptide is conjugated to the CTL-inducing peptide, in the present or absence of a spacer, preferably with the HTL peptide is positioned at the amino end of the conjugate.

The peptides of the invention can be combined via linkage to form polymers (multimers), or can be formulated in a composition without linkage, as an admixture. Where the same peptide is linked to itself, thereby forming a homopolymer, a plurality of repeating epitopic units are presented. When the peptides differ, e.g., a cocktail representing different antigen strains or subtypes, different epitopes within a subtype, different histocompatibility restriction specificities, or peptides which contain HTL epitopes, heteropolymers with repeating units are provided. In addition to covalent linkages, noncovalent linkages capable of forming intermolecular and intrastructural bonds are also contemplated.

Linkages for homo- or hetero-polymers or for coupling to carriers can be provided in a variety of ways. For example, cysteine residues can be added at both the amino- and carboxy-termini, where the peptides are covalently bonded via controlled oxidation of the cysteine residues. Also useful are a large number of heterobifunctional agents which generate a disulfide link at one functional group end and a peptide link at the other, including N-succidimidyl-3-(2-pyridyldithio) proprionate (SPDP). This reagent creates a disulfide linkage between itself and a cysteine residue in one protein and an amide linkage through the amino on a lysine or other free amino group in the other. A variety of such disulfide/amide forming agents are known. See, for example, Immun. Rev. 62:185 (1982). Other bifunctional coupling agents form a thioether rather than a disulfide linkage. Many of these thioether forming agents are commercially available and include reactive esters of 6-maleimidocaproic acid, 2 bromoacetic acid, 2-iodoacetic acid, 4-(N-maleimido-methyl) cyclohexane-1-carboxylic acid and the like. The carboxyl groups can be activated by combining them with succinimide or 1-hydroxy-2-nitro-4-sulfonic acid, sodium salt. A particularly preferred coupling agent is succinimidyl 4-(N-maleimidomethyl) cyclohexane-1-carboxylate (SMCC). Of course, it will be understood that linkage should not substantially interfere with either of the linked groups to function as described, e.g., to function as a CTL determinant or HTL determinant.

As a further aspect of the present invention the HTL-inducing peptide(s) and CTL-inducing peptide(s) can be delivered to the patient in the presence of a lipid. The lipid residue, such as palmitic acid or the like (as described further below, which is attached to alpha and epsilon amino groups of a Lys residue ((PAM)$_2$Lys), is attached to the amino terminus of the HTL-inducing peptide. The lipid can be attached directly to the HTL peptide, or, more typically, indirectly via a linkage, such as a Ser-Ser, Gly, Gly-Gly, Ser linkage or the like.

As another example of lipid-HTL priming of CTL responses, E. coli lipoprotein, such as tripalmitoyl-S-glycerylcysteinly-seryl-serine (P$_3$CSS), can be used to prime specific CTL when covalently attached to an appropriate HTL peptide. See, Deres et al., Nature 342:561–564 (1989), incorporated herein by reference. The HTL peptides can be coupled to P$_3$CSS, for example, and the lipopeptide administered in conjunction with the CTL inducing peptide to an mammal to specifically prime a CTL response to the antigen of interest.

Yet another example of lipid priming of CTL response is achieved by conjugating the CTL/T helper-peptide-conjugate with uncharged fatty acid residues of different chain lengths and degrees of unsaturation, ranging from acetic to stearic acid as well as to negatively charged succinyl residues via the appropriate carboxylic acid anhydrides.

The lipid may be linked to other peptides which present HTL epitopes which are then combined with the lipid. When the HTL and CTL are linked in a conjugate, the arrangement of the components of the conjugate comprising the CTL inducing peptide/T helper peptide/lipid can be varied. In one case, the lipid moiety can be linked to the amino terminal end of the CTL inducing peptide, which in turn is linked at its carboxy terminal to the T helper peptide. In another case, the lipid is linked at the amino terminal end of the T helper peptide, which is linked at its carboxy terminal to the CTL inducing peptide. In each case, a spacer molecule can be selectively inserted between the lipid moiety and the CTL or T helper peptide, as well as between the T helper and the CTL inducing peptides. In the case of the spacer between the lipid and the T helper or CTL inducing peptide, a preferred example comprises Lys-Ser-Ser, although other spacers are described herein. An example of a spacer between the T helper and CTL inducing peptides will be Ala-Ala-Ala, as also described in further detail herein.

As further described herein, the lipidated HTL peptide and CTL peptide can then be emulsified in an adjuvant, e.g., incomplete Freund's adjuvant, alum or montanide.

In an exemplary embodiment described below, a T helper peptide from substantially within TT830–843 was lipidated at its N-terminus (with (PAM)$_2$) via a linker (KSS) and then linked at its C-terminus (via a linker AAA) with a HBV CTL inducing peptide, HBc18–27. Thus, the structure of the peptide was (PAM)$_2$KSS-T helper-AAA-CTL and had the sequence of (PAM)$_2$KSS-ISQAVHAAHAEINE-AAA-TYQRTRALV [Seq ID No. 105]. This conjugate, when administered to transgenic animals expressing the HLA2.1 antigen, was shown to induce specific CTL priming of animals. It was also established that the CTL induced by the peptide recognized endogenously synthesized HBcore antigens. When the same lipid-THL-CTL peptide conjugate was administered to humans an induction of specific CTL response was observed, where the response dose dependent both in proportion of subjects exhibiting a positive response as well as in the magnitude of the response obtained.

The peptides of the invention can be prepared in a wide variety of ways. Because of their relatively short size, the peptides can be synthesized in solution or on a solid support in accordance with conventional techniques. Various automatic synthesizers are commercially available and can be used in accordance with known protocols. See, for example, Stewart and Young, *Solid Phase Peptide Synthesis*, 2d. ed., Pierce Chemical Co. (1984); Tam et al., *J. Am. Chem. Soc.* 105:6442 (1983); Merrifield, *Science* 232:341–347 (1986); and Barany and Merrifield, *The Peptides*, Gross and Meienhofer, eds., Academic Press, New York, pp. 1–284 (1979), each of which is incorporated herein by reference.

Alternatively, recombinant DNA technology may be employed wherein a nucleotide sequence which encodes a CTL peptide and/or T helper peptide of interest is inserted into an expression vector, transformed or transfected into an appropriate host cell and cultivated under conditions suitable for expression. These procedures are generally known in the art, as described generally in Sambrook et al., *Molecular Cloning. A Laboratory Manual*, Cold Spring Harbor Press, Cold Spring Harbor, N.Y. (1982), and Ausubel et al., (ed.) *Current Protocols in Molecular Biology*, John Wiley and Sons, Inc., New York (1987), and U.S. Pat. Nos. 4,237,224, 4,273,875, 4,431,739, 4,363,877 and 4,428,941, for example, which disclosures are incorporated herein by reference. Thus, fusion proteins which comprise one or more peptide sequences can be used to present the CTL and HTL determinants. For example, a recombinant HBV surface antigen protein is prepared in which the HBenv amino acid sequence is altered so as to more effectively present epitopes of peptide regions described herein to stimulate a CTL response. By this means a polypeptide is used which incorporates several CTL and HTL epitopes.

As the coding sequence for peptides of the length contemplated herein can be synthesized by chemical techniques, for example, the phosphotriester method of Matteucci et al., *J. Am. Chem. Soc.* 103:3185 (1981), modification can be made simply by substituting the appropriate base(s) for those encoding the native peptide sequence. The coding sequence can then be provided with appropriate linkers and ligated into expression vectors commonly available in the art, and the vectors used to transform suitable hosts to produce the desired fusion protein. A number of such vectors and suitable host systems are now available. For expression of the fusion proteins, the coding sequence will be provided with operably linked start and stop codons, promoter and terminator regions and usually a replication system to provide an expression vector for expression in the desired cellular host. For example, promoter sequences compatible with bacterial hosts are provided in plasmids containing convenient restriction sites for insertion of the desired coding sequence. The resulting expression vectors are transformed into suitable bacterial hosts. Of course, yeast or mammalian cell hosts may also be used, employing suitable vectors and control sequences.

The peptides of the present invention and pharmaceutical and vaccine compositions thereof are useful for administration to mammals, particularly humans, to treat and/or prevent viral, bacterial, and parasitic infections. As the peptides are used to stimulate cytotoxic T-lymphocyte responses to HBV infected cells, the compositions can be used to treat or prevent acute and/or chronic HBV infection.

For pharmaceutical compositions, the peptides, i.e., the compositions of lipidated HTL/CTL peptides of the invention as described above will be administered to a mammal already suffering from or susceptible to the disease being treated. Those in the incubation phase or the acute phase of disease such as a viral infection, e.g., HBV, can be treated with the immunogenic peptides separately or in conjunction with other treatments, as appropriate. In therapeutic applications, compositions are administered to a patient in an amount sufficient to elicit an effective CTL response to the disease and to cure or at least partially arrest its symptoms and/or complications. An amount adequate to accomplish this is defined as "therapeutically effective dose." Amounts effective for this use will depend on, e.g., the peptide composition, the manner of administration, the stage and severity of the disease being treated, the weight and general state of health of the patient, and the judgment of the prescribing physician, but generally range for the initial immunization (that is for therapeutic or prophylactic administration) from about 1.0 $\mu$g to about 50 mg, preferably 1 $\mu$g to 500 $\mu$g, most preferably 1 $\mu$g to 250 $\mu$g followed by boosting dosages of from about 1.0 $\mu$g to 50 mg, preferably 1 $\mu$g to 500 $\mu$g, and more preferably 1 $\mu$g to about 250 $\mu$g of peptide pursuant to a boosting regimen over weeks to months depending upon the patient's response and condition by measuring specific CTL activity in the patient's blood. It must be kept in mind that the peptides and compositions of the present invention may generally be employed in serious disease states, that is, life-threatening or potentially life threatening situations. In such cases, in view of the minimization of extraneous substances and the relative nontoxic nature of the peptides, it is possible and may be felt desirable by the treating physician to administer substantial excesses of these peptide compositions.

Single or multiple administrations of the compositions can be carried out with dose levels and pattern being selected by the treating physician. In any event, the pharmaceutical formulations should provide a quantity of cytotoxic T-lymphocyte stimulatory peptides of the invention sufficient to effectively treat the patient.

For therapeutic use, administration should begin at the first sign of disease (e.g., HBV infection), to be followed by boosting doses until at least symptoms are substantially abated and for a period thereafter. In cases of established or chronic disease, such as chronic HBV infection, loading doses followed by boosting doses may be required. The elicitation of an effective CTL response during early treatment of an acute disease stage will minimize the possibility of subsequent development of chronic disease such as hepatitis, HBV carrier stage, and ensuing hepatocellular carcinoma.

Treatment of an infected mammal with the compositions of the invention may hasten resolution of the disease in acutely afflicted mammals. For those mammals susceptible (or predisposed) to developing chronic disease the compositions of the present invention are particularly useful in methods for preventing the evolution from acute to chronic disease. Where the susceptible individuals are identified prior to or during infection, for instance, as described herein, the composition can be targeted to them, minimizing need for administration to a larger population.

The peptide compositions can also be used for the treatment of chronic or established disease such as viral hepatitis and to stimulate the immune system to eliminate virus-infected cells. Those with chronic hepatitis can be identified as testing positive for virus from about 3–6 months after infection. As individuals may develop chronic HBV infection because of an inadequate (or absent) CTL response during the acute phase of their infection, it is important to provide an amount of immuno-potentiating peptide compositions of the invention in a formulation and mode of administration sufficient to effectively stimulate a CTL response. Thus, for treatment of chronic hepatitis, a representative dose is in the range of about 1.0 µg to about 50 mg, preferably 1 µg to 500 µg, most preferably 1 µg to 250 µg followed by boosting dosages of from about 1.0 µg to 50 mg, preferably 1 µg to 500 µg, and more preferably 1 µg to about 250 µg per dose. Administration should continue until at least clinical symptoms or laboratory indicators indicate that the HBV infection has been eliminated or substantially abated and for a period thereafter. Immunizing doses followed by boosting doses at established intervals, e.g., from one to four weeks, may be required, possibly for a prolonged period of time, as necessary to resolve the infection. For the treatment of chronic and carrier HBV infection it may also be desirable to combine the CTL and HTL peptides with other peptides or proteins that induce immune response to other HBV antigens, such as HBsAg.

The pharmaceutical compositions for therapeutic treatment are intended for parenteral, topical, oral or local administration. Preferably, the pharmaceutical compositions are administered parenterally, e.g., intravenously, subcutaneously, intradermally, or intramuscularly. Thus, the invention provides compositions for parenteral administration which comprise a solution of the HTL and CTL stimulatory peptides dissolved or suspended in an acceptable carrier, preferably an aqueous carrier. A variety of aqueous carriers may be used, e.g., water, buffered water, 0.4% saline, 0.3% glycine, hyaluronic acid and the like. These compositions may be sterilized by conventional, well known sterilization techniques, or may be sterile filtered. The resulting aqueous solutions may be packaged for use as is, or lyophilized, the lyophilized preparation being combined with a sterile solution prior to administration. The compositions may contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, methanol, and dissolving agents such as DMSO, etc.

The concentration of HTL and CTL stimulatory peptides of the invention in the pharmaceutical formulations can vary widely, i.e., from less than about 1%, usually at or at least about 10% to as much as 20 to 50% or more by weight, and will be selected primarily by fluid volumes, viscosities, etc., in accordance with the particular mode of administration selected.

Thus, a typical pharmaceutical composition for intravenous infusion could be made up to contain 250 ml of sterile Ringer's solution, and 50 mg of peptide. Actual methods for preparing parenterally administrable compounds will be known or apparent to those skilled in the art and are described in more detail in for example, Remington's Pharmaceutical Sciences, 17th ed., Mack Publishing Company, Easton, Pa. (1985), which is incorporated herein by reference.

The peptides of the invention may also be administered via liposomes, which serve to target the peptides to a particular tissue, such as lymphoid tissue, or targeted selectively to infected cells, as well as increase the half-life of the peptide composition. Liposomes include emulsions, foams, micelles, insoluble monolayers, liquid crystals, phospholipid dispersions, lamellar layers and the like. In these preparations the peptide to be delivered is incorporated as part of a liposome, alone or in conjunction with a molecule which binds to, e.g., a receptor prevalent among lymphoid cells, such as monoclonal antibodies which bind to the CD45 antigen, or with other therapeutic or immunogenic compositions. Thus, liposomes filled with a desired peptide of the invention can be directed to the site of lymphoid cells, where the liposomes then deliver the selected therapeutic/immunogenic peptide compositions. Liposomes for use in the invention are formed from standard vesicle-forming lipids, which generally include neutral and negatively charged phospholipids and a sterol, such as cholesterol. The selection of lipids is generally guided by consideration of, e.g., liposome size and stability of the liposomes in the blood stream. A variety of methods are available for preparing liposomes, as described in, e.g., Szoka et al., *Ann. Rev. Biophys. Bioeng.* 9:467 (1980), U.S. Pat. Nos. 4,235,871, 4,501,728, 4,837,028, and 5,019,369, incorporated herein by reference. For targeting to the immune cells, a ligand to be incorporated into the liposome can include, e.g., antibodies or fragments thereof specific for cell surface determinants of the desired immune system cells. A liposome suspension containing a peptide may be administered intravenously, locally, topically, etc. in a dose which varies according to, inter alia, the manner of administration, the peptide being delivered, and the stage of the disease being treated.

For solid compositions, conventional nontoxic solid carriers may be used which include, for example, pharmaceutical grades of mannitol, lactose, starch, magnesium stearate, sodium saccharin, talcum, cellulose, glucose, sucrose, magnesium carbonate, and the like. For oral administration, a pharmaceutically acceptable nontoxic composition is formed by incorporating any of the normally employed excipients, such as those carriers previously listed, and generally 10–95% of active ingredient, that is, one or more peptide compositions of the invention, and more preferably at a concentration of 25%–75%.

For aerosol administration, the HTL and CTL stimulatory peptide compositions are preferably supplied in finely divided form along with a surfactant and propellant. Typical percentages of peptides are 0.01%–20% by weight, preferably 1%–10%. The surfactant must, of course, be nontoxic, and preferably soluble in the propellant. Representative of such agents are the esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride. Mixed esters, such as mixed or natural glycerides may be employed. The surfactant may constitute 0.1%–20% by weight of the composition, preferably 0.25–5%. The balance of the composition is ordinarily propellant. A carrier can also be included, as desired, as with, e.g., lecithin for intranasal delivery.

In another aspect the present invention is directed to vaccines which contain as an active ingredient an immunogenically effective amount of a composition of HTL and CTL stimulating peptides as described herein. The peptide (s) may be introduced into a mammalian host, including humans, linked to its own carrier or as a homopolymer or heteropolymer of active peptide units. Such a polymer has the advantage of increased immunological reaction and, where different peptides are used to make up the polymer, the additional ability to induce antibodies and/or cytotoxic T cells that react with different antigenic determinants of the virus. Useful carriers are well known in the art, and include, e.g., thyroglobulin, albumins such as human serum albumin, tetanus toxoid, polyamino acids such as poly(D-lysine:D-glutamic acid), influenza protein and the like. The vaccines can also contain a physiologically tolerable (acceptable) diluent such as water, phosphate buffered saline, or saline, and further typically include an adjuvant. Adjuvants such as incomplete Freund's adjuvant, aluminum phosphate, aluminum hydroxide, alum, or MONTANIDE® (Seppic, Paris, France; oil-based adjuvant with mannide oleate) are materials well known in the art. Upon immunization with a peptide composition as described herein, via injection, aerosol, oral, transdermal or other route, the immune system of the host responds to the vaccine by producing large amounts of CTLs specific for the disease associated antigen, and the host becomes at least partially immune to the disease, e.g., HBV infection, or resistant to developing chronic disease.

Vaccine compositions containing the peptides of the invention are administered to a patient susceptible to or otherwise at risk of disease, e.g., viral infection, to enhance the patient's own immune response capabilities. Such an amount is defined to be a "immunogenically effective dose." In this use, the precise amounts depend on the patient's state of health, age, the mode of administration, the nature of the formulation, etc.,. The peptides are administered to individuals of an appropriate HLA type, e.g., for vaccine compositions of peptide HBc 18–27, these will be administered to HLA-A2 individuals.

In some instances it may be desirable to combine the peptide vaccines of the invention with vaccines which induce neutralizing antibody responses to the disease, e.g., HBV, particularly to HBV envelope antigens, such as recombinant HBV env-encoded antigens or vaccines prepared from purified plasma preparations obtained from HBV-infected individuals. A variety of HBV vaccine preparations have been described, and are based primarily on HBsAg and polypeptide fragments thereof. For examples of vaccines which can be formulated with the peptides of the present invention, see generally, European Patent publications EP 154,902 and EP 291,586, and U.S. Pat. Nos. 4,565,697, 4,624,918, 4,599,230, 4,599,231, 4,803,164, 4,882,145, 4,977,092, 5,017,558 and 5,019,386, each of which is incorporated herein by reference. The vaccines can be combined and administered concurrently, or as separate preparations.

The peptides may also find use as diagnostic reagents. For example, a peptide of the invention may be used to determine the susceptibility of a particular individual to a treatment regimen which employs the peptide or related peptides, and thus may be helpful in modifying an existing treatment protocol or in determining a prognosis for an affected individual. In addition, the peptides may also be used to predict which individuals will be at substantial risk for developing chronic HBV infection.

The following examples are offered by way of illustration, not by way of limitation.

EXAMPLE 1

IDENTIFICATION OF CTL-SPECIFIC HBV EPITOPES

A line of transgenic mice which express a mouse-human chimeric class I molecule was used to define HBV core and surface antigen sequences that represent CTL-specific epitopes.

The transgenic mouse line 66 obtained from Scripps Clinic and Research Foundation expresses a chimeric class I molecule composed of the α1 and α2 domains of human HLA-A2.1 antigen and the 3 transmembrane and cytoplasmic domains of H-$_2$K$^b$. The transgenic mice were prepared as generally described in Vitiello et al., *J. Exp. Med.* 173:1007–1015 (1991), which is incorporated herein by reference. When these mice are primed in vivo with the influenza virus, they generate a CTL response that is specific for virtually the same epitopes as those recognized by human influenza-specific CTL. Thus, these transgenic animals can be used to determine HBV epitopes recognized by human T cells.

To define which sequence regions within HBV surface and core proteins represented CTL epitopes, synthetic peptides derived from the two proteins were prepared and tested for their ability to bind to human HLA-A2.1. Binding was determined by the relative capacity of different peptide concentrations to inhibit recognition of A2.1 target cells in the presence of the influenza matrix peptide 57–68 by the CTL line 219, as determined by the inhibition of release of serine esterase from the cells. The 219 line was derived from A2.1 transgenic mice and is specific for the matrix peptide 57–68 in the context of HLA-A2.1.

Briefly, peptides to be assayed for CTL epitopes were dissolved in DMSO at a concentration of 20 mg/ml. Just before the assay, peptides were diluted in RPMI 1640 buffered with 25 μM Hepes and containing 0.05% BSA (assay media). Fifty microliters of a 200 μg/ml, 66 μg/ml, or 22 μg/ml of peptide solution were added to wells of 96 round-bottomed plates containing 4×10$^5$ Jurkat A2.1/K$^b$ cells in a volume of 50 μl of assay media. Plates were incubated for 30 min. at 37° C. Fifty μl of 2.5 μg/ml solution of the index peptide (matrix peptide 57–68 from PR8 influenza virus) were then added to the cells, followed by 50 μl containing 5×10$^4$ line 219 CTL, where the concentration of index peptide used was chosen as that which induced 75% serine esterase release from CTL 219, as determined by titration of the peptide. After 4 hours incubation at 37° C., plates were centrifuged for 5 min. at 1000 RPM, and 20 μl supernatant transferred to flat-bottomed 96-well plates. Esterase activity in the supernatant was measured by adding 180 μl of a reaction mixture consisting of 0.2M TrisHCl pH 8.1, 2.0×10$^{-4}$ N-benzyloxycarbonyl-L-Lysine thiobenzyl ester (BLT) and 2.2×10$^{-4}$ M dithiobis (nitrobenzoic acid). Plates were incubated for 1 hour at 37° C. and absorbance read at 412 nm. Percent inhibition was calculated by the following formula:

% inhibition=

$$100 - \frac{A_{412}(\text{test} + \text{index})\text{peptide} - A_{412} \text{ test peptide alone}}{A_{412} \text{ index peptide} - A_{412} \text{ no peptide}} \times 100$$

Those peptides which bound to A2.1 and caused more than 24% inhibition of serine esterase release by the cells were assayed in vitro for the ability to restimulate a CTL response from splenocytes derived from HBV primed A2.1 transgenic mice. (Sette, A. et al., *J. Immunol.* 147:3893 (1991)). HBV priming was performed by injecting A2.1 spleen cells "loaded" with HBV virus as described by Carbone and Bevan, *J. Exp. Med.* 171:377–387 (1990).

Briefly, red blood cell depleted splenocytes were suspended in 0.4 ml of a solution composed of 200 μl of HBV purified virus and 200 μl of a 2×hypertonic solution (0.5 M sucrose, 10% w/v polyethylene glycol 1000, 10 mM Hepes, pH 7.2, in RPMI 1640 medium), for 10 min. at 37° C. The cell suspension was then rapidly diluted in prewarmed hypotonic media (60% HBSS and 40% water), incubated for 2 min. at 37° C., pelleted, washed twice in HBSS and irradiated (1,000 rad.). Mice were then injected with $5.0 \times 10^6$ loaded cells in a volume of 200 µl. Mice were boosted with HBV-loaded spleen cells 10 days later.

After about 2 weeks, spleen cells from primed mice ($5 \times 10^6$ cells/well in 24 well plates) were cultured with 4 different mixtures of syngeneic irradiated (3000 rads) LPS blasts ($2 \times 10^6$ cells/well) that had been independently coated with 13 different peptides. Coating was achieved by incubating aliquots of $25 \times 10^6$ LPS blasts in tubes each with 100 µg of one of the 13 HBV synthetic peptides in one mL for 1–2 hrs at 37° C.; the contents of the different tubes were then pooled to give 4 mixtures.

| Mixture No. | Peptide No. | Peptide Location |
|---|---|---|
| 1 | 800.04 | HBenv47–63 |
|   | 802.01 | HBc11–27 |
|   | 802.06 | HBc162–176 |
| 2 | 801.02 | HBenv141–157 |
|   | 799.02 | HBenv194–213 |
|   | 802.03 | HBc91–110 |
| 3 | 799.09 | HBenv329–348 |
|   | 799.10 | HBenv349–368 |
|   | 802.04 | HBc111–125 |
| 4 | 799.04 | HBenv234–253 |
|   | 799.05 | HBenv246–265 |
|   | 799.08 | HBenv309–328 |
|   | 800.05 | HBenv63–77 |

The mixture of cells was washed once, diluted at the required concentration and plated. The medium used for the cultures was RPMI 1640 supplemented with 10% FCS, 50 µg/ml gentamicin, 2 mM glutamine and $5 \times 10^{-5}$ M 2-mercaptoethanol (R10). After nine days, effector cells were assayed for cytotoxicity against Jurkat $A_2/k^b$ target cells in the presence of different peptide mixtures corresponding to those used in the cultures. The results obtained are shown in FIG. 1 panels, A through D. The effector cells ($0.2 \times 10^6$ cells/well) obtained from these cultures were restimulated with irradiated (20,000 rads), peptide-coated Jurkat $A2/K^b$ cells ($0.2 \times 10^6$ cells/well) in the presence of $3 \times 10^6$ feeder cells/well (C57BL/6 irradiated spleen cells) in R10 supplemented with 5%-rat ConA supernatant. After 6 days, these effector cells were assayed for cytotoxicity against $^{51}$Cr labeled Jurkat $A_2/K^b$ target cells in the presence of the 13 individual peptides. Peptides that induced CTL lysis of Jurkat $A_2/K^b$ target cells above background (FIG. 1, panels E through H) i.e., HBenv 47–63, HBc 11–27 (panel E) HBenv 141–157, HBenv 194–213, HBc 91–110 (panel F), HBenv 329–348 and 349–368 (panel G) and HBenv 309–328 (panel H) were independently used to restimulate the effector cells generated with the peptide mixtures. After 6d in culture, the effector cells were tested for cytotoxicity against $^{51}$Cr Jurkat $A_2/K^b$ cells in the presence of the peptide used for the restimulation (FIG. 1). The set of experiments, outlined in this example allow us to determine that HBV peptides HBc 11–27 (FIG. 1 panels A,E; FIG. 2 panel J) HBc 91–110 (FIG. 1 panels B,F; FIG. 2 panel M), HBenv 329–348 (FIG. 1 panels C,G; FIG. 2 panel N) HBenv 349–368 (FIG. 1 panels C,G; FIG. 2 panel 0) and HBenv 309–328 (FIG. 1 panels D,H; FIG. 2 panel P) clearly represent CTL epitopes.

EXAMPLE 1A

INDUCTION OF OVALBUMIN-SPECIFIC CTL RESPONSE IN MICE

B6 mice were injected with 10, 50, or 200 µg of ovalbumin in HBSS intravenously, intraperitoneally and subcutaneously with 10, 50, 200 µg ovalbumin subcutaneously in IFA. Ten days later, splenocytes from primed animals were stimulated in vitro with irradiated EG7 cells (EL-4 cells transfected with OVA). Six days later, the effector cells were tested for cytolytic activity against $^{51}$Cr labelled EL-4 and EG7 cells. No CTL activity was induced by injection of ovalbumin in HBSS either intravenously or interperitoneally. Some CTL induction was seen at the 200 µg dose for subcutaneous injection of ovalbumin in HBSS. Strong CTL in vivo induction was seen when ovalbumin was administered with IFA, optimal induction occurred with the 10 µg dose given subcutaneously.

EXAMPLE 2

INDUCTION OF A2.1-RESTRICTED CTL BY SUBCUTANEOUS PRIMING WITH PURIFIED HBV IN INCOMPLETE FREUND'S ADJUVANT (IFA)

Injection of ovalbumin (OVA) in IFA subcutaneously induces an ovalbumin-specific CTL response in mice, while injection of OVA either i.v. or i.p. generally does not lead to the generation of CTL. This technique was used to induce HBV-specific CTL in A2.1 transgenic mice.

Priming and In Vitro Restimulation

A2.1/$K^b$ transgenic mice were injected with 100 microliters of an emulsion of purified HBV virus in incomplete Freund's adjuvant (IFA). This emulsion was prepared by mixing purified HBV (1 mg protein/ml) diluted 1:5 in HBSS with an equal volume of IFA. Seven days after priming, splenocytes ($5 \times 10^6$ cells/well in a 24 well plate) obtained from these animals were restimulated with syngeneic irradiated LPS blasts ($2 \times 10^6$/well) coated with each of the following peptides:

| | | | |
|---|---|---|---|
| 799.09 | HBenv 329–348 | 802.03 | HBc 91–110 |
| 875.20 | HBenv 335–343 | 883.02 | HBc 92–101 |
| 875.21 | HBenv 338–347 | 883.03 | HBc 93–102 |
| 799.10 | HBenv 349–368 | 875.15 | HBc 18–27 |
| 884.01 | HBenv 348–357 | 875.18 | HBc 107–115 |
| 884.02 | HBenv 349–358 | 875.19 | HBc 139–148 |

These peptides were chosen because: 1) They had been defined as containing CTL epitopes in Example I (peptides 799.10, 799.09, 802.03); 2) they represent truncations of peptides defined in Example I that are recognized by the CTL raised against the larger epitopes (i.e., peptides 875.15, 884.02, 883.02, 883.03); or 3) they contain the A2.1 binding motif as described by Falk et al. (*Nature* 351:290–296 (1991)), i.e., leucine or methionine in position 2, and either leucine or valine in position 9 or valine in position 10, (i.e., peptides 884.01, 875.20, 875.21, 875.18 and 875.19). Coating was achieved by incubating 50 µg of each individual peptide with $12 \times 10^6$ LPS blasts in a volume of 0.4 ml of RPMI medium supplemented with 10% FCS for 1 h at 37° C. The cells were washed once. After 6 days, effector cells were assayed for cytotoxicity against $^{51}$Cr labelled Jurkat A2/$K^b$ cells in the presence of the appropriate peptides. The results are shown in FIG. 3.

These effector cells ($0.2 \times 10^6$ cells/well) were restimulated at weekly intervals. For the first restimulation, peptide-coated LPS blasts were used, followed by peptide-coated Jurkat A2.1/$K^b$ cells. Six days after restimulation, effector cells were assayed for cytotoxicity against $^{51}$Cr labelled Jurkat A2/$K^b$ target cells in the presence of the appropriate peptides. The results obtained are shown in FIG. 4.

Peptides clearly able to induce in vitro CTL from splenocytes of HBV-primed mice are FIGS. 3 and 4, panel A: HBc 18–27; FIGS. 3 and 4, panel B: HBenv 349–368; FIGS. 3 and 4, panel D: HBenv 349–358; FIGS. 3 and 4, panel F: HBenv 329–348; FIGS. 3 and 4, panel I: HBc 91–110; FIGS. 3 and 4, panel J: HBc 92–102; and FIGS. 3 and 4, panel K: HBc 93–102. Truncation peptides recognized by CTL raised against the larger peptide and as such should contain at least part of a CTL epitope are: FIGS. 3F, 4F: HBenv 335–343 and HBenv 338–347.

EXAMPLE 2A

OTHER HBV CTL EPITOPES

The following peptides were identified following procedures disclosed in pending U.S. patent applications Ser. No. 08/159,339 and 08/073,205, incorporated herein by reference.

| CTL Epitopes | Position | Sequence | Seq ID No. |
| --- | --- | --- | --- |
| HBV POL | 561 | FLLSLGIHL—COOH | 35 |
| HBV POL | 61 | GLYSSTVPV—COOH | 106 |
| HBV POL | 411 | NLSWLSLDV—COOH | 107 |
| HBV POL | 491 | HLYSHPIIL—COOH | 108 |

EXAMPLE 3

SYNTHESIS OF PEPTIDES

Peptides were synthesized on an Applied Biosystems (Foster City, Calif.) 430A peptides synthesizer using Fmoc protected amino acids and 2-(1H-Benzotriazol-1-yl)-1,1,3,3-tetramethyluronium hexafluorophosphate (HBTU) esters for amino acid activation. Each amino acid was routinely triple coupled. Fmoc protected amino acids and Hydroxybenzotriazole were purchased from Burdick and Jackson. HBTU was purchased from Richelieu Biotechnologies (St-Hyacinthe, Canada). Piperidine and trifluoroacetic acid, acetic anhydride, and ethanedithiol were purchased from Sigma Chemical Corporation.

a. Peptide Phe-Leu-Pro-Ser-Asp-Phe-Phe-Pro-Ser-Val-OH [Seq. ID No. 4]

L-Valine coupled to Sasrin® resin (Bachem Biosciences) was loaded into the peptide synthesis reaction vessel and washed one time with N-methylpyrolidone (NMP). The following operations were then sequentially performed:

1. The Fmoc protecting group was removed by treatment of the resin bound amino acid with 25% piperidine in NMP.
2. The resin was washed 5 times with NMP.
3. A mixture containing Fmoc-serine, diisopropylethylamine, HBTU and NMP was added to the reaction vessel and allowed to react for 30 minutes, under vortex agitation.
4. The solvent was drained, and the resin was washed three times with NMP.
5. Steps (3) and (4) were repeated two more times.
6. The resin was washed four more times with NMP.

Steps 1–6 were repeated for each amino acid of the peptide. Following the final coupling cycle, the resin-bound peptide was deproteced by reaction with 25% piperidine in NMP, washed 7 times with NMP, and washed 2 times with dichloromethane. The resin was dried in vacuo for 24 hours. The peptide was cleaved from the Sasrin® resin by treatment with trifluoroacetic acid containing 2.5% ethanedithiol and 5% water. The polystyrene resin was separated from the trifluoroacetic acid solution by filtration. Trifluoroacetic acid was removed by evaporation in vacuo. The crude peptide was triturated with diethylether and dissolved in water. The water was removed by lyophilization. The peptide was then purified by reverse phase HPLC on a $C_8$ column (VYDAC) using a gradient of acetonitrile, water, each containing 0.1% TFA as modifier.

b. Peptide $(Pal)_2$-Lys-Ser-Ser-Phe-Leu-Pro-Ser-Asp-Phe-Phe-Pro-Ser-Val-OH [Seq. ID No. 109]

The resin bound peptide described in section a was extended by the addition of two serine residues according to the above described procedure. The following operations were then performed:

1. The Fmoc protecting group was removed by treatment of the resin bound amino acid with 25% piperidine in NMP.
2. The resin was washed 5 times with NMP.
3. Bis-Fmoc-Lysine was converted to the corresponding symmetrical anhydride by treatment with diisopropylcarbodiimide in NMP. The resin bound peptide was allowed to react with the resulting anhydride.
4. The resin was washed 5 times with NMP.
5. The Fmoc protecting group was removed by treatment of the resin bound amino acid with 25% piperidine in NMP.
6. Palmitic acid was reacted with hydroxybenzotriazole and diisopropylcarbodiimide in NMP. The resin bound peptide was allowed to react with the resulting solution.
7. The resin was washed 5 times with NMP.

Finally, the peptide was cleaved from the resin as described above.

c. Peptide Gln-Tyr-Ile-Lys-Ala-Asn-Ser-Lys-Phe-Ile-Gly-Ile-Thr-Glu-Phe-Leu-Pro-Ser-Asp-Phe-Phe-Pro-Ser-Val-OH [Seq. ID No. 110]

The resin bound peptide described in section a was chain extended by the addition of Glu, Thr, Ile, Gly, Ile, Phe, Lys, Ser, Asn, Ala, Lys, Ile, Tyr, and Gln residues, according to the procedure described in Section a. Cleavage and purification were performed as described above.

d. Peptide Gln-Tyr-Ile-Lys-Ala-Asn-Ser-Lys-Phe-Ile-Gly-Ile-Thr-Glu-Ala-Ala-Ala-Phe-Leu-Pro-Ser-Asp-Phe-Phe-Pro-Ser-Val-OH [Seq. ID No. 111]

The resin bound peptide described in section a was chain extended by the sequential addition of Ala, Ala, Ala, Glu, Thr, Ile, Gly, Ile, Phe, Lys, Ser, Asn, Ala, Lys, Ile, Tyr, and Gln residues, according to the procedure described in section a. Cleavage and purification were performed as described above.

e. Peptide A6-Gln-Tyr-Ile-Lys-Ala-Asn-Ser-Lys-Phe-Ile-Gly-Ile-Thr-Glu-Ala-Ala-Ala-Phe-Leu-Pro-Ser-Asp-Phe-Phe-Pro-Ser-Val-OH [Seq. ID No. 112]

The resin bound peptide described in Section d was acetylated by reaction with acetic anhydride in NMP. Cleavage and purification were performed as described above.

EXAMPLE 4

INDUCTION OF CTL BY COMBINING CTL AND T-HELPER EPITOPES

This example describes experiments which define the relative in vivo HBV-specific CTL priming efficiency of peptides expressing HBV CTL epitopes alone, CTL epitopes mixed with peptides containing T helper epitopes or CTL epitopes physically linked to T helper epitopes.

Transgenic mice (HLA-A2.1/$K^b$) were primed subcutaneously (base of tail) with 100 μg of peptide 875.23 ($Ia^b$-restricted helper epitope HBc 128–140 TPPAYRPPNAPIL [Seq ID No. 113]) in complete Freund's adjuvant (CFA). Nine days later each of the following peptides were injected subcutaneously into two unprimed and two helper-primed mice, 100 μg/mouse in incomplete Freund's adjuvant (IFA).

Figure 7:
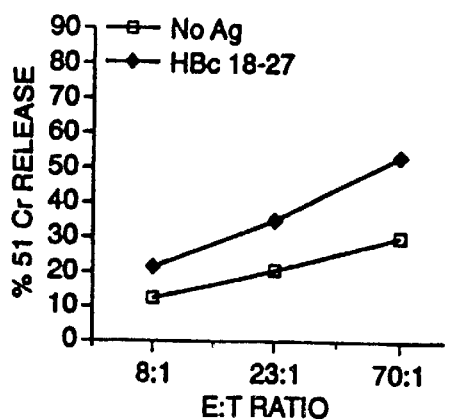
FIG. 7 illustrates that HBc18–27-specific CTL response was detected in 50% of the mice primed with HBc T helper peptide (875.23) mixed with HBc CTL inducing peptide (875.15) at a 1 to 1 ratio. The experimental protocol was similar to that described in FIGS. 5 and 6.
Figure 8:
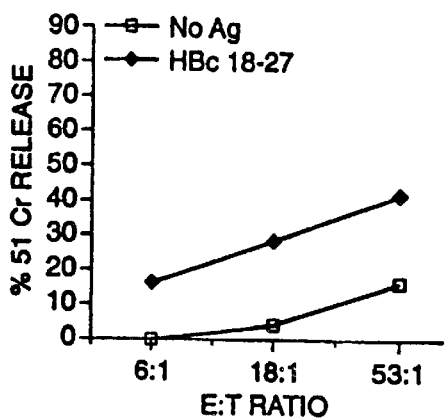
FIG. 8 illustrates that HBc-specific (875.15) CTL activity was detected in mice primed with peptide 902.01 in which the HBc T helper and CTL inducing peptide were linked via a peptide bond. Experimental protocol was similar to that in FIGS. 5 and 6.
Figure 9:
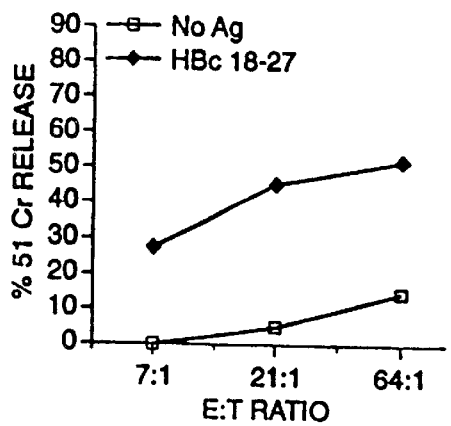
FIG. 9 illustrates that the greatest HBc18–27 (875.15)-specific CTL activity was detected in mice primed with peptide 902.02 in which the HBc T helper and CTL epitopes were linked via peptide bonds using an exemplary spacer such as alanine-alanine-alanine. Protocol was similar to that in FIGS. 5 and 6.

FIGS. 7, 8 and 9, were restimulated in vitro using HBcAg 18–27-coated JA2.1/$K^b$ stimulator cells. Six days later, effector cells were assayed for cytotoxicity and the cell lines that contained HBcAg 18–27-specific cytotoxic activity were further restimulated. Six days later, these cell lines were tested for cytotoxic activity on $^{51}$Cr labeled Jy S1 target cells in the absence or presence of HBcAg 18–27 and

| Peptide | T Helper (HBc 128–140) | CTL (HBc 18–27) | Seq ID No. |
|---|---|---|---|
| 1. 875.23 | TPPAYRPPNAPIL | | 113 |
| 2. 875.15 | | FLPSDFFPSV | 4 |
| 3. 875.23 + 875.15 | TPPAYRPPNAPIL + | FLPSDFFPSV | 113 & 4 |
| 4. 902.01 = | TPPAYRPPNAPILFLPSDFFPSV-NH$_2$ | | 114 |
| 5. 902.02 | TPPAYRPPNAPILAAAFLPSDFFPSV-NH$_2$ | | 115 |
| 6. No peptide | | | |

Three weeks after priming with the CTL epitope, splenocytes were in vitro restimulated with LPS blasts coated with HBc 18–27 (coating was achieved by incubating 30×10$^6$ LPS blasts with 100 μg of HBc18–27 in one ml of medium; after 1–2 hr at 37° C., the cells were washed). After 6 days, effector cells were assayed for lytic activity against $^{51}$Cr labelled Jurkat $A_2/K^b$ target cells in the presence or absence of HBc18–27.

Figure 5:
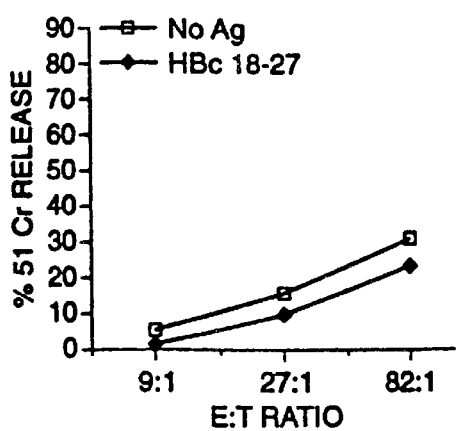
FIG. 5 illustrates that no HBc18–27-specific CTL response is detected in mice primed with the HBc 875.23 T helper epitope alone. Animals were primed subcutaneously with 100 µg of 875.23 (T helper epitope) in Complete Freund's Adjuvant (CFA) followed 9 days later (subcutaneously) with IFA alone. Splenocytes were removed 3 weeks later, cultured for 6 days in the presence of LPS-blasts that had been incubated with the CTL epitope (875.15), 100 µg for 2 hrs before being washed and added to the culture as a source of antigen presenting cells. The presence of HBc 18–27 (875.15)-specific CTL was determined using a standard 6 hr $^{15}$Cr release assay with Jurkat A2.1/$K^b$ cells as targets.
Figure 6:
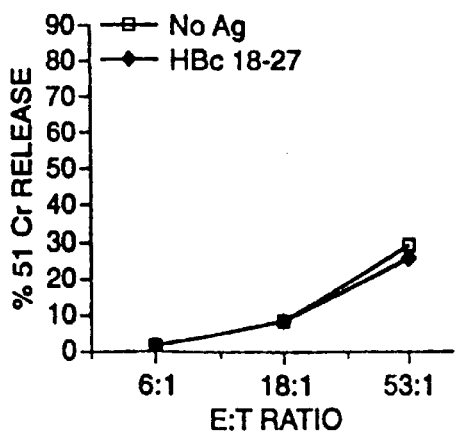
FIG. 6 illustrates that no HBc 18–27-specific CTL response was detected when mice were primed with HBc18–27 (875.15) in IFA. Experimental protocol was similar to that described in FIG. 5, except that mice received 100 µg of peptide 875.15 subcutaneously in IFA rather than IFA alone for in vivo CTL priming.
Figure 10A:
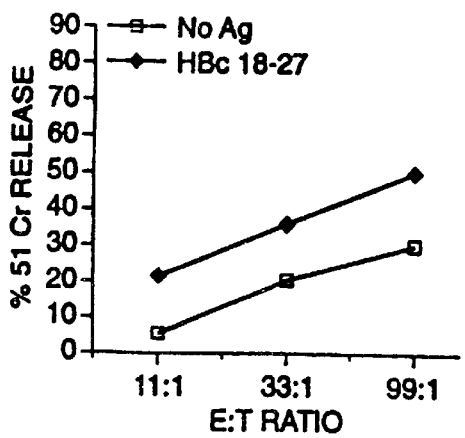
FIGS. 10A–10B illustrate that previous priming of helper T cells was not required for in vivo priming of HBc 18–27-specific CTL responses using peptide 902.01 and 902.02. CTL response is shown from animals primed subcutaneously with peptide 902.01 (FIG. 10A) or 902.02 (FIG. 10B) alone without the previous priming with peptide 875.23 in CFA.
Figure 10B:
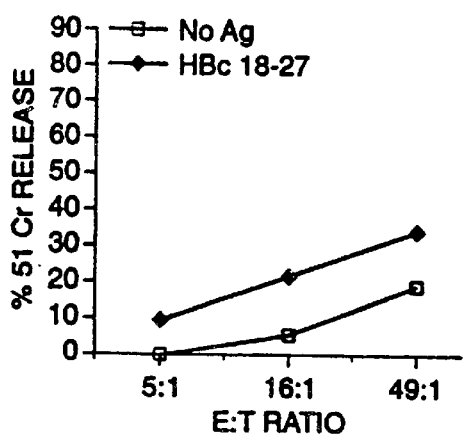

The results showed that in 50% of the animals studied in which the T helper and CTL epitope peptides were simply mixed (i.e., not linked) and administered in an immunizing dose, induction of some detectible antigen-specific CTL activity above the level of background killing was seen. An example of the response detected is shown in FIG. 7. Surprisingly, when animals were primed with the T helper epitope linked to the CTL epitope, 100% showed evidence of specific CTL priming (FIG. 8), the magnitude of which was greater than that detected when the epitopes were administered non-linked (FIG. 7). Quite unexpectedly, as shown in FIG. 9, it was found that linking the T helper and CTL epitopes via an alanine-alanine-alanine spacer (i.e., T helper-AAA-CTL) resulted in the induction of specific CTL activity greater than that detected by linking the T helper and CTL determinants alone. Priming with the T helper peptide or CTL peptide alone did not induce HBc-specific CTL (FIGS. 5 and 6). Also, prior immunization of animals to induce T helper-specific immunity did not appear to be essential for priming for CTL using either the T helper and CTL mixture or the T helper-CTL conjugate, since immunization was detected when naive animals were primed with the appropriate conjugate (FIGS. 10A and B).

EXAMPLE 4A

RECOGNITION OF GENERATION OF ENDOGENOUS PROCESSED ANTIGENS AFTER PRIMING

This example discloses that CTL inducted by in vivo priming with peptide (as disclosed in Example 4) recognize endogenously synthesized antigens.

A fraction of the effector cells from the procedure disclosed in Example 4 whose CTL function is represented in on $^{51}$Cr labeled Jy core target cells, as demonstrated in the following table.

CTL lines obtained from animals primed with HBcAG 18–27 peptide derived recognize endogenously synthesized HBc antigen.

| Animal | In vivo Primed | | Jv S$_1$ | | Jy Core | |
|---|---|---|---|---|---|---|
| No. | Day 0 | Day 9 | E:T | NoAg | 875.15 | |
| H21 | — | 902.01 | 0.1:1 | 1 | 43 | 3 |
| | | | 0.5:1 | 3 | 66 | 2 |
| | | | 2:1 | 6 | 73 | 9 |
| | | | 8:1 | 11 | 74 | 1.5 |
| H5-2 | — | 902.02 | 0.3:1 | 2 | 55 | 21 |
| | | | 1:1 | 1 | 78 | 35 |
| | | | 4.5:1 | 5 | 77 | 44 |
| | | | 18:1 | 12 | 82 | 54 |
| H6-3 | — | 875.15 +875.23 | 0.4:1 | 4 | 67 | 9 |
| | | | 1.5:1 | 6 | 78 | 17 |
| | | | 6:1 | 11 | 75 | 23 |
| | | | 24:1 | 18 | 79 | 29 |
| H4-6 | 875.23 | 902.01 | 0.15:1 | 2 | 29 | 9 |
| | | | 0.6:1 | 5 | 51 | 21 |
| | | | 2.5:1 | 12 | 63 | 32 |
| | | | 10:1 | 21 | 62 | 42 |
| H4-2 | 875.23 | 902.02 | 0.6:1 | 1 | 74 | 37 |
| | | | 2.5:1 | 3 | 80 | 55 |
| | | | 10:1 | 6 | 80 | 59 |
| | | | 40:1 | 14 | 77 | 63 |

All CTL lines were specific for HBcAg 18–27 and recognized Jy core albeit to a different extent. The much higher level of lysis obtained in the presence of exogenously added peptide as compared to endogenously synthesized, is explained by the relatively greater concentration of peptide that can be added exogenously. Because CTL lines derived from both animals primed with 902.02 had the highest affinity for endogenous antigen (producing a 35% and 37% specific lysis of Jy core at the E:T of 1:1 and 0.6:1, respectively), it is demonstrated that this construct, i.e., T helper epitope AAA HBcAg 18–27 possesses immunogenic characteristics suitable for induction of cells that recognize HBV infected cells.

EXAMPLE 5

INDUCTION OF A2.1-RESTRICTED CTL-SPECIFIC

FOR HBenv$_{360-368}$

Figure 11:
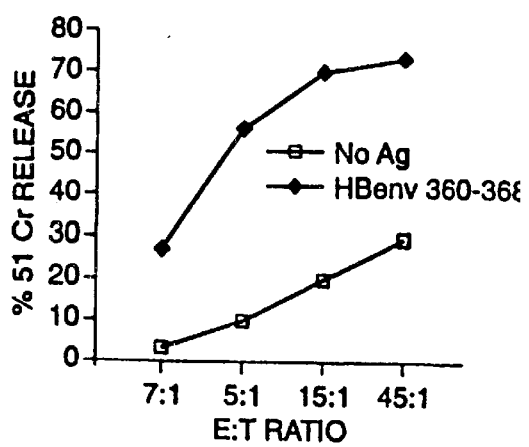
FIG. 11 illustrates the induction of HBenv$_{360-368}$ specific CTL response. A2.K$^b$ transgenic mice were injected with 100 microliters of an emulsion (IFA) of 100 mg HBenv360–368 and 100 mg HBc128–140. Three weeks later, splenocytes were restimulated with syngeneic LPS blasts coated with peptide HBenv360–368. Effector cells were assayed for cytotoxicity against $^{51}$Cr labeled Jurkat A2/K$^b$ target cells in the presence or absence of HBenv 360–368.

A2/K$^b$ transgenic mice were injected with 100 microliters of an emulsion of 100 μg HBenv$_{360-368}$ and 100 μg HBc$_{128-140}$ helper epitope in incomplete Freund's adjuvant (IFA). (This emulsion was prepared by mixing 500 μg of both peptides in PBS with an equal volume of IFA.) Twenty-one days after priming, splenocytes (5×10$^6$ cells/well in a 24-well plate) obtained from these animals were restimulated with syngeneic LPS blasts (2×10$^6$/well) coated with the peptide HBenv$_{360-368}$. These effector cells (0.2×10$^6$/well) were restimulated at weekly intervals. For the first and second restimulations, HBenv$_{360-368}$ coated LPS blasts were used, followed by HBenv$_{360-368}$ coated Jurkat A2.1/K$^b$ cells. Six days after restimulation, effector cells were assayed for cytotoxicity against $^{51}$Cr labelled Jurkat A2/K$^b$ target cells in the presence and absence of HBenv$_{360-368}$ (see FIG. 11). Therefore, HBenv$_{360-368}$ is a CTL specific epitope.

EXAMPLE 6

TESTING OF LINKED TETANUS TOXOID T HELPER AND HBc CYTOTOXIC T CELL EPITOPES FOR IN VIVO PRIMING

Transgenic mice (HLA-A2-1/kb) were primed subcutaneously (base of the tail) with 200 mg (0.07 mM) of peptide 934.02.

| Peptide | Tetanus Toxoid 830–843 T Helper Epitope | Linker | HBV core 18–27 CTL Epitope | Seq ID No. |
|---|---|---|---|---|
| 934.02 | AC-QYIKANSKFIGITE | AAA | FLPSDFFPSV | 112 |

Figure 12:
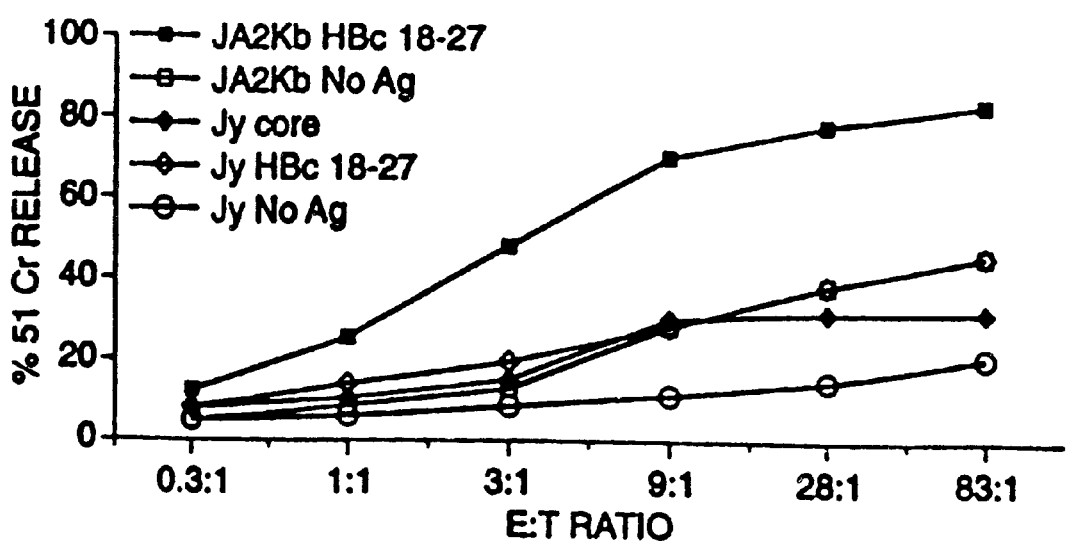
FIG. 12 illustrates the induction of a CTL response specific for HBc 18–27 by priming with a peptide containing HBc 18–27 linked to tetanus toxoid 830–843 (human helper T cell epitope). Effector cells were assayed against 51Cr labeled Jurkat A2-1/K$^b$ target cells in the present or absence of HBc 18–27; Jy target cells in the presence or absence of HBc 18–27 and Jy cells that had been transfected with HBV core.

Three weeks after priming, splenocytes were restimulated in vitro with LPS blasts coated with HBc 18–27 (as described in example I). After 7 days cells were restimulated with jurkat A2/K$^b$ cells coated with HBc 18–27 (as described in Example I)—After 6 days these effector cells were assayed for cytotoxicity against 51Cr labeled jurkat A2/K$^b$ target cells in the presence or absence of HBc 18–27, Jy target cells in the presence or absence of HBc 18–27 and Jy cells transfected with HBV core. The results, shown in FIG. 12, indicate that peptide 934.02 effectively induces CTL specific for HBc 18–27. Moreover, these CTL recognize and kill endogenously presented antigen (Jy core).

EXAMPLE 7

COMPARISON OF CTL IMMUNITY INDUCED BY PEPTIDE IMMUNIZATION

Various modifications and formulations of an antigenic CTL peptide were tested in an effort to enhance its immunogenicity. BALB/c mice were primed subcutaneously in the base of the tail with one of the following peptides or peptide mixtures:

| Number | Peptide or Peptides | Dose μM/mouse | Formulation |
|---|---|---|---|
| 932.01 | CTL (Flu NP 147–155) TYQRTRALV [Seq ID No. 116] | 0.1, 0.01 | Saline, Alum, IFA |
| 932.07 | (PAM)$_2$KSS-CTL (PAM)$_2$KSSTYQRTRALV [Seq ID No. 117] | 0.1, 0.01 | Saline, Alum, IFA |
| 932.01 + 577.01 | CTL + T helper (OVA 323–336) TYQRTRALV-ISQAVHAAHAEINE [Seq ID No. 118] | 0.1, 0.01 ea. | Saline, Alum, IFA |
| 932.07 + 577.01 | (PAM)$_2$KSS-CTL + T helper (PAM)$_2$KSSTYQRTRALV-ISQAVHAAHAEINE [Seq ID No. 119] | 0.1, 0.01 | Saline, Alum, IFA |
| 932.02 | T helper-CTL ISQAVHAAHAEINE-TYQRTRALV [Seq ID No. 120] | 0.1, 0.01 | Saline, Alum, IFA |
| 932.04 | (PAM)$_2$KSS-T helper-CTL (PAM)$_2$KSSISQAVHAAHAEINE-TYQRTRALV [Seq ID No. 121] | 0.1, 0.01 | Saline, Alum, IFA |
| 932.03 | T helper-AAA-CTL ISQAVHAAHAEINE-AAA-TYQRTRALV [Seq ID No. 122] | 0.1, 0.01 | Saline, Alum, IFA |
| 932.05 | (PAM)$_2$KSS-T helper-AAA-CTL (PAM)$_2$KSS-ISQAVHAAHAEINE-AAA-TYQRTRALV [Seq ID No. 105] | 0.1, 0.01 | Saline, Alum, IFA |

Three weeks after immunization splenocytes were removed and stimulated in vitro with the flu 147–155 peptide. CTL activity was assayed one week later using $^{51}$Cr-labeled B10.D2 fibroblasts as targets. Target cells were tested in the absence of antigen, in the presence of Flu 147–155 peptide or following infection with influenza PR8 virus.

Representative results obtained from one of four independently run experiments are summarized in the following table.

| | CTL Immunogenicity of Various Modifications and Formulations of PR8-NP 148–155 | | | | | |
|---|---|---|---|---|---|---|
| | Formulation | | | | | |
| | Saline | | Alum | | IFA | |
| Peptide | 0.01$^a$ | 0.1 | 0.01 | 0.1 | 0.01 | 0.1 |
| 932.01 | –$^b$ | – | – | – | + | +++ |
| 932.07 | ++ | + | – | – | – | – |
| 932.01 + 577.01 | – | ++ | – | – | +++ | ++ |
| 932.07 + 577.01 | + | – | – | – | – | ± |
| 932.02 | – | – | – | +++ | +++ | +++ |
| 932.04 | +++ | +++ | +++ | +++ | +++ | +++ |
| 932.03 | – | – | – | ± | +++ | ++ |
| 932.05 | +++ | +++ | +++ | +++ | +++ | +++ | a = Dose (μM/mouse
b = CTL immunogenicity of various modifications and formulations of NP 148–155 (nucleoprotein of PR8 influenza virus).
Each symbol represents the result obtained from spleen cells derived from a single Balb/c mouse and reflects the effector to target ratio (E:T) required to induce 40% antigen specific lysis of $^{51}$Cr labeled B10D2 target cells in the presence of ND$_{148-155}$ peptide;
+++ E:T below 10:1;
++ E + T between 10 + 1 and 30:1;
+ E:T greater than 30:1;
– not achieved at any E:T tested.

Thus, the results were as follows:

IFA Formulation:

The HTL-CTL linked peptides either lipidated (i.e., 932.04 and 932.05) or unlipidated (932.02 and 932.03) were all very active, inducing good CTL activity in all animals at both injection doses. The mixture of HTL (577.01) and CTL (932.01) peptides also induced CTL activity in all animals injected. The CTL peptide (932.01) demonstrated good activity at the 100 nmoles dose, however, only one out of four animals responded at the 10 nmoles dose. The lipidated CTL peptide (932.07) was completely inactive but some activity, albeit low, was observed when peptide 932.07 was mixed with the HTL peptide (577.01).

Saline Formulation:

The $PAM_2$-HTL-CTL linked peptides (932.04 and 932.05) induced good CTL activity in all animals injected and were far superior to all other peptide or peptide combinations tested. The unlipidated versions of those peptides (932.02 and 932.03) were totally ineffective at the 10 nmoles dose and only marginally active at the 100 nmoles dose underlying the importance of peptide lipidation for priming activity of saline formulations. For the other peptide combinations tested lipidation appeared to affect activity in the opposite direction as it did in IFA in that the CTL peptide (932.01) was completely inactive but its lipidated version (932.07) induced CTL activity in some of the animals injected. The activity of both peptides improved when mixed with the HTL peptide.

Alum Formulation:

The results obtained were similar to the ones obtained with peptides formulated in saline with the exception of peptide 932.07 that was inactive when injected in alum.

Accordingly, the constructs ($PAM_2$KSS-T helper-CTL and $(PAM)_2$KSS-T helper-AAA-CTL were superior when injected in saline or Alum compared to all of the other combinations. The peptides T helper-CTL and T helper-AAA-CTL were superior to mixing the T helper+CTL (i.e., non-linked) and worked well in IFA, but not well in saline or Alum. Thus, for vaccine development, linking the $(PAM)_2$KSS to a T helper peptide which is linked to the CTL peptide appears to be advantageous for inducing CTL immunity.

EXAMPLE 8

Definition Of The Minimal Optimal Sequence With The CTL Peptide Epitope 799.09

Figure 13A:
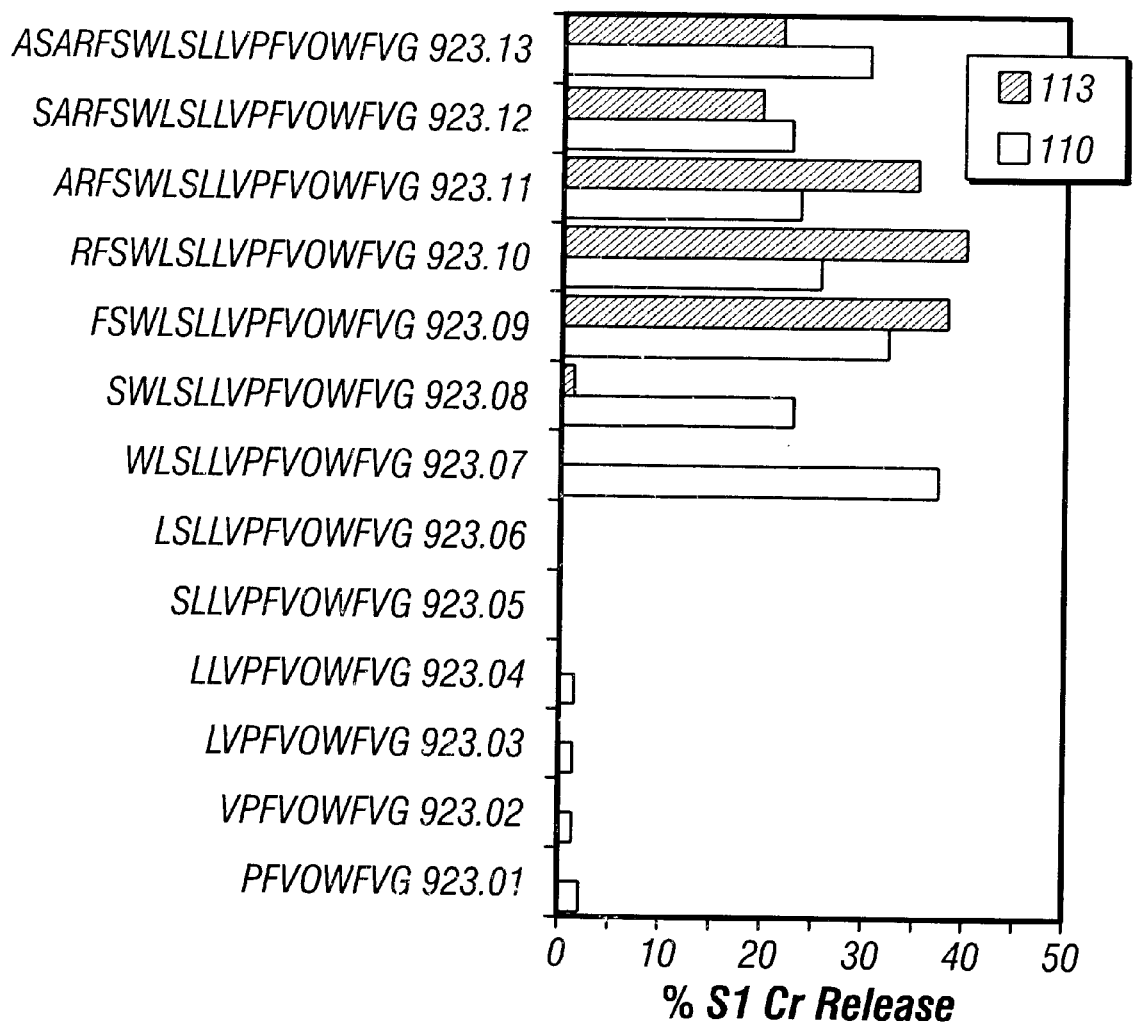
FIGS. 13A–13B collectively illustrate the minimal sequence for CTL recognition within HBV env 329–348 peptide (799.09). CTL lines 110 and 113 were derived from splenocytes obtained from A2Kb transgenic mice primed subcutaneously with HBV virus in IFA and in vitro activated with 799.09 coated stimulator cells. 799.09 specific CTL lines 110 and 113 were assayed for lytic activity in a 6 hr 51Cr release assay using JA2Kb cells as targets in the presence of 799.09 peptide truncations (FIG. 13A=799.09 N-terminus truncations.
Figure 13B:
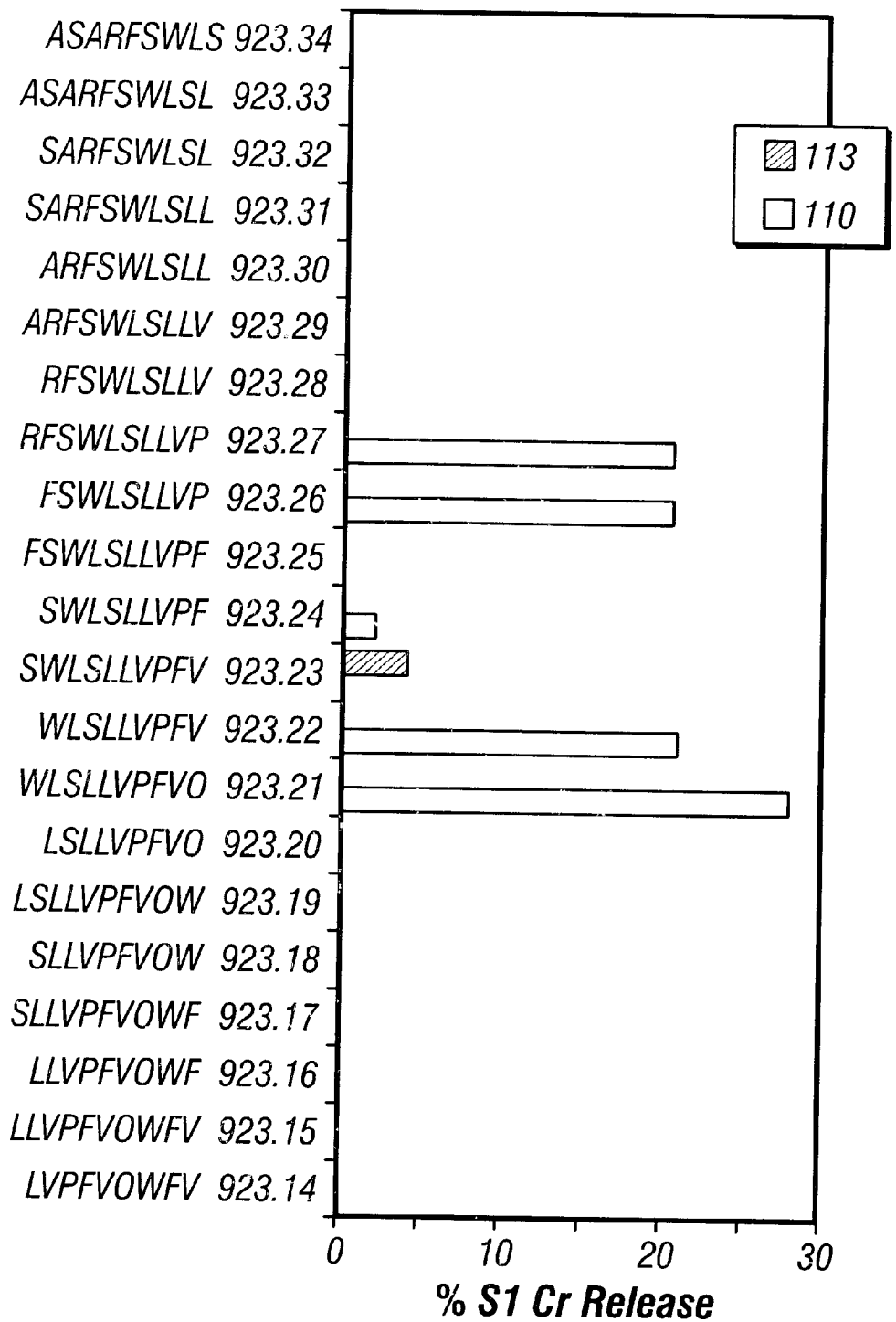
Figure 14A:
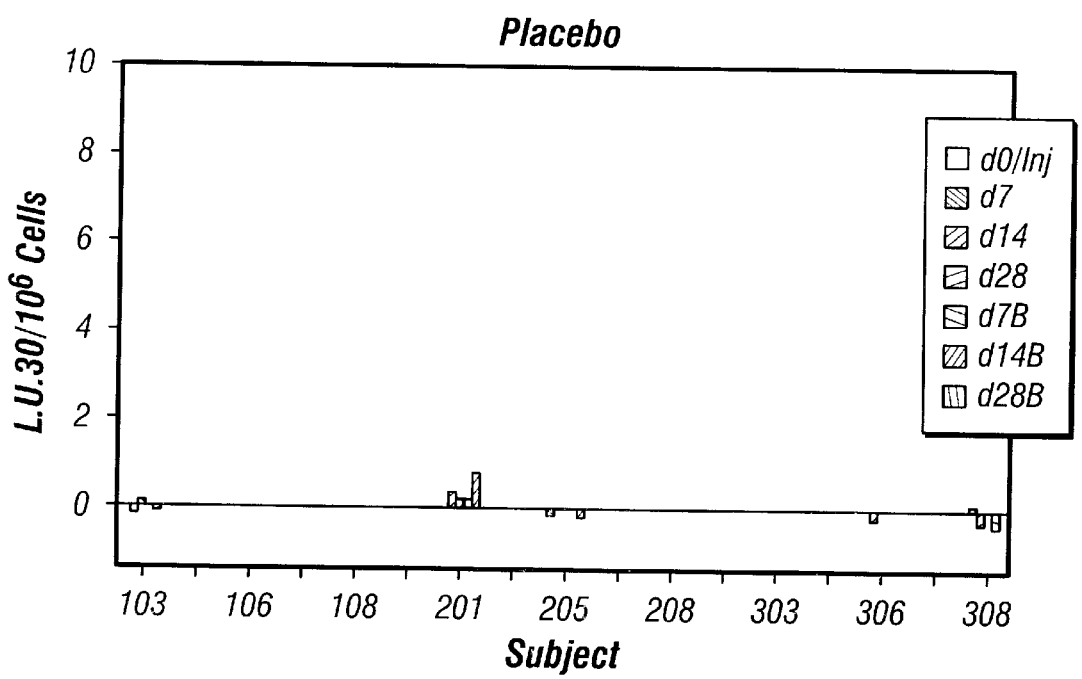
FIGS. 14A–14D show the HBc18–27 specific CTL response (d7 assay) from subjects immunized with placebo or CY-1899. The CTL response against HBc18–27 was assessed by culturing 4×10$^6$ PBMC/well in 24 well plates in the presence of HBc18–27 peptide. On day three and 6 after initiation cultures were fed with 10 U/ml IL-2 (final concentration). On day 7, part of the wells (2–3) were harvested and CTL activity was measured using $^{51}$Cr-labeled 0.221 A$_2$ target cells in the absence or presence of HBc18–27 peptide and in the presence of a 20 fold excess of K562 cells (K562 cells were added in order to decrease background lysis caused by NK cells). The data are expressed in lytic units/10$^6$ cells were one lytic unit is defined as the number of lymphocytes required to achieve 30% lysis of 10000 0.221 A$_2$ during a 6 hour assay. Each bar represents the specific CTL activity (i.e. in the present of peptide—in the absence of peptide).
Figure 14B:
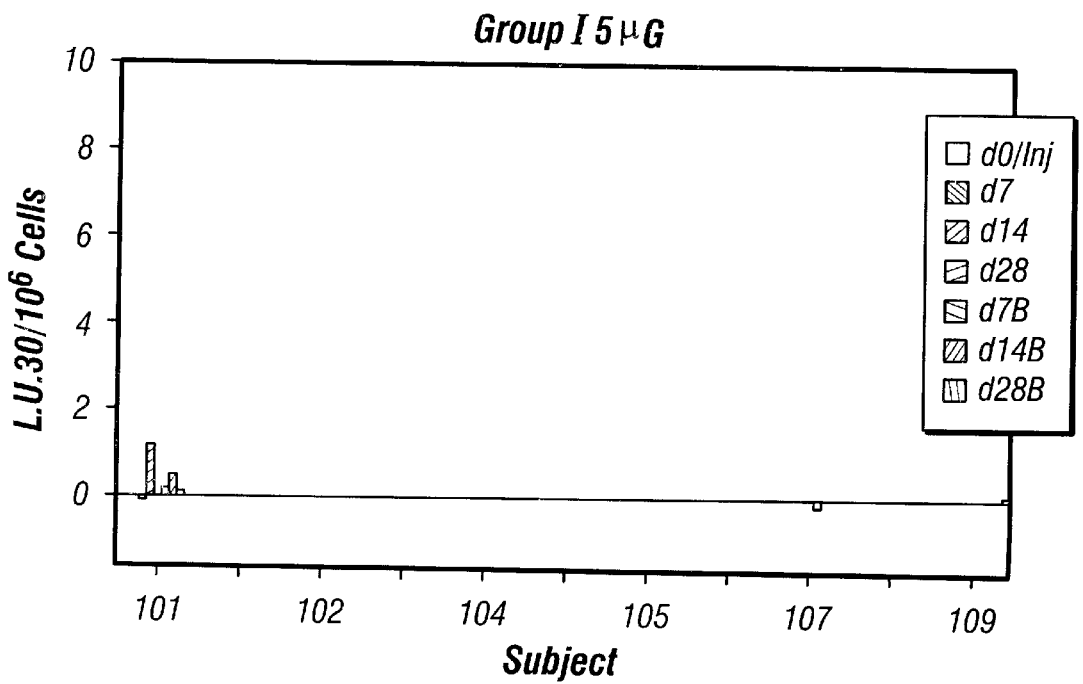
Figure 14C:
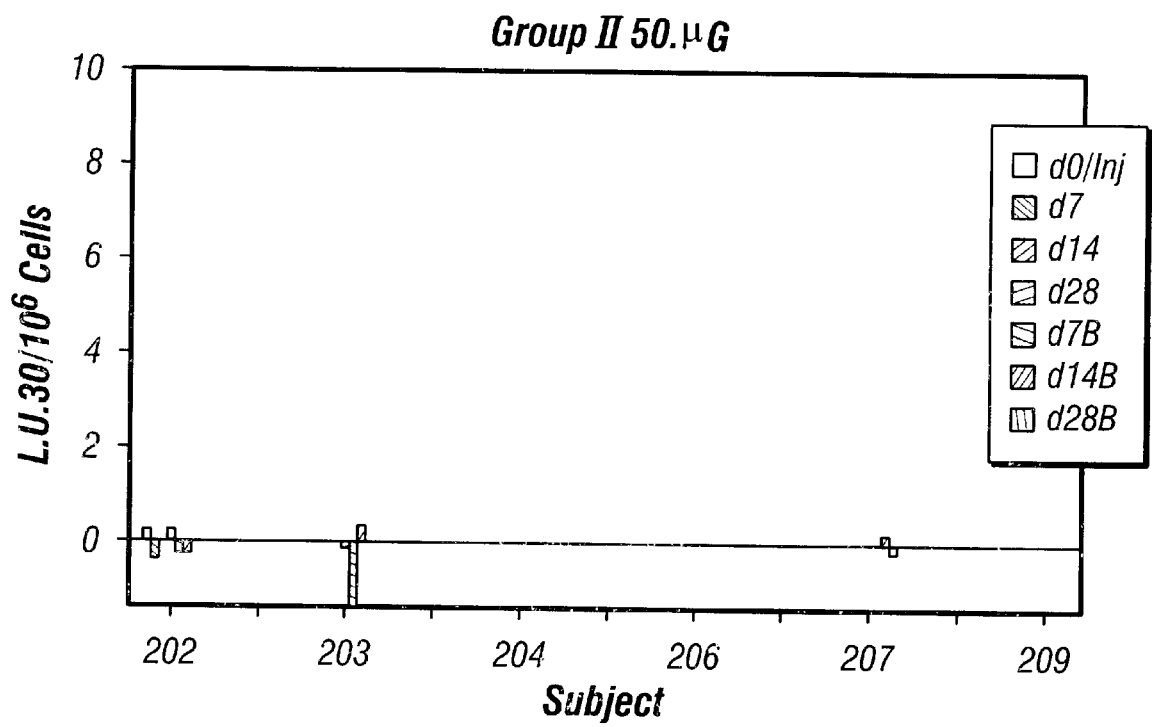
Figure 14D:
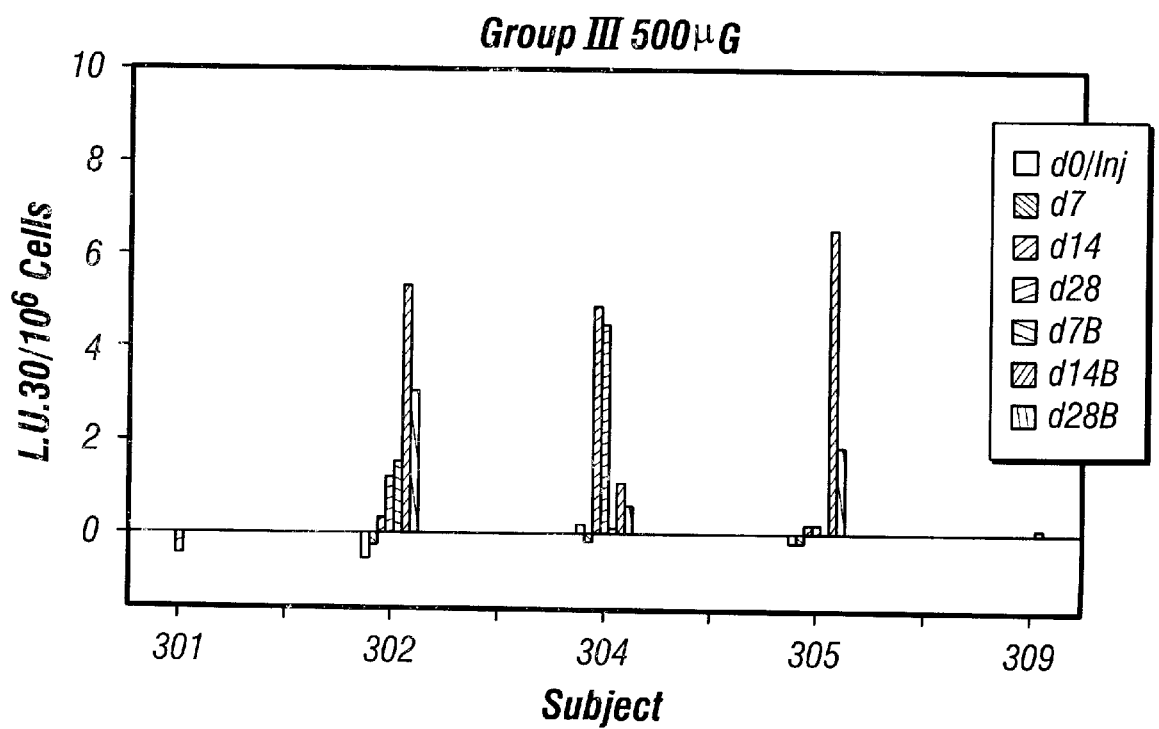
Figure 15A:
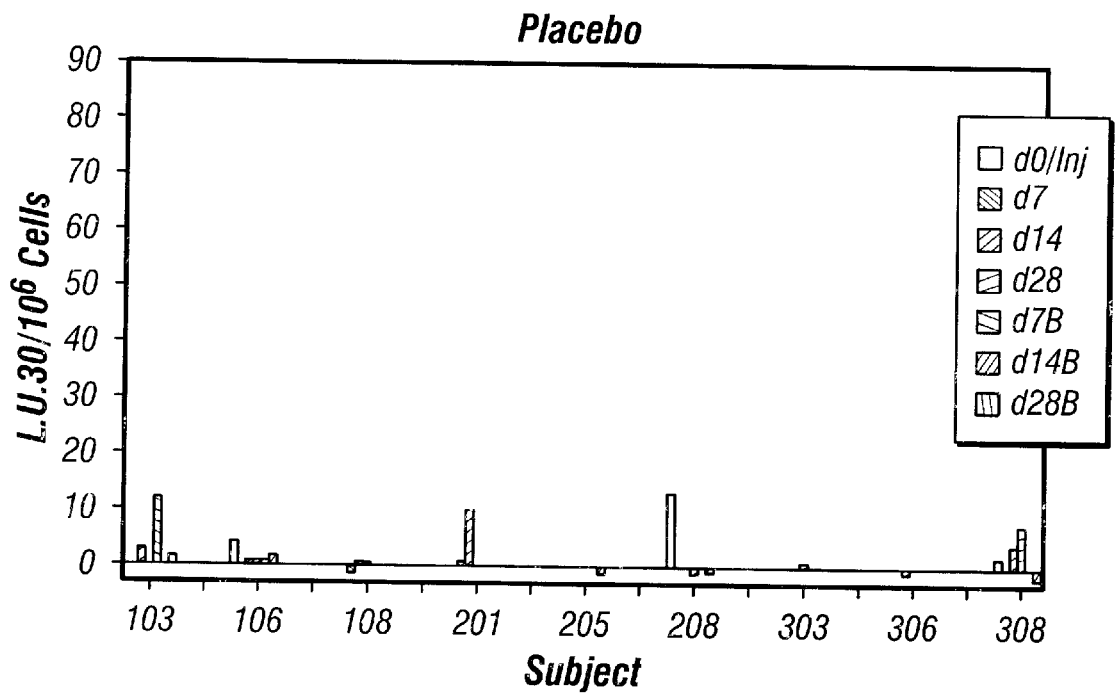
FIGS. 15A–15D show the HBc18–27 specific CTL response (d14 assay) from subjects immunized with placebo or CY-1899. On day 7 after initiation of cultures (see FIGS. 1A–1H), the remaining wells (2–3) were harvested and cells were restimulated with HBc18–27 peptide-coated autologous adherent cells. Cultures were fed with 10 U/ml IL-2 on day 9 and thereafter as needed. CTL activity was assayed on day 14 using the procedure described in FIGS. 1A–1H.
Figure 15B:
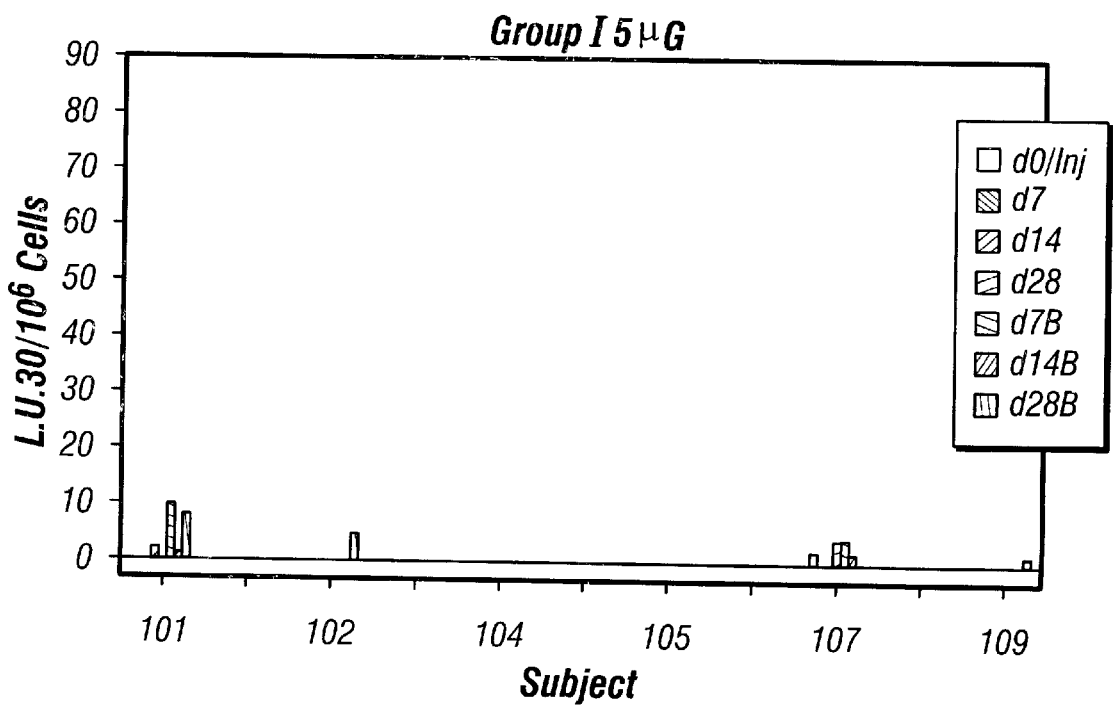
Figure 15C:
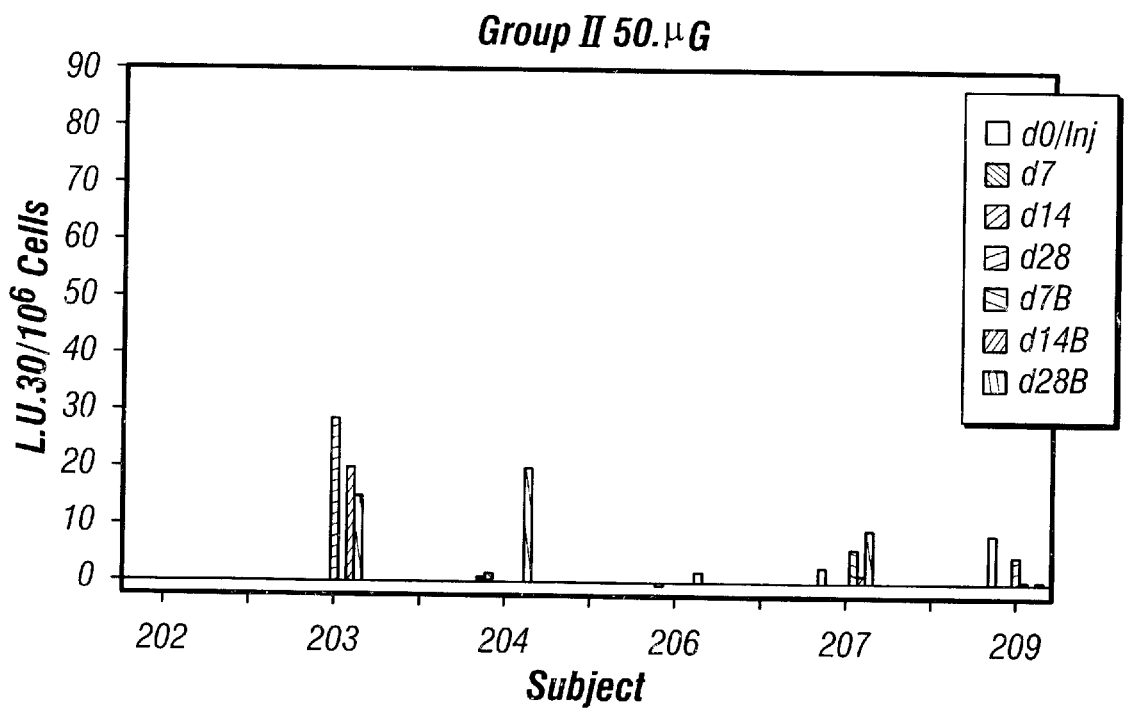
Figure 15D:
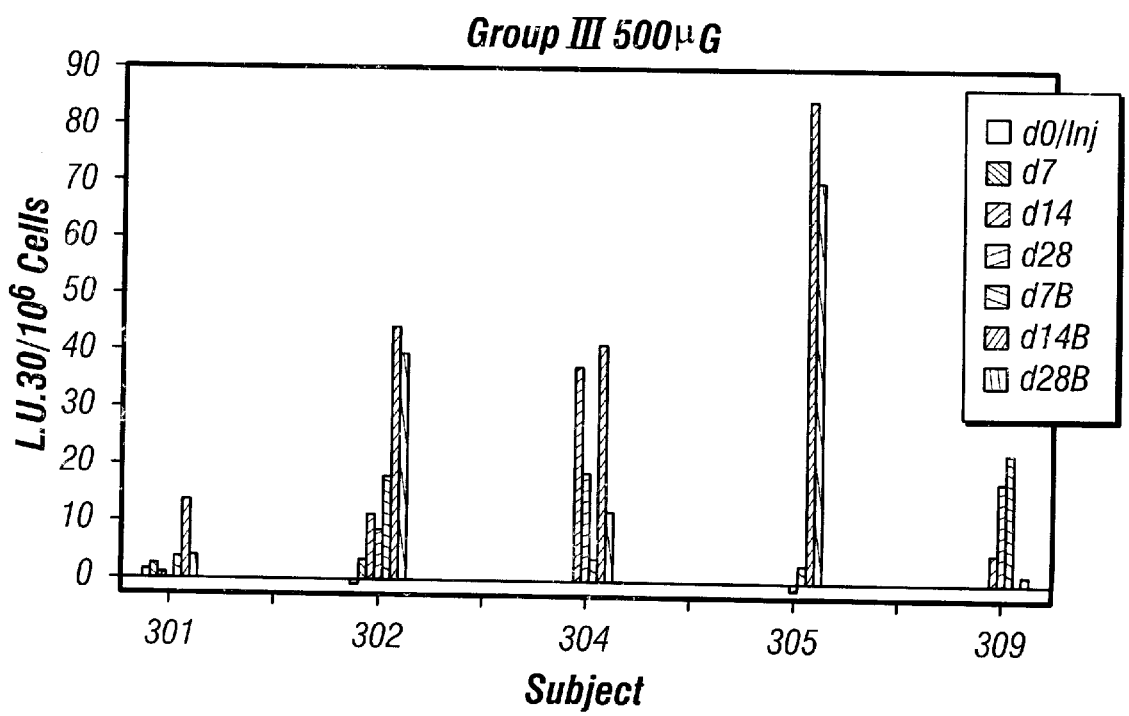

Transgenic mice (A2-1/Kb) were primed with HBV virus in IFA substantially as described in Example II. Seven days after priming, splenocytes obtained from these animals were restimulated with syngeneic irradiated LPS blasts coated with peptide 799.09 (as described in Example I). After 6 cycles of restimulation with 799.09 coated cells (as described in Example II) the effector cells were cloned by limiting dilution using syngeneic irradiated LPS blasts coated with peptide 799.09 ($0.2 \times 10^6$ cells/well of a 96 well plate) and media supplemented with 10% rat Con A supernatant. Two CTL lines were obtained, line 110 and 113 that killed JA2Kb target cells coated with peptide 799.09. These lines were tested on a panel of 799.09 N-terminus truncated peptides and overlapping 9mers and 10mers covering the entire 799.09 sequence. As shown in FIG. 13 panel A the minimal N-terminus truncated peptide recognized by line 113 and 110 were respectively peptides HBV env. 333–348 (923-09) and 335–348 (923.07). FIG. 13 panel B shows that none of the 9mers or 10mers were recognized by line 113 implicating a longer peptide as the minimal sequence required for recognition by this CTL line. The minimal sequence recognized by line 110 is represented by peptides HBV env. 333–341 (923.26) and HBV env 335–343 (923.22) indicating that possibly two distinct but overlapping peptides can serve as antigenic determinants for 799.09 specific CTL.

EXAMPLE 9

Priming of Peptide 934.05 ("CY-1899") IN Transgenic Mice

This example discloses that peptide 934.02 (i.e., tetanus toxoid 830–843-AAA-HBcAg 18–27) when modified by linking $(PAM)_2$KSS to the tetanus toxoid end (resulting in "CY-1899") and formulated in DMSO/saline induced CTLs in transgenic mice.

Lipopeptides were prepared by coupling the appropriate fatty acid to the amino terminus of the resin bound peptide. A typical procedure was as follows: A dichloromethane solution of a 4 fold excess of a pre-formed symmetrical anhydride of the appropriate fatty acid was added to the resin an the mixture was allowed to react for 2 hrs. The resin was washed with dichloromethane and dried. The resin was then treated with trifluoroacetic acid in the presence of appropriate scavengers [e.g. 5% (v/v) water] for 60 minutes at 20° C. After evaporation of excess trifluoroacetic acid, the crude peptide was washed with diethyl ether, dissolved in methanol and precipitated by the addition of water. The peptide was collected by filtration and dried.

Preparation of Peptides for Immunization:

Peptides were routinely resuspended in DMSO at a concentration of 20 mg/ml. Before use, peptides were prepared at the required concentration by dilution in saline or the appropriate medium. For selected experiments, CY-1899 and 934.02 were also prepared as saline suspensions (in the complete absence of DMSO).

Immunization Procedures:

Transgenic mice were primed subcutaneously (base of the tail) with 0.1 ml of the appropriate peptide formulated in saline, or DMSO/saline.

Media:

a. RPMI-1640 supplemented with 10% fetal calf serum (FCS) 2 mM Glutamine, 50 µg/ml Gentamicin and $5 \times 10^{-5}$ 2-mercaptoethanol served as culture medium and will be referred to as R10 medium.

b. RPMI-1640 containing 25 mM HEPES buffer and supplemented with 2% (FCS) was used as cell washing medium.

Cell Lines:

Jurkat A2.1/$K^b$ (5) is a stable transfectant of the human T cell leukemia line, Jurkat. Jurkat A2.1/$K^b$ cells were routinely grown in R10 medium supplemented with 400 µg/ml of G418.

LPS-activated Lymphoblasts:

Splenocytes obtained from A2.1/$K^b$ transgenic mice were resuspended at a concentration of $1-1.5 \times 10^6$/ml in R10 medium supplemented with 25 µg/mi LPS and 7 µg/ml dextran sulfate in 75 $cm^2$ tissue culture flasks. After 72 hr at 37° C., the lymphoblasts were collected for use by centrifugation.

Peptide Coating of Lymphoblasts:

Peptide coating of the LPS activated lymphoblasts was achieved by incubating $30 \times 10^6$ irradiated (3000 rads) lymphoblasts with 100 µg of peptide in 1 ml of R10 medium for 1 hr at 37° C. Cells were then washed once and resuspended in Rio medium at the desired concentration.

In Vitro CTL Activation:

One to four weeks after priming spleen cells ($30 \times 10^6$ cells/flask) were co-cultured at 37° C. with syngeneic, irradiated (3000 rads), peptide coated lymphoblasts ($10 \times 10^6$ cells/flask) in 10 ml of R10 medium/T25 flask. After 6 days, the effector cells were harvested and assayed for cytotoxic activity.

Assay for Cytotoxic Activity:

Target cells (1.0-1.5×10$^6$) were incubated at 37° C in the presence of 200 μl of sodium $^{51}$Cr chromate. After 60 minutes, cells were washed three times and resuspended in R10 medium. Peptide 875.15 was added where required at a concentration of 1 μg/ml. For the assay, 10$^4$ $^{51}$Cr-labeled target cells were added to different concentrations of effector cells (final volume of 200 μl) in U-bottom 96-well plates. After a 6 hour incubation period at 37° C., a 0.1 ml aliquot of supernatant was removed from each well and radioactivity was determined in a Micromedic automatic gamma counter. The percent specific lysis was determined by the formula: percent specific release=100×(experimental release−spontaneous release)/(maximum release−spontaneous release). For the purpose of easy comparison between separate CTL assays run under the same conditions, % $^{51}$Cr release data was expressed as lytic units/10$^6$ cells. One lytic unit is arbitrarily defined as the number of effector cells required to achieve 30% lysis of 10,000 Jurkat A2.1/K$^b$ target cells in a 6 hour $^{51}$Cr release assay. To obtain specific lytic units/10$^6$, the lytic units/10$^6$ obtained in the absence of peptide is subtracted from the lytic units/10$^6$ obtained in the presence of peptide. For example, if 30% $^{51}$Cr release is obtained at the E:T of 50:1 (i.e., 5×10$^5$ effector cells for 10,000 targets) in the absence of peptide and 5:1 (i.e., 5×10$^4$ effector cells for 10,000 targets) in the presence of peptide, the specific lytic units would be: $(1\times10^{6+5\times10^4})-(1\times10^{6+5\times10^5})=18LU/10^6$.

RESULTS:

The results indicated that CY 1899 (i.e., tetanus toxoid 830–843-AAA-HBcAg 18–27) formulated in DMSO/saline is a strong immunogenic preparation inducing a good CTL response in all animals injected (six out of six).

CY 1899 in saline (without prior solubilizationinduced a poor CTL response in that only one of six animals injected had detectable CTL activity.

Peptide 934.02 in saline induced a marginal CTL response in that only one of the four animals tested had detectable CTL activity.

No CTL activity was detected in any of the animals injected with peptide 934.02 in DMSO/saline.

CTL induced by CY-1899 were shown to be able to kill cells expressing endogenous HBc antigen.

EXAMPLE 10

The Effect of Lipidation of T Helper Epitope on CTL Induction

This example discloses that the desired CTL activity is induced in the absence of adjuvant (IFA or Alum) by lipidation of the T-Helper epitope where the T-Helper epitope and the CTL epitope are not linked.

The effect of lipidation of the HTL peptide epitope on the immunogenicity of PR8-NP 147–155 CTL peptide epitope was determined. Peptides used in this Example were as follows:

Balb/c mice were injected with the different combinations indicated above of HTL (100 nmoles/mouse) and CTL (10 nmoles/mouse) peptide epitope in saline. Four animals were injected with each different preparation. Ten days after immunization, splenocytes were stimulated in vitro with NP 147–155 peptide. CTL activity was assayed 6 days later using $^{51}$Cr-labeled B10.D2 fibroblasts as targets in the absence or presence of NP 147–155 peptide. The data are expressed in lytic units/10$_6$ cells. One lytic unit is arbitrarily defined as the number of lymphocytes required to achieve 30% lysis of 5000 B10.D2 $_{51}$Cr-labeled target cells within 6 hours, in the absence or presence of NP 147–155 peptide. (a) Each number represents the specific CTL activity (LU 30/10$_6$ cells obtained in the presence of NP 147–155-LU 30/106 cells obtained in the absence of NP 147–0155) from an individual mouse.

| Effect of HTL peptide epitope and peptide liquidation on the immunogenicity of PR8-NP 147–155 CTL peptide epitope | | |
|---|---|---|
| Priming Peptide Cytel ID Number | Description | LU30 (Geometric Mean) |
| 932.01 | CTL | 0 (a) |
| | | 0.2 |
| | | 0 |
| | | 0 |
| | | (0.1 x/+ 1.4) |
| 932.01 + 577. 01 | CTL + HTL | 0 |
| | | 0.3 |
| | | 0 |
| | | 0 |
| | | (0.1 x/+ 1.7) |
| 932.07 | (PAM)$_2$ – CTL | 0 |
| | | 0 |
| | | 0.5 |
| | | 0 |
| | | (0.15 x/+ 2.2) |
| 932.07 + 577.01 | (PAM)$_2$ – CTL + HTL | 1 |
| | | 1.1 |
| | | 12.4 |
| | | 0 |
| | | (1.1 x/+ 7.2) |
| 932.01 + 932.06 | CTL + (PAM)$_2$ – HTL | 9.3 |
| | | 74.1 |
| | | 1.7 |
| | | 69.5 |
| | | (16.9 x/+ 6.1) |
| 932.07 + 932. 06 | (PAM)$_2$ – CTL + (PAM)$_2$ – HTL | 2.5 |
| | | 1 |
| | | 1 |
| | | 11.7 |
| | | (2.3 x/+ 6.1) |
| 932.04 | (PAM)$_2$ – HTL – CTL | 4.7 |
| | | 2 |
| | | 21 |
| | | 1.2 |
| | | (3.9 xx/+ 3.5) |

The results obtained indicate that, 1) unlipidated peptides (932.01 and 932.01+577.01) are ineffective at the concentrations tested when injected in saline; 2) the presence of

| ID# | Description | Sequence | Seq ID No. |
|---|---|---|---|
| 932-01 | CTL | TYQRTRALV (PR8-NP 147–155) | 116 |
| 932.07 | (PAM)$_2$-CTL | (PAM)$_2$KSSTYQRTRALV | 117 |
| 577.01 | HTL | ISQAVHAAHAEINE | 98 |
| 932.06 | (PAM)$_2$-HTL | (PAM)$_2$KSSISQAVHAAHAEINE | 123 |
| 932.04 or | (PAM)$_2$-HTL-CTL | (PAM)$_2$KSSISQAVHAAHAEINETYQRTRALV | 124 | both the HTL and the CTL peptide epitope and the lipidation of at least one peptide is necessary for CTL induction when the peptides are formulated in saline.

The preferred combination appeared to be the lipidated HTL peptides unlinked to the unlipidated CTL peptide. Thus, a titration of the CTL epitope and the lipidated HTL epitope in mixtures was performed (i.e., the titration of (PAM)$_2$-HTL peptide epitope and CTL peptide epitope in mixtures).

Balb/c mice were injected with 10 nmoles of the linked [(PAM)$_2$-HTL-CTL] peptide immunogen and with mixtures containing 0, 1, 10, or 100 nmoles CTL epitope (932.01) and 0, 1, 10, or 100 nmoles PAM-helper epitope (932.06) per mouse as indicated in the table. Four animals were injected with each different preparation. Fourteen days after immunization, splenocytes were removed and stimulated in vitro with the NP 147–155 peptide. CTL activity was assayed 6 days later using $^{51}$Cr-labeled B10.D2 fibroblasts as targets. Target cells were tested in the absence or presence of antigen (NP 147–155 peptide). The data are expressed in lytic units/10$^6$ cells. One lytic unit is arbitrarily defined as the number of lymphocytes required to achieve 30% lysis of 5000 B10.D2 $^{51}$Cr-labeled target cells within 6 hours, in the absence or presence of antigen (NP 147–155 peptide). (a) Each number represents the specific CTL activity (LU 30/106 cells; obtained in the presence of NP 147–155—LU 30/106 cells obtained in the absence of NP 147 155) from an individual mouse.

Titration of (PAM)$_2$-HTL peptide epitope and CTL peptide epitope contained in mixtures

| | nmoles CTL epitope, 932.01 | | | |
|---|---|---|---|---|
| | 0 LU 30 Geo Mean | 1 LU 30 Geo Mean | 10 LU 30 Geo Mean | 100 LU 30 Geo Mean |
| nmoles (PAM)$_2$ – HTL epitope | | | | |
| 932.06 | | | | |
| 0 | | | | 3.8(a) |
| | | | | 0.8 |
| | | | | 0.3 |
| | | | | 1.3 |
| | | | | 1.0 x/+ 2.9 |
| 1 | | 3.8 | 2.5 | 3 |
| | | 23.9 | 4.4 | 7.4 |
| | | 2.6 | 0.2 | 2.6 |
| | | 0.2 | 4.4 | 2.6 |
| | | 2.6 x/+ 7.2 | 1.8 x/+ 4.4 | 3.5 x/+ 1.7 |
| 10 | | >58 | 50 | 68 |
| | | 29.5 | 20.3 | 53 |
| | | 2.2 | 7.3 | >64 |
| | | 53.5 | 27.5 | >68 |
| | | 21.2 x/+ 4.7 | 21.2 x/+ 2.2 | 62.9 x/+ 1.1 |
| 100 | 1.5 | 26 | 69 | 64 |
| | 0.8 | 61 | >58 | >64 |
| | 0.7 | 63 | >41 | 73 |
| | 0 | >54 | 7.9 | 62 |
| | 0.5 x/+ 3.2 | 48.2 x/+ 1.5 | 33.7 x/+ 2.7 | 65.6 x/+ 1.1 |
| (PAM)$_2$ – HTL – CTL65 | 90 | | | |
| 10 nmoles 1053.05 | 17.8 | | | |
| | 25.4 | | | |
| | 40.3 x/+ 2.1 | | | |

The results obtained indicate that optimal CTL induction (i.e., comparable to that achieved by immunization with 10 nmoles of the linked immunogen 1053.05) is achieved with mixtures containing 100 nmoles of the 932.06 [(PAM)2 HTL] peptide and 1, 10 or 100 nmoles of the 932.01 (CTL) peptide. In the presence of 10 nmoles of 932.06, optimal CTL induction is achieved by the mixture containing 100 nmoles of 932.01 while a slight decrease was observed in the mixtures containing either 10 or 1 nmoles of the CTL peptide. Mixtures containing 1 nmole of the HTL peptide resulted rather inefficiently.

Lipidated T-Helper Epitopes with Multiple CTL Epitopes.

By following the procedures described in this Example 10, a composition of matter comprising of a lipidated HTL admixed with multiple CTL epitopes can be prepared. Optionally, the CTL epitopes can be packaged in different vials from the HTL epitope(s).

EXAMPLE 11

INDUCTION OF SPECIFIC CTL RESPONSE IN HUMANS

The human clinical trial for CY-1899 was set up as an IDN Phase I dose escalation study (5, 50 and 500 μg) and was carried out in a single center as a randomized double-blind placebo controlled trial.

A total of 27 subjects were enrolled and divided into 3 groups:
  Group I: 3 subjects were injected with placebo and 6 subjects were injected with 5 μg of CY-1899;
  Group II: 3 subjects were injected with placebo and 6 subjects were injected with 50 μg of CY-1899;
  Group III: 3 subjects were injected with placebo and 6 subjects were injected with 500 μg of CY-1899.

After 5 weeks (GI and GII) or 4 weeks (GIII) following the first injection, all subjects received a booster inoculation at the same dosage.

The endpoints measured in this study relate to the safety and tolerability of CY-1899 (also known as Theradigm-HBV) as well as its immunogenicity. Cellular immune responses to CY-1899 are an index of the intrinsic activity of this drug, and can therefore be viewed as a measure of biological efficacy. The following summarized the clinical and laboratory data relating to safety and efficacy endpoints.

Safety:

Adverse events were observed with similar frequency in the placebo and drug treatment groups. All adverse events were judged to be mild in degree and completely reversible. No relationship between adverse events and dose level were found. The most common adverse events were headache (4 subjects) and skin reaction at the site of inoculation (3 subjects).

Evaluation of Vaccine Efficacy:

For evaluation of vaccine efficacy subjects were bled before and after injection. Peripheral blood mononuclear cells were isolated from fresh heparinized blood by Ficoll-Hypaque density gradient centrifugation, aliquoted in freezing media and stored frozen. Samples were assayed for CTL and HTL activity.

Figure 16:
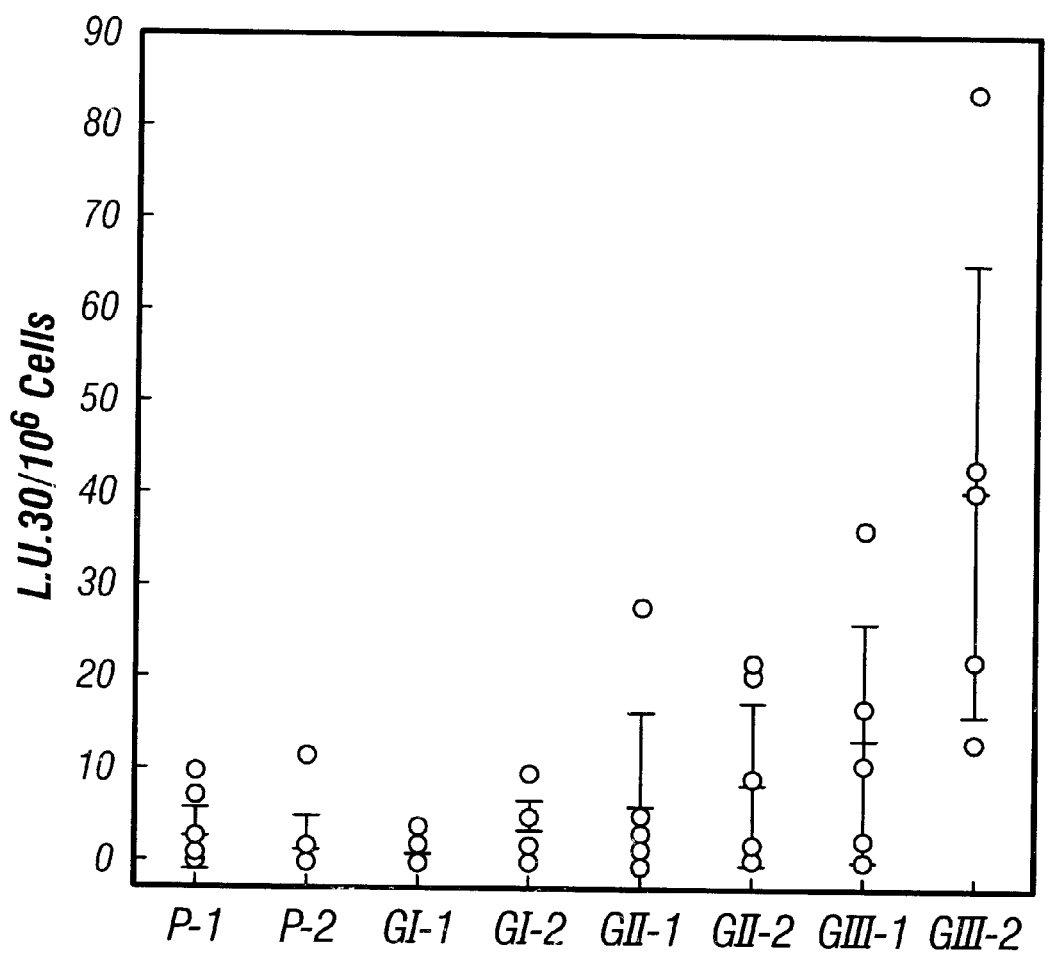
FIG. 16 shows the mean and standard deviation of peak CTL activity: the mean and standard deviation of peak CTL activity after the first and second injections of different doses of CY-1899.
Figure 18A:
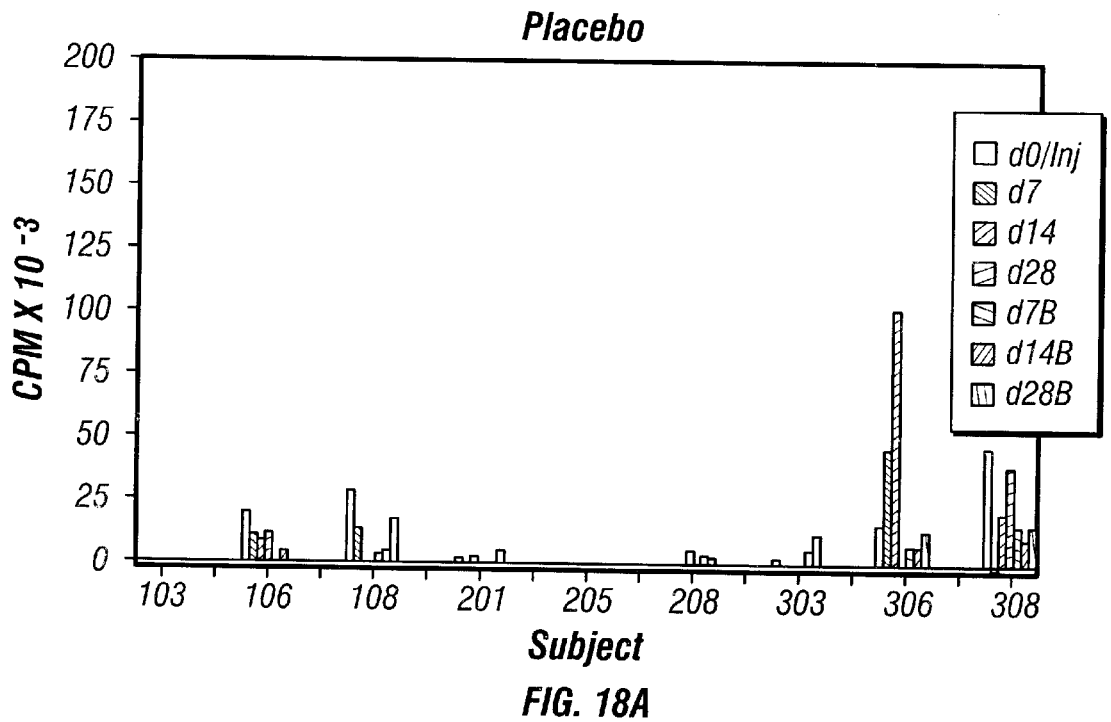
FIGS. 18A–18D show the proliferation response to T cells specific for the TT 830–843 helper peptide from subjects immunized with placebo or CY-1899. T cell proliferation response against the helper peptide epitope was measured by culturing 1.5×10$^5$ PBMC from each sample in flat-bottom 96/plate wells with or without 10 μg/ml TT peptide. Seven days later, cultures were fed with medium containing recombinant IL-2 (20 U/ml final concentration) to induce further proliferation of T cells which had been stimulated against the peptide. On day 9 after initiation of culture, 1 μCl of $^3$H-thymidine was added to each well and 18 hr. later, cells in each well were harvested onto glass fiber mats and counted for $^3$H-thymidine incorporation into DNA. Each bar represents the difference in cpm $^3$H-thymidine incorporation obtained from wells which received peptide minus those which did not receive peptide.
Figure 18B:
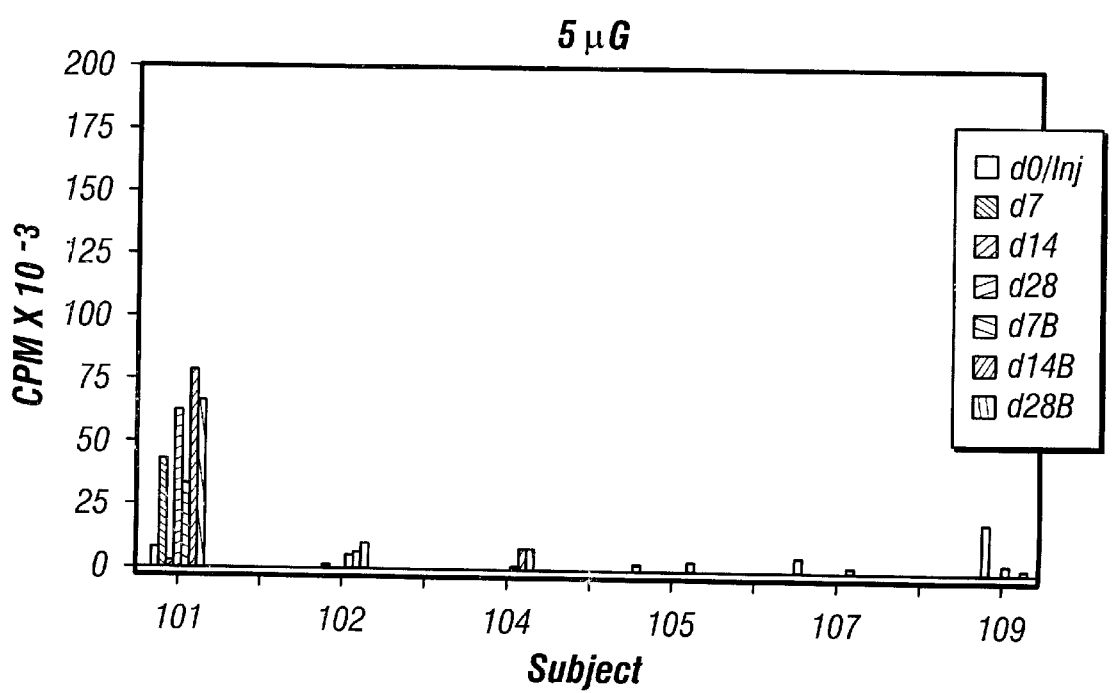
Figure 18C:
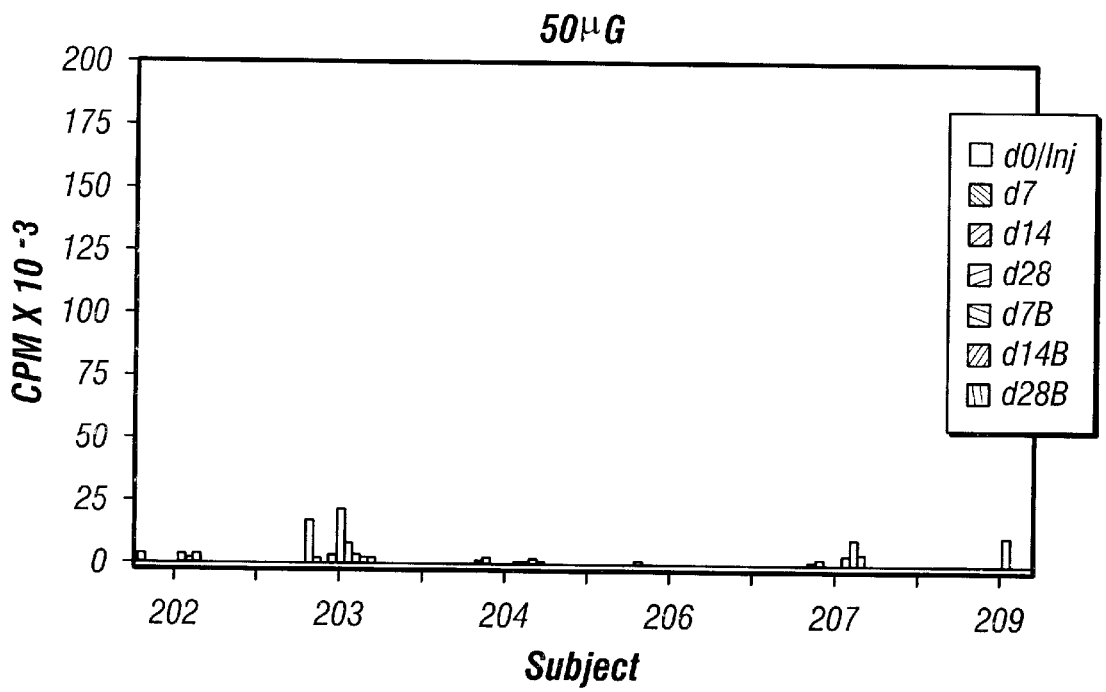
Figure 18D:
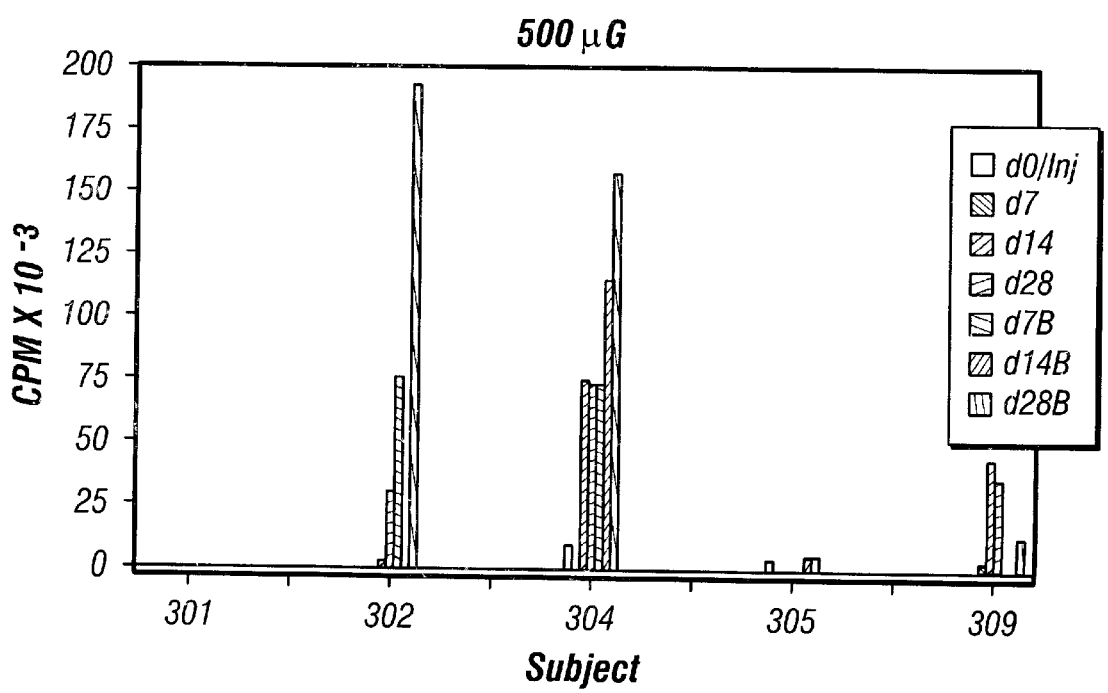

Data:

Injection of CY-1899 in normal volunteers resulted in induction of HBc18–27 specific CTL are disclosed in FIGS. 14 and 15. The CTL response observed was dose dependent both in the proportion of subjections exhibiting a positive response as well as in the magnitude of the response obtained. The dose response effect is demonstrated in FIG. 16 where the mean peak CTL activity per each group of subjects after the first and second injections are shown.

The peptide-induced CTL responses were capable of killing cells expressing endogenous antigen (as disclosed in FIG. 17) validating the concept of peptide priming for induction of virus specific CTL.

The proliferative T cell response against the helper TT peptide among the subjects receiving the three doses of CY-1899 correlates with their CTL responses (as disclosed in FIG. 18). The most striking T cell responses against the TT helper peptide were observed in individuals receiving the highest vaccine dose. In three out of four subjects in this dose group a strong T cell proliferative response against TT peptide was correlated with high levels of CTL induction following vaccination with CY-1899. The only instance where a strong CTL response was observed in the absence of helper T cell induction was in the case of an individual who demonstrated a late CTL response 14 days after boosting.

EXAMPLE 12

SPECIFIC CTL INDUCING VACCINE FOR PREVENTING AND/OR TREATING HCV

By following the procedures disclosed in Examples 1–11 a therapeutic composition of matter useful for treating mammals with HCV infections by inducing specific CTLs can be made.

For example, following the procedures in Examples 1, and 2, or alternatively Example 2A, peptides suitable for inducing CTLs can be identified, for example, the following peptides:

| SOURCE | POSI-TION | SEQUENCE | SIZE | SEQ. ID NO. | BINDING A2 |
|---|---|---|---|---|---|
| HCV NS4 | 1807 | LLFNILGGWV | 10 | 125 | 3.5000 |
| HCV CORE | 178 | LLALLSCLTV | 10 | 126 | 0.6050 |
| HCV NS4 | 1585 | YLVAYQATV | 9 | 127 | 0.2450 |
| HCV NS1/ENV | 725 | FLLLADARV | 9 | 128 | 0.2250 |
| HCV NS4 | 1851 | ILAGYGAGV | 9 | 129 | 0.2150 |
| HCV CORE | 132 | DLMGYIPLV | 9 | 130 | 0.0835 |
| HCV CORE | 35 | YLLPRRGPRL | 10 | 131 | 0.0725 |
| NS1/ENV2 | 686 | ALSTGLIHL | 9 | 132 | 0.0415 |
| HCV CORE | 178 | LLALLSCLTI | 10 | 133 | 0.0340 |
| HCV NS5 | 2578 | RLIVFPDLGV | 10 | 134 | 0.0320 |
| HCV NS5 | 2885 | RLHGLSAFSL | 10 | 135 | 0.0200 |
| HCV NS4 | 1811 | ILGGWVAAQL | 10 | 136 | 0.0180 |
| HCV ENV1 | 364 | SMVGNWAKV | 9 | 137 | 0.0155 |
| HCV NS3 | 1131 | YLVTRHADV | 9 | 138 | 0.0109 |
| HCV NS4 | 1666 | VLAALAAYCL | 10 | 139 | 0.0106 |

Once identified, such desired peptides can be obtained either commercially or prepared following the procedures disclosed in Example 3.

The preferability of the identified peptides is elaborated by optimization of the configuration of the composition of matter (i.e., whether the T-Helper and CTL peptides are linked or unlinked, and whether the peptides are delivered in a saline, alum or IFA medium, lipidated T-Helper linked or unlinked to the CTL in saline, or linked and unlinked T-Helper with CTL in IFA).

By following the procedures disclosed above and in the preceding examples a vaccine capable of treating HCV can be obtained.

EXAMPLE 13

Specific CTL Inducing Vaccine for Preventing AND/OR Treating Melanoma

By following the procedures disclosed in Examples 1–10 a therapeutic composition of matter useful for treating mammals with melanomas by inducing specific CTLs can be made.

For example, following the procedures in Examples 1, and 2, or alternatively Example 2A, peptides suitable for inducing CTLs can be identified, for example, the following peptides:

| SOURCE | POSI-TION | SEQUENCE | SIZE | SEQ. ID NO. | BINDING A2 |
|---|---|---|---|---|---|
| MAGE2 | 105 | KMVELVHFL | 9 | 140 | 0.5100 |
| MAGE2 | 105 | KMVELVHFLL | 10 | 141 | 0.2200 |
| MAGE3 | 153 | LVFGIELMEV | 10 | 142 | 0.1100 |
| MAGE1 | 278 | KVLEYVIKV | 9 | 143 | 0.0900 |
| MAGE1 | 105 | KVADLVGFLL | 10 | 144 | 0.0560 |
| MAGE3 | 105 | KVAEFVHFL | 9 | 145 | 0.0550 |
| MAGE1 | 92 | CILESLFRA | 9 | 146 | 0.0460 |
| MAGE1 | 264 | FLWGPRALA | 9 | 147 | 0.0420 |
| MAGE1 | 200 | VMIAMEGGHA | 10 | 148 | 0.0360 |
| MAGE1 | 38 | LVLGTLEEV | 9 | 149 | 0.0320 |
| MAGE1 | 301 | ALREEEGV | 9 | 150 | 0.0210 |
| MAGE1 | 270 | ALAETSYVKV | 10 | 151 | 0.0150 |
| MAGE1 | 282 | YVIKVSARV | 9 | 152 | 0.0140 |
| MAGE1 | 269 | RALAETSYV | 9 | 153 | 0.0100 |

Once identified, such desired peptides can be obtained either commercially or prepared following the procedures disclosed in Example 3.

The preferability of the identified peptides is elaborated by optimization of the configuration of the composition of matter (i.e., whether the T-Helper and CTL peptides are linked or unlinked, and whether the peptides are delivered in a saline, alum or IFA medium, lipidated T-Helper linked or unlinked to the CTL in saline, or linked and unlinked T-Helper with CTL in IFA).

By following the procedures disclosed above and in the preceding examples a vaccine capable of treating melanomas can be obtained.

EXAMPLE 14

Specific CTL Inducing Vaccine for Preventing AND/OR Treating HPV

By following the procedures disclosed in Examples 1–10 a therapeutic composition of matter useful for treating mammals with HPV infections by inducing specific CTLs can be made.

For example, following the procedures in Examples 1, and 2, or alternatively Example 2A, peptides suitable for inducing CTLs can be identified, for example, the following peptides:

| SOURCE | POSI-TION | SEQUENCE | SIZE | SEQ. ID NO. | BINDING A2 |
|---|---|---|---|---|---|
| HPV16 E7 | 82 | LLMGTLGIV | 9 | 65 | 0.0240 |
| HPV16 E7 | 11 | YMLDLQPET | 9 | 66 | 0.1400 |
| HPV16 E6 | 52 | FAFRDLCIV | 9 | 67 | 0.0570 |
| HPV16 E7 | 86 | TLGIVCPIC | 9 | 68 | 0.0750 |
| HPV16 E7 | 7 | TLHEYMLDL | 9 | 69 | 0.0070 |
| HPV16 E7 | 85 | GTLGIVCPI | 9 | 70 | 0.0820 |
| HPV16 E7 | 12 | MLDLQPETT | 9 | 71 | 0.0028 |
| HPV16 E6 | 29 | TIHDIILECV | 10 | 72 | 0.0210 |

Once identified, such desired peptides can be obtained either commercially or prepared following the procedures disclosed in Example 3.

The preferability of the identified peptides is elaborated by optimization of the configuration of the composition of matter (i.e., whether the T-Helper and CTL peptides are linked or unlinked, and whether the peptides are delivered in a saline, alum or IFA medium, lipidated T-Helper linked or unlinked to the CTL in saline, or linked and unlinked T-Helper with CTL in IFA).

By following the procedures disclosed above and in the preceding examples a vaccine capable of treating HPV can be obtained.

EXAMPLE 15

Specific CTL Inducing Vaccine for Preventing AND/OR Treating HIV

By following the procedures disclosed in Examples 1–10 a therapeutic composition of matter useful for treating humans with HIV infections by inducing specific CTLs can be made.

For example, following the procedures in Examples 1, and 2, or alternatively Example 2A, peptides suitable for inducing CTLs can be identified, for example, the following peptides:

| SOURCE | POSI-TION | SEQUENCE | SIZE | SEQ. ID NO. | BINDING A2 |
|---|---|---|---|---|---|
| HIV | 367 | VLAEAMSQV | 9 | 73 | 0.1100 |
| HIV | 1496 | LLWKGEGAVV | 10 | 74 | 0.0360 |
| HIV | 1496 | LLWKGEGAV | 9 | 75 | 0.0230 |
| HIV | 1004 | ILKEPVHGV | 9 | 76 | 0.0190 |

-continued

| SOURCE | POSI-TION | SEQUENCE | SIZE | SEQ. ID NO. | BINDING A2 |
|---|---|---|---|---|---|
| HIV | 1129 | IVGAETFYV | 9 | 77 | 0.0099 |
| HIV | 1129 | IIGAETFYV | 9 | 78 | 0.0260 |
| HIV | 2182 | LWVTVYYGV | 9 | 79 | 0.0014 |
| HIV | 2182 | LMVTVYYGV | 9 | 80 | 0.4400 |

Once identified, such desired peptides can be obtained either commercially or prepared following the procedures disclosed in Example 3.

The preferability of the identified peptides is elaborated by optimization of the configuration of the composition of matter (i.e., whether the T-Helper and CTL peptides are linked or unlinked, and whether the peptides are delivered in a saline, alum or IFA medium, lipidated T-Helper linked or unlinked to the CTL in saline, or linked and unlinked T-Helper with CTL in IFA).

By following the procedures disclosed above and in the preceding examples a vaccine capable of treating HIV can be obtained.

From the foregoing it will be appreciated that, although specific embodiments of the invention have been described herein for purposes of illustration, various modifications may be made without deviating from the spirit and scope of the invention. Accordingly, the invention is not limited except as by the appended claims.

---

What is claimed is:

1. An immunogenically effective composition comprising:

(i) a first peptide comprising an epitope, wherein the first peptide binds to an HLA class I molecule to form an epitope-HLA complex recognized by a human cytotoxic T cell wherein the said epitope recognized by a human cytotoxic T cell is a hepatitis B virus epitope, a hepatitis C virus epitope, a human immunodeficiency virus epitope, or a human papilloma virus epitope;

(ii) a second peptide comprising an epitope, wherein the second peptide binds to an HLA class II molecule to form an epitope-HLA complex recognized by a human helper T cell;

(iii) an adjuvant; and (iv) a physiologically acceptable carrier.

2. The composition of claim 1, wherein the second peptide is covalently linked to the first peptide.

3. The composition of claim 1, wherein the second peptide is not linked to the first peptide.

4. The composition of claim 1, wherein the first peptide is linked to the second peptide by a spacer molecule.

5. The composition of claim 1, wherein the first peptide and/or the second peptide are each from six to thirty amino acid residues in length.

6. The composition of claim 1, wherein the first and/or the second peptide comprises a plurality of epitopic units.

7. The composition of claim 1, wherein the adjuvant is incomplete Freund's adjuvant, complete Freund's adjuvant, alum, aluminum hydroxide, or a lipid.

8. The composition of claim 1, wherein the adjuvant is a lipid and is linked to the first peptide.

9. The composition of claim 1, wherein the adjuvant is a lipid and is linked to the second peptide.

10. The composition of claim 1, wherein the adjuvant is a lipid and is linked to the first and the second peptide.

11. A method for stimulating an immune response in a human against an epitope, comprising the steps of:

(a) providing a first peptide comprising an epitope, wherein the first peptide binds to an HLA class I molecule to form an epitope-HLA complex recognized by a human cytotoxic T cell wherein the said epitope recognized by a human cytotoxic T cell is a hepatitis B virus epitope, a hepatitis C virus epitope, a human immunodeficiency virus epitope, or a human papilloma virus epitope;

(b) providing a second peptide comprising an epitope, wherein the second peptide binds to an HLA class II molecule to form an epitope-HLA complex recognized by a human helper T cell;

(c) providing an adjuvant; and (d) administering the first and second peptides and the adjuvant to the human.

12. The method of claim 11, wherein the second peptide is covalently linked to the first peptide.

13. The method of claim 11, wherein the second peptide is not linked to the first peptide.

14. The method of claim 11, wherein the first peptide is linked to the second peptide by a spacer molecule.

15. The method of claim 11, wherein the administration step comprises administering the first peptide, second peptide and the adjuvant concurrently.

16. The method of claim 11, further comprising, following step (d), a step (e) administering the first and second peptides to the human, whereby the administration steps (d) and (e) are spaced a sufficient interval apart to optimize development of said immune response to the epitopes.

17. The method of claim 16, wherein the administration step (e) comprises administering the second peptide and the first peptide approximately four weeks after the administration step (d).

18. The method of claim 11, wherein the first peptide and/or the second peptide are each from six to thirty amino acid residues in length.

19. The method of claim 11, wherein the first and/or the second peptide comprises a plurality of epitopic units.

20. The method of claim 11, wherein the first and the second peptides are administered with a physiologically-acceptable carrier.

21. The method of claim 11, wherein the adjuvant is alum, aluminum hydroxide, or a lipid.

22. The method of claim 11, wherein the first peptide is administered with the adjuvant.

23. The method of claim 22, wherein the adjuvant is a lipid and the first peptide is linked to the adjuvant.

24. The method of claim 11, wherein the second peptide is administered with the adjuvant.

25. The method of claim 24, wherein the adjuvant is a lipid and the second peptide is linked to the adjuvant.

26. The method of claim 11, wherein the first peptide and the second peptide are administered with an adjuvant.

27. The method of claim 26, wherein the adjuvant is a lipid and the first peptide and the second peptide are both linked to the adjuvant.

* * * * *

UNITED STATES PATENT AND TRADEMARK OFFICE
CERTIFICATE OF CORRECTION

PATENT NO. : 6,419,931 B1  Page 1 of 1
DATED : July 16, 2002
INVENTOR(S) : Maria A. Vitello et al.

It is certified that error appears in the above-identified patent and that said Letters Patent is hereby corrected as shown below:

<u>Title page,</u>
Item [75], Inventors, change "Chestnut" to -- Chesnut --

Signed and Sealed this

Twenty-eighth Day of January, 2003

JAMES E. ROGAN
*Director of the United States Patent and Trademark Office*